(12) United States Patent
Boyd et al.

(10) Patent No.: US 7,163,940 B2
(45) Date of Patent: *Jan. 16, 2007

(54) PYRAZOLOPYRIDINYL PYRIMIDINE THERAPEUTIC COMPOUNDS

(75) Inventors: F. Leslie Boyd, Durham, NC (US); Stanley D Chamberlain, Durham, NC (US); Mui Cheung, Durham, NC (US); Kristjan Gudmundsson, Durham, NC (US); Philip Anthony Harris, Durham, NC (US); Brian A Johns, Durham, NC (US); David Kendall Jung, Durham, NC (US); Michael Robert Peel, Durham, NC (US); Jennifer G Badiang, Durham, NC (US); Connie Jo Sexton, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 312 days.

This patent is subject to a terminal disclaimer.

(21) Appl. No.: 10/433,881

(22) PCT Filed: Nov. 26, 2001

(86) PCT No.: PCT/US01/44231

§ 371 (c)(1),
(2), (4) Date: Jun. 5, 2003

(87) PCT Pub. No.: WO02/16359

PCT Pub. Date: Feb. 28, 2002

(65) Prior Publication Data

US 2005/0049259 A1 Mar. 3, 2005

Related U.S. Application Data

(60) Provisional application No. 60/274,284, filed on Mar. 8, 2001, provisional application No. 60/255,763, filed on Dec. 15, 2000.

(51) Int. Cl.
C07D 471/04 (2006.01)
A61K 31/435 (2006.01)
C07D 401/04 (2006.01)

(52) U.S. Cl. .............. 514/235.8; 514/252.18; 514/274; 514/275; 544/122; 544/316; 544/331

(58) Field of Classification Search ............... 544/122, 544/316, 331; 514/235.8, 274, 252.18, 275
See application file for complete search history.

(56) References Cited

U.S. PATENT DOCUMENTS

| | | | |
|---|---|---|---|
| 4,576,952 A | 3/1986 | Hurst et al. | |
| 4,621,089 A | 11/1986 | Ward et al. | |
| 4,670,432 A | 6/1987 | Ward et al. | |
| 4,985,444 A | 1/1991 | Shiokawa et al. | |
| 5,155,114 A | 10/1992 | Shiokawa et al. | |
| 5,204,346 A | 4/1993 | Shiokawa et al. | |
| 5,234,930 A | 8/1993 | Shiokawa et al. | |
| 5,296,490 A | 3/1994 | Shiokawa et al. | |
| 5,300,478 A | 4/1994 | Michaely et al. | |
| 5,498,774 A | 3/1996 | Mitsudera et al. | |
| 5,552,422 A | 9/1996 | Gauthier et al. | |
| 5,700,816 A | 12/1997 | Isakson et al. | |
| 5,990,148 A | 11/1999 | Isakson et al. | |
| 6,136,839 A | 10/2000 | Isakson et al. | |
| 6,207,675 B1 | 3/2001 | Carry et al. | |
| 6,919,352 B1 | 7/2005 | Chamberlain et al. | |
| 6,962,914 B1 * | 11/2005 | Gudmundsson et al. | . 514/233.2 |

FOREIGN PATENT DOCUMENTS

| | | |
|---|---|---|
| EP | 0 404 190 A1 | 6/1990 |
| EP | 0 404 190 B1 | 6/1990 |
| EP | 0 379 979 | 8/1990 |
| EP | 0 467 248 B1 | 7/1991 |
| EP | 0 497 258 A2 | 1/1992 |
| FR | 2 757 059 | 6/1998 |

(Continued)

OTHER PUBLICATIONS

Douglas, Jr. Introduction to Viral Diseases, Cecil Textbook of Medicine, 20th Edition, vol. 2, pp. 1739-1747, 1996.*

(Continued)

*Primary Examiner*—Deepak Rao
(74) *Attorney, Agent, or Firm*—Lorie Ann Morgan

(57) ABSTRACT

The present invention provides compounds of formula (I):

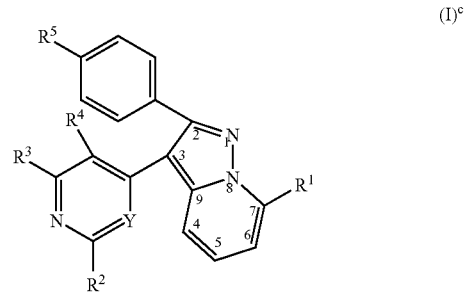

wherein all variables are as defined herein, pharmaceutical compositions containing the same, processes for preparing the same and their use as pharmaceutical agents.

25 Claims, No Drawings

FOREIGN PATENT DOCUMENTS

| WO | 0 364 204 A1 | 10/1989 |
|---|---|---|
| WO | WO 91 00092 | 1/1991 |
| WO | WO 91 19497 | 12/1991 |
| WO | WO 95 00501 | 1/1995 |
| WO | WO 96 06840 | 3/1996 |
| WO | WO 96 21667 | 7/1996 |
| WO | WO 96 31509 | 10/1996 |
| WO | WO 96 41625 | 12/1996 |
| WO | WO 96 41626 | 12/1996 |
| WO | WO 96 41645 | 12/1996 |
| WO | WO 98 56377 | 12/1998 |
| WO | WO 99 12930 | 3/1999 |
| WO | WO 99/58523 | 11/1999 |
| WO | WO 99/59585 | 11/1999 |
| WO | WO 99 64419 | 12/1999 |
| WO | WO 00/26216 | 5/2000 |
| WO | WO 00/52008 | 9/2000 |
| WO | WO 01/00615 | 1/2001 |
| WO | WO 01 14375 | 3/2001 |
| WO | WO 02 16359 | 2/2002 |
| WO | WO 02 18382 | 3/2002 |
| WO | WO 02 48147 | 6/2002 |
| WO | WO 02/048148 | 6/2002 |
| WO | WO 02 066481 | 8/2002 |
| WO | WO 03 000682 | 1/2003 |

OTHER PUBLICATIONS

Bosseray et al., PubMed Abstract (Pathol Biol (Paris) 50(8):483-92) Oct. 2002.*

Razonable et al., PubMed Abstract (Herpes. 10(3):60-5) Dec. 2003.*

Vane, J. et al. "Towards a Better Aspirin." Nature, vol. 367, Jan. 20, 1994, pp. 215-216.

Carter, J. et al. "Recently Reported Inhibitors of Cyclooxygenase-2." Exp. Opin. Ther. Patents (1998), 8(1), pp. 21-29.

Talley, JJ., "Review, Pulmonary-Allergy, Dermatological, Gastrointestinal & Arthritis, Selective Inhibitors of Cyclooxygenase-2." Exp. Opin. Ther. Patents (1997) 7(1), pp. 55-62.

Roy, P., "A New Series of Selective Cox-2 Inhibitors: 5,6-Diarylthiazolo [3,2-b][1,22,4] Triazoles," *Bioorganiz & Med. Chem. Ltrs.*, vol. 7, No. 1, 1997, pp. 57-62.

Therien, Michael, Synthesis and Biological Evaluation of 5, 6-Diarylimidazo[2.1-b]Thiazole As Selective Cox-2 Inhibitors, *Bioorganic & Med. Chem. Ltrs.*, vol. 7, No. 1, 1997, pp. 47-52.

Akahane, Atsushi, "Discovery of 6-Oxo-3-(2-Phenlypyrazolo[1,5-a]pyridin-3-yl)-1(6H)-pyridazinebutanoic Acid (FR838): A Novel Xanthine Adenosine $A_1$ Receptor Antagonist with Potent Diuretic Activity," *Journal of Medicinal Chemistry*, vol. 42, No. 5, 1999, pp. 779-783.

Talley, John J., 5 Selective Inhibitors of Cyclooxygenase-2 (COX-2) *Progress in Medicinal Chemistry*, vol. 36, (1999): pp. 201-234.

Boehm, J.C., et al. "1-Substituted 4-Aryl-5-pyridinylimidazoles: A New Class of Cytokine Suppressive Drugs with Low 5-Lipoxygenase and Cyclooxygenase Inhibitory Potency." J. Med. Chem. 1996, 39, pp. 3929-3937.

Hanson, G.J., et al. "Pulmonary-Allergy, Dermatological, Gastrointestinal & Arthritis, Inhibitors of p38 kinase." Expert Opinion Ther. Patents, 1997, 7(7):729-733.

* cited by examiner

PYRAZOLOPYRIDINYL PYRIMIDINE THERAPEUTIC COMPOUNDS

CROSS REFERENCES TO RELATED APPLICATIONS

This application is a 371 Application of PCT/US01/44231, filed 26 Nov. 2001, which claims priority to U.S. Application Ser. No. 60/255,763, filed 15 Dec. 2000 and U.S. Application Ser. No. 60/274,284, filed 8 Mar. 2001.

BACKGROUND OF THE INVENTION

The present invention relates to novel compounds, pharmaceutical formulations comprising these compounds, and the use of these compounds in therapy. More particularly, the present invention relates to compounds for the prophylaxis and treatment of herpes viral infections.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6), human herpes virus type 7 (HHV-7) and human herpes virus type 8 (HHV-8). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

Herpes simplex viruses (HSV-1 and -2) are the causative agents of herpes labialis and genital herpes. HSV infection is often characterised by extensive and debilitating lesions of the skin, mouth and/or genitals. Primary infections may be subclinical although tend to be more severe than infections in individuals previously exposed to the virus. Ocular infection by HSV can lead to keratitis or cataracts thereby endangering the host's sight. Infection in the new-born, in immunocompromised patients or penetration of the infection into the central nervous system can prove fatal. In the US alone, 40 million individuals are infected with HSV-2, a number that is expected to increase to 60 million by 2007. Over 80% of individuals infected with HSV-2 are unaware they carry and spread the virus, and of those diagnosed less than 20% received oral therapies. The net result is that less than 5% of the infected population are treated. Likewise of the 530 million individuals worldwide who carry the HSV-1 virus, 81% of the symptomatic population remain untreated. No cure exists for HSV infection, and once infected, individuals carry the virus for life in a dormant state. Reactivation of the virus from latency occurs periodically and may be triggered by stress, environmental factors, and/or suppression of the host immune system. Currently, the use of nucleoside analogs such as valaciclovir (VALTREX®) and aciclovir (ZOVIRAX®) is the standard of care for managing genital herpes virus outbreaks.

VZV is a herpes virus which causes chickenpox and shingles. Chickenpox is the primary disease produced in a host without immunity, and in young children is usually a mild illness characterised by a vesicular rash and fever. Shingles or zoster is the recurrent form of the disease which occurs in adults who were previously infected with VZV. The clinical manifestations of shingles are characterised by neuralgia and a vesicular skin rash that is unilateral and dermatomal in distribution. Spread of inflammation may lead to paralysis or convulsions. Coma can occur if the meninges become affected. VZV is of serious concern in patients receiving immunosuppressive drugs for transplant purposes or for treatment of malignant neoplasia and is a serious complication of AIDS patients due to their impaired immune system.

In common with other herpes viruses, infection with CMV leads to a lifelong association of virus and host. Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus, may give rise to retinitis, pneumonitis, gastrointestinal disorders and neurological diseases. CMV infection is also associated with cardiovascular diseases and conditions including restenosis and atheroslcerosis.

The main disease caused by EBV is acute or chronic infectious mononucleosis (glandular fever). Examples of other EBV or EBV associated diseases include lymphoproliferative disease which frequently occurs in persons with congenital or acquired cellular immune deficiency, X-linked lymphoproliferative disease which occurs namely in young boys, EBV-associated B-cell tumours, Hodgkin's disease, nasopharyngeal carcinoma, Burkitt lymphoma, non-Hodgkin lymphoma, thymomas and oral hairy leukoplakia. EBV infections have also been found in association with a variety of epithelial-cell-derived tumours of the upper and lower respiratory tracts including the lung. EBV infection has also been associated with other diseases and conditions including chronic fatigue syndrome and multiple sclerosis.

HHV-6 has been shown to be a causative agent of infantum subitum in children and of kidney rejection and interstitial pneumonia in kidney and bone marrow transplant patients, respectively, and may be associated with other diseases such as multiple sclerosis. There is also evidence of repression of stem cell counts in bone marrow transplant patients. HHV-7 is of undetermined disease aetiology.

Hepatitis B virus (HBV) is a viral pathogen of world-wide major importance. The virus is aetiologically associated with primary hepatocellular carcinoma and is thought to cause 80% of the world's liver cancer. Clinical effects of infection with HBV range from headache, fever, malaise, nausea, vomiting, anorexia and abdominal pains. Replication of the virus is usually controlled by the immune response, with a course of recovery lasting weeks or months in humans, but infection may be more severe leading to persistent chronic liver disease outlined above.

BRIEF SUMMARY OF THE INVENTION

According to a first aspect of the invention there is provided the compound of formula (I):

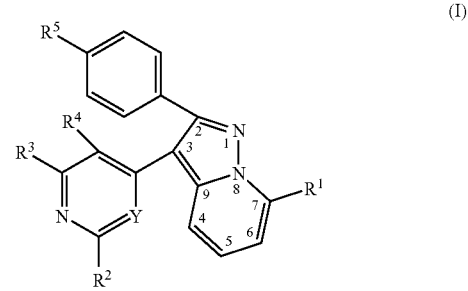

wherein:

$R^1$ is selected from the group consisting of halo, —NR$^7$R$^8$, —NR$^7$Ay, Ay, Het, —NH(CH$_2$)$_m$Het, and —NH(CH$_2$)$_l$Ay;

each $R^7$ and $R^8$ are the same or different and are independently selected from the group consisting of H, alkyl, cycloalkyl, alkenyl, cycloalkenyl, alkylhydroxy, amine, alkylamine, alkylcarboxy, alkylcarboxamide, alkyl alkoxycarbonyl, alkylthioamide, alkylsulfonyl, alkylsulfonamide, alkylether, —(CH$_2$)$_l$-cycloalkyl, —(CH$^2$)$_i$NHCOR$^9$ and —(CH$_2$)$_m$SO$_2$NHCOR$^9$;

l is 1-6;

m is 0-6;

$R^9$ is H, alkyl, cycloalkyl, alkylhydroxy, amine, alkylamine, alkylcarboxy and alkylether;

Ay is aryl;

Het is a 5- or 6-membered heterocyclic or heteroaryl group;

$R^2$ is selected from the group consisting of H, halo, alkyl, cycloalkyl, alkenyl, cycloalkenyl, —NR$^7$R$^8$, —OR$^7$, —OAy, —S(O)$_n$R$^7$, —S(O)$_n$Ay, —R$^{10}$NR$^7$R$^8$, —R$^{10}$NR$^7$Ay, Ay, Het, —NH(CH$_2$)$_m$Het and —O(CH$_2$)$_m$Het;

n is 0, 1 or 2;

$R^{10}$ is alkyl or alkenyl;

Y is N or CH;

$R^3$ and $R^4$ are each independently selected from the group consisting of H, halo, hydroxy, alkyl, alkylhydroxy, alkylamine, alkylether, —OR$^7$, —OAy, —NR$^7$R$^8$, —NR$^7$Ay, carboxy, carboxamide, —SO$_2$NHR$^9$, Het and Ay; and $R^5$ is halo;

wherein when Y is CH, $R^3$ is not —NR$^7$Ay;

and pharmaceutically acceptable salts, solvates and physiologically functional derivatives thereof.

In another aspect of the invention there is provided a pharmaceutical formulation comprising a compound of formula (I). In one embodiment, the pharmaceutical formulation further comprises a pharmaceutically acceptable carrier or diluent. In one embodiment, the pharmaceutical formulation further comprises an antiviral agent selected from the group consisting of aciclovir and valaciclovir.

In a third aspect of the invention, there is provided a method for the prophylaxis or treatment of herpes viral infections in an animal. The method comprises administering to the animal a therapeutically effective amount of a compound of formula (I) or a pharmaceutically acceptable salt, solvate of physiologically functional derivative thereof.

In a fourth aspect, there is provided a method for the treatment or prophylaxis of conditions or diseases associated with herpes viral infections in an animal. The method comprises administering to the animal a therapeutically effective amount of the compound of formula (I) or a pharmaceutically acceptable salt, solvate or physiologically functional derivative thereof.

In another aspect, there is provided a process for preparing the compound of formula (I), wherein Y is N, $R^2$ is selected from the group consisting of H, alkyl, cycloalkyl, alkenyl, cycloalkenyl, —NR$^7$R$^8$, —OR$^7$, —OAy, —S(O)$_n$R$^7$, —S(O)$_n$Ay, —R$^{10}$NR$^7$R$^8$, —R$^{10}$NR$^7$Ay, Ay, Het, —NH(CH$_2$)$_m$Het and —O(CH$_2$)$_m$Het; and $R^3$ and $R^4$ are both H. The process comprises reacting a compound of formula (IX):

with an amine of formula (X):

In another aspect, the present invention provides a process for preparing the compound of formula (I) wherein Y is N; $R^2$ is selected from the group consisting of H, alkyl, cycloalkyl, alkenyl, cycloalkenyl, —NR$^7$R$^8$, —OR$^7$, —OAy, —S(O)$_n$R$^7$, —S(O)$_n$Ay, —R$^{10}$NR$^7$R$^8$, —R$^{10}$NR$^7$Ay, Ay, Het, —NH(CH$_2$)$_m$Het and —O(CH$_2$)$_m$Het; $R^3$ is selected from the group consisting of H, alkyl, alkylhydroxy, alkylamine, alkylether, —NR$^7$R$^8$ where $R^7$ and $R^8$ are not H, —NR$^7$Ay where $R^7$ is not H, carboxy, carboxamide, —SO$_2$NHR$^9$, Het and Ay; and $R^4$ is H. The process comprises reacting a compound of formula (XVI):

with an amine of formula (X):

In another aspect, the present invention provides a process for preparing the compound of formula (I), wherein Y is N and $R^2$ is selected from the group consisting of H, alkyl, cycloalkyl, alkenyl, cycloalkenyl, —NR$^7$R$^8$, —OR$^7$, —OAy, —S(O)$_n$R$^7$, —S(O)$_n$Ay, —R$^{10}$NR$^7$R$^8$, —R$^{10}$NR$^7$Ay, Ay, Het, —NH(CH$_2$)$_m$Het and —O(CH$_2$)$_m$Het. The process comprises the steps of:

(a) reacting a compound of formula (XX):

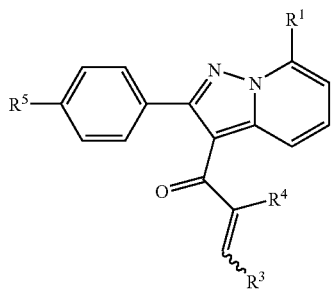

with an amine of formula (X):

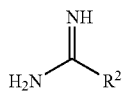

to prepare an intermediate compound; and
b) oxidizing the intermediate compound.

In another aspect, the present invention provides a process for preparing compounds of formula (I). The process comprises reacting a compound of formula (XXII):

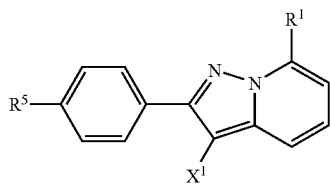

wherein $X^1$ is chloro, bromo or iodo;

with a compound of formula (XXIV):

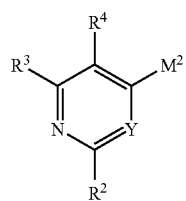

wherein $M^2$ is selected from the group consisting of —B(OH)$_2$, —B(ORa)$_2$, —B(Ra)$_2$, —Sn(Ra)$_3$, Zn-halide, ZnRa and Mg-halide, where Ra is alkyl or cycloalkyl and halide is halo.

In another aspect, the present invention provides a radiolabeled compound of formula (I) or a pharmaceutically acceptable salt, solvate or physiologically functional derivative thereof. In one embodiment, the present invention provides a tritiated compound of formula (I) or a pharmaceutically acceptable salt, solvate or physiologically functional derivative thereof.

In another aspect, the present invention provides a compound of formula (I) for use in therapy.

The present invention also provides a compound of formula (I) for use in the prophylaxis or treatment of herpes viral infections in an animal.

The present invention also provides a compound of formula (I) for use in the prophylaxis or treatment of conditions or diseases associated with herpes viral infections in an animal.

In yet another aspect, the present invention provides the use of a compound of formula (I) for the preparation of a medicament for the treatment of herpes viral infections in an animal.

The present invention also provides the use of a compound of formula (I) for the preparation of a medicament for the prophylaxis or treatment of conditions or diseases associated with herpes viral infections in an animal.

DETAILED DESCRIPTION OF THE INVENTION

As used herein, "a compound of the invention" means a compound of formula (I) or a pharmaceutically acceptable salt, solvate, or physiologically functional derivative thereof. Similarly, with respect to isolatable intermediates such as compounds of formula (IX) (XVI), (XX), and (XXII), the phrase "a compound of formula (number)" means a compound having that formula and pharmaceutically acceptable salts, solvates and physiologically functional derivatives thereof.

As used herein, the terms "alkyl" and "alkylene" refer to straight or branched hydrocarbon chains containing from 1 to 8 carbon atoms. Examples of "alkyl" as used herein include, but are not limited to, methyl, ethyl, n-propyl, n-butyl, n-pentyl, isobutyl, isopropyl, and tert-butyl. Examples of "alkylene" as used herein include, but are not limited to, methylene, ethylene, propylene, butylene, and isobutylene. The alkyl groups may be optionally substituted with alkylsulfenyl, alkylsulfinyl, alkylsulfonyl, oxo, mercapto, nitro, cyano, halo, and perfluoroalkyl. Trihalomethyl, such as trifluoromethyl, is one preferred alkyl group.

As used herein, the term "cycloalkyl" refers to a non-aromatic carbocyclic ring having from 3 to 8 carbon atoms and no carbon-carbon double bonds. "Cycloalkyl" includes by way of example cyclopropyl, cyclobutyl, cyclopentyl, cyclohexyl, cycloheptyl and cyclooctyl. "Cycloalkyl" also includes substituted cycloalkyl. The cycloalkyl may be optionally substituted with substituents selected from a group consisting of mercapto, nitro, cyano, halo, and perfluoroalkyl.

As used herein, the term "alkenyl" refers to straight or branched hydrocarbon chains containing from 2 to 8 carbon atoms and at least one and up to three carbon-carbon double bonds. Examples of "alkenyl" as used herein include, but are not limited to ethenyl and propenyl. "Alkenyl" also includes substituted alkenyl. The alkenyl groups may be optionally substituted with mercapto, nitro, cyano, halo, and perfluoroalkyl.

As used herein, the term "cycloalkenyl" refers to a non-aromatic carbocyclic ring having from 3 to 8 carbon atoms and from one to three carbon-carbon double bonds. "Cycloalkenyl" includes by way of example cyclobutenyl, cyclopentenyl, cyclohexenyl, cycloheptenyl and cyclooctenyl. "Cycloalkenyl" also includes substituted cycloalkenyl. The cycloalkenyl may be optionally substituted with substituents selected from a group consisting of mercapto, nitro, cyano, halo, and perfluoroalkyl.

As used herein, the term "alkoxy" refers to the group RaO—, where Ra is alkyl or cycloalkyl as defined above.

The term "alkylhydroxy" refers to the group —RaOH, where Ra is alkyl or cycloalkyl as defined above.

The term "alkylamine" refers to the group —RaNH$_2$, where Ra is alkyl or cycloalkyl as defined above.

The term "alkylcarboxy" refers to the group —RaC(O)OH, where Ra is alkyl or cycloalkyl as defined above.

The term "alkylether" refers to the group —RaORa, where Ra is alkyl or cycloalkyl as defined above.

The term "alkyl alkoxycarbonyl" refers to a group —Ra—C(O)—O—Ra, where Ra is alkyl or cycloalkyl as defined above.

The term "alkylsulfonamide" refers to a group —Ra—SO$_2$—NH$_2$, where Ra is alkyl or cycloalkyl as defined above.

The term "halo" or "halogen" refers to the elements fluorine, chlorine, bromine and iodine.

The term "aryl" refers to monocyclic carbocyclic groups and fused bicyclic carbocyclic groups having from 5 to 12 carbon atoms and having at least one aromatic ring. Examples of particular aryl groups include but are not limited to phenyl, and naphthyl. "Aryl" also includes substitued aryl groups. Aryl groups may be optionally substituted with substituents selected from the group consisting of halo, alkyl, alkenyl, cycloalkyl, cycloalkenyl, perfluoroalkyl, alkoxy, amino, hydroxy, alkylhydroxy, alkylamine, alkylether carboxy, carboxamide, sulfonamide, Het, amidine, cyano, nitro and azido. Phenyl and substituted phenyl are preferred aryl groups.

The term "heterocyclic" refers to a monocyclic saturated or unsaturated non-aromatic carbocyclic groups and fused bicyclic non-aromatic carbocyclic groups, having the specified number of members in a single ring and containing 1, 2, 3 or 4 heteroatoms selected from N, O and S. Examples of particular heterocyclic groups include but are not limited to tetrahydrofuran, dihydropyran, tetrahydropyran, pyran, oxetane, thietane, 1,4-dioxane, 1,3-dioxane, 1,3-dioxalane, piperidine, piperazine, tetrahydropyrimidine, pyrrolidine, morpholine, thiomorpholine, thiazolidine, oxazolidine, tetrahydrothiopyran, tetrahydrothiophene, and the like. "Heterocycle" also includes substituted heterocycle. The heterocyclic group may be optionally substituted with substituents selected from a group consisting of halo, alkyl, alkenyl, cycloalkyl, cycloalkenyl, perfluoroalkyl, alkoxy, amino, hydroxy, alkylhydroxy, alkylamine alkylether, carboxy, carboxamide, sulfonamide, Het, amidine, cyano, nitro an azido. Preferred heterocyclic groups include but are not limited to pyrrolidine, piperidine, morpholine, thiomorpholine and piperazine.

The term "heteroaryl" refers to aromatic monocyclic heterocyclic groups and aromatic fused bicyclic groups having the specified number of members and containing 1, 2, 3, or 4 heteroatoms selected from N, O and S. Examples of particular heteroaryl groups include but are not limited to furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole. "Heteroaryl" also includes substituted heteroaryl groups. The heteroaryl group may be optionally substituted with substituents selected from a group consisting of halo, alkyl, alkenyl, cycloalkyl, cycloalkenyl, perfluoroalkyl, alkoxy, amino, hydroxy, alkylhydroxy, alkylamine, alkylether, carboxy, carboxamide, sulfonamide, Het, amidine, cyano, nitro and azido. Preferred heteroaryl groups include but are not limited to pyridine, furan, thiophene, pyrrole, imidazole, pyrazole, and pyrimidine.

As used herein, the term "optionally" means that the subsequently described event(s) may or may not occur, and includes both event(s) which occur and events that do not occur.

The present invention provides compounds of formula (I):

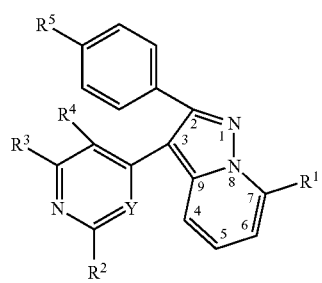

wherein:

R$^1$ is selected from the group consisting of halo, —NR$^7$R$^8$, Ay, —NR$^7$Ay, Het, —NH(CH$_2$)$_m$Het, and —NH(CH$_2$)$_l$Ay;

each R$^7$ and R$^8$ are the same or different and are independently selected from the group consisting of H, alkyl, cycloalkyl, alkenyl, cycloalkenyl, alkylhydroxy, amine, alkylamine, alkylcarboxy, alkylcarboxamide, alkyl alkoxycarbonyl, alkylthioamide, alkylsulfonyl, alkylsulfonamide, alkylether, —(CH$_2$)$_l$-cycloalkyl, —(CH$^2$)$_l$NHCOR$^9$ and —(CH$_2$)$_m$SO$_2$NHCOR$^9$;

l is 1-6;

m is 0-6;

R$^9$ is H, alkyl, cycloalkyl, alkylhydroxy, amine, alkylamine, alkylcarboxy and alkylether;

Ay is aryl;

Het is a 5- or 6-membered heterocyclic or heteroaryl group;

R$^2$ is selected from the group consisting of H, halo, alky, cyloalkyl, alkenyl, cycloalkenyl, —NR$^7$R$^8$, —OR$^7$, —OAy, —S(O)$_n$R$^7$, —S(O)$_n$Ay, —R$^{10}$NR$^7$R$^8$, —R$^{10}$NR$^7$Ay, Ay, Het, —NH(CH$_2$)$_m$Het and —O(CH$_2$)$_m$Het;

n is 0, 1 or 2;

R$^{10}$ is alkyl or alkenyl;

Y is N or CH;

R$^3$ and R$^4$ are each independently selected from the group consisting of H, halo, hydroxy, alkyl, alkylhydroxy, alkylamine, alkylether, —OR$^7$, —OAy, —NR$^7$R$^8$, —NR$^7$Ay, carboxy, carboxamide, —SO$_2$NHR$^9$, Het and Ay; and R$^5$ is halo;

wherein when Y is CH, R$^3$ is not —NR$^7$Ay;

and pharmaceutically acceptable salts, solvates and physiologically functional derivatives thereof.

Preferred compounds of formula (I) include those compounds defined wherein at least one of R$^1$ and R$^2$ contain an aryl, heterocyclic or heteroaryl moiety. The groups of Ay, —OAy, —NR$^7$Ay, —R$^{10}$NR$^7$Ay, —S(O)$_n$Ay, Het, —NH(CH$_2$)$_m$Het, —NH(CH$_2$)$_l$Ay, and —O(CH$_2$)$_m$Het are some examples of groups containing an aryl, heterocyclic or heteroaryl moiety. To illustrate, in such embodiments, if R$^2$ is defined as H, halo, alkyl, cycloalkyl, alkenyl, cycloalkenyl, —NR$^7$R$^8$, —OR$^7$, —S(O)$_n$R$^7$ or —R$^{10}$NR$^7$R$^8$; then R$^1$ is selected from the group consisting of Ay, —NR$^7$Ay, Het, —NH(CH$_2$)$_m$Het, and —NH(CH$_2$)$_i$Ay; and if R$^1$ is halo or —NR$^7$R$^8$; then R$^2$ is selected from the group consisting of Ay, —OAy, —R$^{10}$NR$^7$Ay, —S(O)$_n$Ay, Het, —NH(CH$_2$)$_m$Het, and —O(CH$_2$)$_m$Het. In one embodiment, compounds of the present invention include those compounds defined wherein at least one of R$^1$ and R$^2$ contain a heterocyclic or heteroaryl moiety such as Het, —NH(CH$_2$)$_m$Het and —O(CH$_2$)$_m$Het.

Another class of compounds of formula (I) include those compounds defined wherein neither R$^1$ nor R$^2$ contain an aryl, heterocyclic or heteroaryl moiety. In such embodiments, R$^1$ is preferably halo or —NR$^7$R$^8$, and R$^2$ is preferably selected from the group consisting of H, halo, alkyl, cycloalkyl, alkenyl, cycloalkenyl, —NR$^7$R$^8$, —OR$^7$, —S(O)$_n$R$^7$, and —R$^{10}$NR$^7$R$^8$. More preferably, neither of R$^1$ and R$^2$ contain a heterocyclic or heteroaryl moiety, but may contain an aryl moiety.

In one preferred class of compounds of formula (I), Y is CH. In another preferred class of compounds of formula (I), Y is N. According to one preferred embodiment, when Y is CH, R$^3$ is not —NR$^7$Ay.

Preferably, R$^1$ is selected from the group consisting of —NR$^7$R$^8$, Ay, —NR$^7$Ay, Het, —NH(CH$_2$)$_m$Het, and —NH(CH$_2$)$_i$Ay, or any subset thereof. More preferably, R$^1$ is selected from the group consisting of —NR$^7$R$^8$, Het and —NH(CH$_2$)$_m$Het, or any subset thereof. Particularly preferred compounds of formula (I) are defined wherein R$^1$ is —NR$^7$R$^8$.

In particular, R$^1$ is preferably selected from the group consisting of Cl, —NH$_2$, —NHalkyl, —NHcycloalkyl, —N(alkyl)(alkyl), Het, —Nalkyl-O-alkyl, and —NHAy, or any subset thereof. Specific examples of some prefered R$^1$ groups are selected from the group consisting of Cl, —NH$_2$, —NH-methyl, —N(CH$_3$)$_2$, —NH-cyclopentyl, —NH-cyclopropyl, —NH-propyl, —NH-isopropyl, —NH-n-butyl, —NH-phenyl, —NH(CH$_2$)$_2$OCH$_3$, and pyrrolidine, or any subset thereof. In one embodiment R$^1$ is —NH-cyclopentyl. In one embodiment R$^1$ is —NH-n-butyl. In one embodiment R$^1$ is —NH-cyclopropyl. In one embodiment R$^1$ is pyrrolidine.

R$^2$ is preferably selected from the group consisting of —NR$^7$R$^8$, —OR$^7$, —OAy, —S(O)$_n$R$^7$, —S(O)$_n$Ay, —R$^{10}$NR$^7$R$^8$, —R$^{10}$NR$^7$Ay, Ay, Het, —NH(CH$_2$)$_m$Het and —O(CH$_2$)$_m$Het, or any subset thereof. More preferably, R$^2$ is selected from the group consisting of —NR$^7$R$^8$, —R$^{10}$NR$^7$R$^8$, Ay and Het or any subset thereof. Particularly preferred compounds of formula (I) are defined where R$^2$ is selected from the group consisting of —NR$^7$R$^8$ and Het, or any subset thereof.

More particularly, preferred embodiments of the present invention include compounds of formula (I) wherein R$^2$ is selected from the group consisting of —NH$_2$, —NH-alkyl, —NH-cycloalkyl, Het and —NH-alkyl-Het. Particularly preferred embodiments include those compounds of formula (I) wherein R$^2$ is —NH$_2$, —NH-propyl, —NH-isopropyl, —NH-cyclopropyl, —NH-butyl, —NH-isobutyl, —NH-cyclobutyl, —NH-cyclopentyl, —NH-cyclohexyl, —NH(CH$_2$)$_2$OCH$_3$, and pyrrolidine (e.g., pyrrolidine bonded through N).

Preferably, R$^7$ and R$^8$ are each the same or different and are independently selected from the group consisting of H, alkyl, cycloalkyl, alkylhydroxy, amine, alkylamine, and alkylcarboxy, or any subset thereof. More preferably, R$^7$ and R$^8$ are each the same or different and are independently selected from the group consisting of H, alkyl and cycloalkyl, or any subset thereof.

Preferably, R$^3$ and R$^4$ are each the same or different and are each independently selected from the group consisting of H, hydroxy, alkyl, alkylhydroxy, alkylamine, alkylether, —NR$^7$R$^8$, carboxy and Ay, or any subset thereof. More preferably, R$^3$ and R$^4$ are each the same or different and are each independently selected from the group consisting of H, alkyl, alkylhydroxy, alkylamine, alkylether or Ay, or any subset thereof.

More particularly, R$^3$ and R$^4$ are each the same or different and are each independently selected from the group consisting of H, F, Cl, Br, methyl, ethyl, propyl, O-methyl, O-ethyl, O-isopropyl, —CH$_2$—O-methyl, —NH$_2$, —NH(alkyl), —N(alkyl)(alkyl), —CH$_2$—NH$_2$, —CH$_2$—NH(alkyl), —CH$_2$—N(alkyl)(alkyl), —CO$_2$H, —CO$_2$-methyl and phenyl, or any subset thereof. More preferably, R$^3$ and R$^4$ are each the same or different and are each independently selected from the group consisting of H, F, Cl, Br, methyl, ethyl, propyl, O-methyl, O-ethyl, O-isopropyl, and —NH$_2$, —NH(alkyl), —N(alkyl)(alkyl), or any subset thereof.

In one preferred embodiment, R$^3$ is H or alkyl; more preferably H.

In one preferred embodiment, R$^4$ is H or alkyl; more preferably H.

Preferably, R$^5$ is fluoro.

It is to be understood that the present invention includes all combinations of the particular and preferred groups defined hereinabove.

Preferred compounds of formula (I) include but are not limited to:

N-Cyclopentyl-3-[2-(cyclopentylamino)-4-pyrimidinyl]-2-(4-fluorophenyl)pyrazolo[1,5-α]pyridin-7-amine;

2-(4-Bromophenyl)-N-butyl-3-[2-(butylamino)-4-pyrimidinyl]pyrazolo[1,5-α]pyridin-7-amine;

N-Butyl-3-[2-(butylamino)-4-pyrimidinyl]-2-(4-fluorophenyl)pyrazolo[1,5-α]pyridin-7-amine;

N-Butyl-3-[2-(cyclopropylamino)-4-pyrimidinyl]-2-(4-fluorophenyl)pyrazolo[1,5-α]pyridin-7-amine;

N-Butyl-2-(4-fluorophenyl)-3-[2-(1-pyrrolidinyl)-4-pyrimidinyl]pyrazolo[1,5-α]pyridin-7-amine;

N-Butyl-3-[2-(cyclopentylamino)-4-pyrimidinyl]-2-(4-fluorophenyl)pyrazolo[1,5-α]pyridin-7-amine;

4-[7-Chloro-2-(4-fluorophenyl)pyrazolo[1,5-α]pyridin-3-yl]-N-cyclopentyl-6-methyl-2-pyrimidinamine;

N-Cyclopentyl-3-[2-(cyclopentylamino)-6-methyl-4-pyrimidinyl]-2-(4-fluorophenyl)pyrazolo[1,5-α]pyridin-7-amine;

2-(4-Bromophenyl)-N-butyl-3-[2-(1-pyrrolidinyl)-4-pyrimidinyl]pyrazolo[1,5-α]pyridin-7-amine;

2-(4-Bromophenyl)-N-butyl-3-[2-(cyclopentylamino)-4-pyrimidinyl]pyrazolo[1,5-α]pyridin-7-amine;

N-Cyclopentyl-3-[2-(dimethylamino)-4-pyrimidinyl]-2-(4-fluorophenyl)pyrazolo[1,5-α]pyridin-7-amine;

3-(2-Amino-4-pyrimidinyl)-N-cylopentyl-2-(4-fluorophenyl)pyrazolo[1,5-α]pyridin-7-amine;

N-Cyclopentyl-2-(4-fluorophenyl)-3-(2-{[3-(4-morpholinyl)propyl]amino}-4-pyrimidinyl)pyrazolo[1,5-α]pyridin-7-amine;

N-Cyclopentyl-4-[2-(4-fluorophenyl)-7-hydrazinopyrazolo[1,5-α]pyridin-3-yl]-6-methyl-2-pyrimidinamine;

N-Cyclopentyl-4-[2-(4-fluorophenyl)-7-(4-methyl-1-piperazinyl)pyrazolo[1,5-α]pyridin-3-yl]-6-methyl-2-pyrimidinamine;

N-Cyclopentyl-3-{2-(cyclopentylamino)-6-[(tetrahydro-2H-pyran-2-yloxy)methyl]-4-pyrimidinyl}-2-(4-fluorophenyl)pyrazolo[1,5-α]pyridin-7-amine;

[6-[7-Chloro-2-(4-fluorophenyl)pyrazolo[1,5-α]pyridin-3-yl]-2-(cyclopentylamino)-4-pyrimidinyl]methanol;

[{4-[7-(Cyclopentylamino)-2-(4-fluorophenyl)pyrazolo[1,5-α]pyridin-3-yl]-2-pyrimidinyl}(methyl)amino]acetic acid;

N-Cyclopentyl-4-[2-(4-fluorophenyl)-7-(4-methyl-1-piperazinyl)pyrazolo[1,5-α]pyridin-3-yl]-6-phenyl-2-pyrimidinamine hydrochloride;

$N^1$-[3-[2-(Cyclopentylamino)-6-phenyl-4-pyrimidinyl]-2-(4-fluorophenyl)pyrazolo[1,5-α]pyridin-7-yl]-1,2-ethanediamine;

3-[2-(Cyclopentylamino)-4-pyrimidinyl]-2-(4-fluorophenyl)pyrazolo[1,5-α]pyridin-7-amine;

{2-(Cyclopentylamino)-6-[7-(cyclopentylamino)-2-(4-fluorophenyl)pyrazolo[1,5-α]pyridin-3-yl]-4-pyrimidinyl}methanol;

3-[2-(Cyclopentylamino)-4-pyrimidinyl]-2-(4-fluorophenyl)-N-(4-methoxyphenyl)-pyrazolo[1,5-α]pyridin-7-amine;

Methyl {[3-[2-(cyclopentylamino)-6-methyl-4-pyrimidinyl]-2-(4-fluorophenyl)pyrazolo[1,5-α]pyridin-7-yl]amino}acetate;

{[3-[2-(Cyclopentylamino)-6-methyl-4-pyrimidinyl]-2-(4-fluorophenyl)pyrazolo[1,5-α]pyridin-7-yl]amino}acetic acid;

4-[7-Chloro-2-(4-fluorophenyl)pyrazolo[1,5-α]pyridin-3-yl]-N-cyclopentyl-2-pyrimidinamine;

6-[7-Chloro-2-(4-fluorophenyl)pyrazolo[1,5-α]pyridin-3-yl]-2-(cyclopentylamino)-4-pyrimidinecarboxylic acid;

N-Cyclopentyl-2-(4-fluorophenyl)-3-(4-pyridinyl)pyrazolo[1,5-α]pyridin-7-amine;

N-Cyclopentyl-3-[2-(cyclopentylamino)-4-pyridinyl]-2-(4-fluorophenyl)pyrazolo[1,5-α]pyridin-7-amine;

N-Cyclopentyl-2-(4-fluorophenyl)-3-(2-hydrazino-4-pyridinyl)pyrazolo[1,5-α]pyridin-7-amine;

N-Cyclopentyl-4-[2-(4-fluorophenyl)-7-(1-pyrrolidinyl)pyrazolo[1,5-α]pyridin-3-yl]-2-pyrimidinamine;

4-[2-(4-Fluorophenyl)-7-(1-pyrrolidinyl)pyrazolo[1,5-α]pyridin-3-yl]-N,N-dimethyl-2-pyrimidinamine;

3-[2-(Butylamino)-4-pyrimidinyl]-N-cyclopropyl-2-(4-fluorophenyl)pyrazolo[1,5-α]pyridin-7-amine;

3-[2-(Butylamino)-4-pyrimidinyl]-2-(4-fluorophenyl)-N,N-dimethylpyrazolo[1,5-α]pyridin-7-amine;

N-Butyl-4-[2-(4-fluorophenyl)-7-(4-methyl-1-piperazinyl)pyrazolo[1,5-α]pyridin-3-yl]-2-pyrimidinamine;

N-Butyl-4-[2-(4-fluorophenyl)-7-(4-morpholinyl)pyrazolo[1,5-α]pyridin-3-yl]-2-pyrimidinamine;

N-Butyl-2-(4-fluorophenyl)-3-[2-(methylsulfinyl)-4-pyrimidinyl]pyrazolo[1,5-α]pyridin-7-amine;

3-({4-[7-(Butylamino)-2-(4-fluorophenyl)pyrazolo[1,5-α]pyridin-3-yl]-2-pyrimidinyl}amino)-1-propanol;

3-[2-(Allylamino)-4-pyrimidinyl]-N-butyl-2-(4-fluorophenyl)pyrazolo[1,5-α]pyridin-7-amine;

N-Butyl-2-(4-fluorophenyl)-3-[2-(4-morpholinyl)-4-pyrimidinyl]pyrazolo[1,5-α]pyridin-7-amine;

2-(4-{4-[7-(Butylamino)-2-(4-fluorophenyl)pyrazolo[1,5-α]pyridin-3-yl]-2-pyrimidinyl}-1-piperazinyl)ethanol;

N-Butyl-2-(4-fluorophenyl)-3-{2-[4-(2-methoxyethyl)-1-piperazinyl]-4-pyrimidinyl}pyrazolo[1,5-α]pyridin-7-amine;

N-Butyl-2-(4-fluorophenyl)-3-{2-[(2-pyridinylmethyl)amino]-4-pyrimidinyl}pyrazolo[1,5-α]pyridin-7-amine;

N-Butyl-2-(4-fluorophenyl)-3-(2-{[3-(1H-imidazol-1-yl)propyl]amino}-4-pyrimidinyl)pyrazolo[1,5-α]pyridin-7-amine;

N-Butyl-2-(4-fluorophenyl)-3-(2-{[2-(4-morpholinyl)ethyl]amino}-4-pyrimidinyl)pyrazolo[1,5-α]pyridin-7-amine;

N-Butyl-2-(4-fluorophenyl)-3-{2-[2-(4-morpholinyl)ethoxy]-4-pyrimidinyl}pyrazolo-[1,5-α]pyridin-7-amine;

3-[2-(Butylamino)-4-pyrimidinyl]-2-(4-fluorophenyl)-N-[2-(4-morpholinyl)ethyl]-pyrazolo[1,5-α]pyridin-7-amine;

3-[2-(Butylamino)-4-pyrimidinyl]-2-(4-fluorophenyl)-N-(2-methoxyethyl)pyrazolo[1,5-α]pyridin-7-amine;

3-[2-(Butylamino)-4-pyrimidinyl]-2-(4-fluorophenyl)-N-methylpyrazolo[1,5-α]-pyridin-7-amine;

4-[7-Chloro-2-(4-fluorophenyl)pyrazolo[1,5-α]pyridin-3-yl]-N-cyclopentyl-6-[(dimethylamino)methyl]-2-pyrimidinamine;

N-Cyclopentyl-3-{2-(cyclopentylamino)-6-[(dimethylamino)methyl]-4-pyrimidinyl}-2-(4-fluorophenyl)pyrazolo[1,5-α]pyridin-7-amine;

4-[7-Chloro-2-(4-fluorophenyl)pyrazolo[1,5-α]pyridin-3-yl]-N-cyclopentyl-5-methyl-2-pyrimidinamine;

N-Cyclopentyl-3-[2-(cyclopentylamino)-5-methyl-4-pyrimidinyl]-2-(4-fluorophenyl)pyrazolo[1,5-α]pyridin-7-amine;

N-Allyl-3-[2-(butylamino)-4-pyrimidinyl]-2-(4-fluorophenyl)-pyrazolo[1,5-α]pyridin-7-amine;

3-[2-(Butylamino)-4-pyrimidinyl]-2-(4-fluorophenyl)-N-propylpyrazolo[1,5-α]pyridin-7-amine;

7-Chloro-2-(4-fluorophenyl)-3-pyridin-4-ylpyrazolo[1,5-α]pyridine;

N-[2-(4-Fluorophenyl)-3-(4-pyridinyl)pyrazolo[1,5-α]pyridin-7-yl]-N-[2-(1-methyl-2-pyrrolidinyl)ethyl]amine;

2-(4-Fluorophenyl)-N-methyl-3-(4-pyridinyl)pyrazolo[1,5-α]pyridin-7-amine;

N,N-Diethyl-2-(4-fluorophenyl)-3-(4-pyridinyl)pyrazolo[1,5-α]pyridin-7-amine;

2-(4-Fluorophenyl)-7-iodo-3-pyridin-4-ylpyrazolo[1,5-α]pyridine;

7-Bromo-2-(4-fluorophenyl)-3-pyridin-4-ylpyrazolo[1,5-α]pyridine;

N-Butyl-2-(4-fluorophenyl)-3-pyridin-4-ylpyrazolo[1,5-α]pyridin-7-amine;

2-(4-Fluorophenyl)-7-(1H-imidazol-1-yl)-3-pyridin-4-ylpyrazolo[1,5-α]pyridine;

2-(4-Fluorophenyl)-3,7-bis(2-fluoropyridin-4-yl)pyrazolo[1,5-α]pyridine;

N-{4-[3-{2-[(3-Aminopropyl)amino]pyridin-4-yl}-2-(4-fluorophenyl)pyrazolo[1,5-α]pyridin-7-yl]pyridin-2-yl}propane-1,3-diamine;

4-[7-Chloro-2-(4-fluorophenyl)pyrazolo[1,5-α]pyridin-3-yl]-N-propylpyridin-2-amine;

N-Butyl-4-[7-chloro-2-(4-fluorophenyl)pyrazolo[1,5-α]pyridin-3-yl]pyridin-2-amine;

N-Butyl-2-(4-fluorophenyl)-3-[2-(2,2,2-trifluoroethoxy)pyrimidin-4-yl]pyrazolo[1,5-α]pyridin-7-amine;

2-(4-Fluorophenyl)-7-pyrrolidin-1-yl-3-(2-pyrrolidin-1-ylpyrimidin-4-yl)pyrazolo[1,5-α]pyridine;

3-[(4-{2-(4-Fluorophenyl)-7-[(3-hydroxypropyl)amino]pyrazolo[1,5-α]pyridin-3-yl})pyrimidin-2-yl)amino]propan-1-ol;

N-Cyclohexyl-3-[2-(cyclohexylamino)pyrimidin-4-yl]-2-(4-fluorophenyl)pyrazolo[1,5-α]pyridin-7-amine;

3-[2-(Cyclopentylamino)-6-methylpyrimidin-4-yl]-2-(4-fluorophenyl)pyrazolo[1,5-α]pyridin-7-amine;

7-Chloro-2-(4-fluorophenyl)-3-(2-phenylpyrimidin-4-yl)pyrazolo[1,5-α]pyridine;

6-[7-Chloro-2-(4-fluorophenyl)pyrazolo[1,5-α]pyridin-3-yl]-N-cyclopentyl-2-(cyclopentylamino)pyrimidine-4-carboxamide;

N-Cyclopentyl-2-(cyclopentylamino)-6-[7-(cyclopentylamino)-2-(4-fluorophenyl)pyrazolo[1,5-α]pyridin-3-yl]pyrimidine-4-carboxamide;

7-Chloro-3-(2-cyclopropylpyrimidin-4-yl)-2-(4-fluorophenyl)pyrazolo[1,5-α]pyridine;

7-Chloro-2-(4-fluorophenyl)-3-(2-isopropylpyrimidin-4-yl) pyrazolo[1,5-α]pyridine;

N-Butyl-4-[2-(4-fluorophenyl)-7-(2-furyl)pyrazolo[1,5-α] pyridin-3-yl]pyrimidin-2-amine;

4-[7-Chloro-2-(4-fluorophenyl)pyrazolo[1,5-α]pyridin-3-yl]-N-cyclopropylpyrimidin-2-amine;

2-(4-Chlorophenyl)-N-cyclopentyl-3-[2-(cyclopentylamino)-4-pyrimidinyl]pyrazolo[1,5-α]pyridin-7-amine;

N-Cyclopentyl-3-[2-(dimethylamino)-6-methylpyrimidin-4-yl]-2-(4-fluorophenyl)pyrazolo[1,5-α]pyridin-7-amine;

N-Cyclopentyl-3-[2-(cyclopentylamino)-6-phenylpyrimidin-4-yl]-2-(4-fluorophenyl)pyrazolo[1,5-α]pyridin-7-amine;

N-Cyclopentyl-6-[2-(4-fluorophenyl)-7-(methylthio)pyrazolo[1,5-α]pyridin-3-yl]pyrimidin-4-amine; and N-cyclopentyl-3-[6-(cyclopentylamino)pyrimidin-4-yl]-2-(4-fluorophenyl)pyrazolo[1,5-α]pyridin-7-amine and pharmaceutically acceptable salts, solvates and physiologically functional derivatives thereof.

Particularly preferred compounds of formula (I) include but are not limited to:

N-cyclopentyl-3-[2-(cyclopentylamino)-4-pyrimidinyl]-2-(4-fluorophenyl)pyrazolo[1,5-α]pyridin-7-amine;

2-(4-Bromophenyl)-N-butyl-3-[2-(butylamino)-4-pyrimidinyl]pyrazolo-[1,5-α]pyridin-7-amine;

N-Butyl-3-[2-(butylamino)-4-pyrimidinyl]-2-(4-fluorophenyl)pyrazolo-[1,5-α]pyridin-7-amine;

N-Butyl-3-[2-(cyclopropylamino)-4-pyrimidinyl]-2-(4-fluorophenyl)-pyrazolo[1,5-α]pyridin-7-amine;

N-Butyl-3-[2-(cyclopentylamino)-4-pyrimidinyl]-2-(4-fluorophenyl)pyrazolo[1,5-α]pyridin-7-amine;

N-Cyclopentyl-3-[2-(cyclopentylamino)-6-methyl-4-pyrimidinyl]-2-(4-fluorophenyl)pyrazolo[1,5-α]pyridin-7-amine;

N-Cyclopentyl-3-[2-(dimethylamino)-4-pyrimidinyl]-2-(4-fluorophenyl)pyrazolo[1,5-α]pyridin-7-amine;

3-(2-Amino-4-pyrimidinyl)-N-cyclopentyl-2-(4-fluorophenyl)pyrazolo-[1,5-α]pyridin-7-amine;

3-[2-(Cyclopentylamino)-4-pyrimidinyl]-2-(4-fluorophenyl)pyrazolo[1,5-α]pyridin-7-amine;

3-[2-(Cyclopentylamino)-4-pyrimidinyl]-2-(4-fluorophenyl)-N-(4-methoxyphenyl)pyrazolo[1,5-α]pyridin-7-amine;

N-Cyclopentyl-3-[2-(cyclopentylamino)-4-pyridinyl]-2-(4-fluorophenyl)pyrazolo[1,5-α]pyridin-7-amine;

N-Cyclopentyl-4-[2-(4-fluorophenyl)-7-(1-pyrrolidinyl) pyrazolo[1,5-α]pyridin-3-yl]-2-pyrimidinamine;

3-[2-(Butylamino)-4-pyrimidinyl]-N-cyclopropyl-2-(4-fluorophenyl)pyrazolo[1,5-α]pyridin-7-amine;

3-[2-(Butylamino)-4-pyrimidinyl]-2-(4-fluorophenyl)-N,N-dimethylpyrazolo[1,5-α]pyridin-7-amine;

N-Butyl-4-[2-(4-fluorophenyl)-7-(4-methyl-1-piperazinyl) pyrazolo[1,5-α]pyridin-3-yl]-2-pyrimidinamine;

N-Butyl-4-[2-(4-fluorophenyl)-7-(4-morpholinyl)pyrazolo [1,5-α]pyridin-3-yl]-2-pyrimidinamine;

3-[2-(Allylamino)-4-pyrimidinyl]-N-butyl-2-(4-fluorophenyl)pyrazolo-[1,5-α]pyridin-7-amine;

3-[2-(Butylamino)-4-pyrimidinyl]-2-(4-fluorophenyl)-N-[2-(4-morpholinyl)ethyl]pyrazolo[1,5-α]pyridin-7-amine;

3-[2-(Butylamino)-4-pyrimidinyl]-2-(4-fluorophenyl)-N-(2-methoxyethyl)pyrazolo[1,5-α]pyridin-7-amine;

N-Cyclopentyl-3-[2-(cyclopentylamino)-5-methyl-4-pyrimidinyl]-2-(4-fluorophenyl)pyrazolo[1,5-α]pyridin-7-amine;

N-Allyl-3-[2-(butylamino)-4-pyrimidinyl]-2-(4-fluorophenyl)-pyrazolo[1,5-α]pyridin-7-amine;

N-[2-(4-Fluorophenyl)-3-(4-pyridinyl)pyrazolo[1,5-α]pyridin-7-yl]-N-[2-(1-methyl-2-pyrrolidinyl)ethyl]amine;

N-Butyl-4-[2-(4-fluorophenyl)-7-(2-furyl)pyrazolo[1,5-α] pyridin-3-yl]pyrimidin-2-amine; and 2-(4-Chlorophenyl)-N-cyclopentyl-3-[2-(cyclopentylamino)-4-pyrimidinyl]pyrazolo[1,5-α]pyridin-7-amine and pharmaceutically acceptable salts, solvates and physiologically functional derivatives thereof.

It will be appreciated by those skilled in the art that the compounds of the present invention may also be utilized in the form of a pharmaceutically acceptable salt or solvate thereof. The pharmaceutically acceptable salts of the compounds of formula (I) include conventional salts formed from pharmaceutically acceptable inorganic or organic acids or bases as well as quaternary ammonium salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts.

The term "solvate" as used herein refers to a complex of variable stoichiometry formed by a solute (a compound of formula (I)) and a solvent. Solvents, by way of example, include water, methanol, ethanol, or acetic acid. Hereinafter, reference to a compound of formula (I) is to the amorphous form of that compound, unless another form or solvate thereof is specified.

The term "physiologically functional derivative" as used herein refers to any pharmaceutically acceptable derivative of a compound of the present invention, for example, an ester or an amide, which upon administration to a mammal, such as a human, is capable of providing (directly or indirectly) such a compound or an active metabolite thereof. Such derivatives are clear to those skilled in the art, without undue experimentation, and with reference to the teaching of Burger's Medicinal Chemistry And Drug Discovery, 5th Edition, Vol 1: Principles And Practice.

Processes for preparing pharmaceutically acceptable salts, solvates and physiologically functional derivatives of the compounds of formula (I) are conventional in the art. See, e.g., Burger's Medicinal Chemistry And Drug Discovery 5th Edition, Vol 1: Principles And Practice.

As will be apparent to those skilled in the art, in the processes descibed below for the preparation of compounds of formula (I), certain intermediates (including but not limited to compounds of formula (IX), (XVI), (XX), (XXII), (XXII-A) and (XXII-B), may be in the form of pharmaceutically acceptable salts, solvates or physiologically functional derivatives of the compound. Those terms as applied to any intermediate employed in the process of preparing compounds of formula (I) have the same meanings as noted above with respect to compounds of formula (I). Processes for preparing pharmaceutically acceptable salts, solvates and physiologically functional derivatives of such intermediates are known in the art and are analogous to the process for preparing pharmaceutically acceptable salts, solvates and physiologically functional derivatives of the compounds of formula (I).

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centers are inverted. Likewise, it is understood that compounds of formula (I) may exist in tautomeric forms other than that shown in the formula and these are also included within the scope of the present invention.

The present invention further provides compounds of formula (I) for use in medical therapy, e.g. in the treatment or prophylaxis, including suppression of recurrence of symptoms, of a viral disease in an animal, e.g. a mammal such as a human. The compounds of formula (I) are especially useful for the treatment or prophylaxis of viral diseases such as herpes viral infections. Herpes viral infections include, for example, herpes simplex virus 1 (HSV-1), herpes simplex virus 2 (HSV-2), cytomegalovirus (CMV), Epstein Barr virus (EBV), herpes zoster virus (HZV), human herpes virus 6 (HHV-6), human herpes virus 7 (HHV-7), and human herpes virus 8 (HHV-8). Compounds of the invention are also useful in the treatment or prophylaxis of the symptoms or effects of herpes virus infections.

The compounds of the invention are useful in the treatment or prophylaxis of conditions or diseases associated with herpes virus infections, particularly conditions or diseases associated with latent herpes virus infections in an animal, e.g., a mammal such as a human. By conditions or diseases associated with herpes viral infections is meant a condition or disease, excluding the viral infection per se, which results from the presence of the viral infection, such as chronic fatigue syndrome which is associated with EBV infection; and multiple sclerosis which has been associated with herpes viral infections such as EBV and HHV-6. Further examples of such conditions or diseases are described in the background section above.

In addition to those conditions and diseases, the compounds of the present invention may also be used for the treatment or prophylaxis of cardiovascular diseases and conditions associated with herpes virus infections, in particular atherosclerosis, coronary artery disease and restenosis and specifically restenosis following angioplasty (RFA). Restenosis is the narrowing of the blood vessels which can occur after injury to the vessel wall, for example injury caused by balloon angioplasty or other surgical and/or diagnostic techniques, and is characterized by excessive proliferation of smooth muscle cells in the walls of the blood vessel treated. It is thought that in many patients suffering from RFA, viral infection, particularly by CMV and/or HHV-6 of the patient plays a pivotal role in the proliferation of the smooth muscle cells in the coronary vessel treated. Restenosis can occur following a number of surgical and/or diagnostic techniques, for example, transplant surgery, vein grafting, coronary by-pass grafting and, most commonly following angioplasty.

There is evidence from work done both in vitro and in vivo, indicating that restenosis is a multifactorial process. Several cytokines and growth factors, acting in concert, stimulate the migration and proliferation of vascular smooth muscle cells (SMC) and production of extracellular matrix material, which accumulate to occlude the blood vessel. In addition growth suppressors act to inhibit the proliferation of SMC's and production of extracellular matrix material.

In addition, compounds of formula (I) may be useful in the treatment or prophylaxis of hepatitis B and hepatitis C viruses, human papilloma virus (HPV) and HIV.

The present invention provides a method for the treatment or prophylaxis of a viral infection in an animal such as a mammal (e.g., a human), particularly a herpes viral infection, which comprises administering to the animal a therapeutically effective amount of the compound of formula (I).

As used herein, the term "prophylaxis" refers to the complete prevention of infection, the prevention of occurrence of symptoms in an infected subject, or a decrease in severity or frequency of symptoms of viral infection, condition or disease in the subject.

As used herein, the term "treatment" refers to the partial or total elimination of symptoms or decrease in severity of symptoms of viral infection, condition or disease in the subject, or the elimination or decrease of viral presence in the subject.

As used herein, the term "therapeutically effective amount" means an amount of a compound of formula (I) which is sufficient, in the subject to which it is administered, to treat or prevent the stated disease, condition or infection. For example, a therapeutically effective amount of a compound of formula (I) for the treatment of a herpes virus infection is an amount sufficient to treat the herpes viral infection in the subject.

The present invention also provides a method for the treatment or prophylaxis of conditions or diseases associated with herpes viral infections in an animal such as a mammal (e.g., a human), which comprises administering to the animal a therapeutically effective amount of the compound of formula (I). In one embodiment, the present invention provides a method for the treatment or prophylaxis of chronic fatigue syndrome and multiple sclerosis in an animal such as a mammal (e.g., a human), which comprises administering to the animal a therapeutically effective amount of a compound of formula (I). The foregoing method is particularly useful for the treatment or prophylaxis of chronic fatigue syndrome and multiple sclerosis associated with latent infection with a herpes virus.

In another embodiment, the present invention provides a method for the treatment or prophylaxis of a cardiovascular condition such as atherosclerosis, coronary artery disease or restenosis (particularly restenosis following surgery such as angioplasty), which comprises administering to the animal a therapeutically effective antiviral amount of the compound of formula (I).

The present invention further provides a method for the treatment or prophylaxis of hepatitis B or hepatitis C viruses in an animal such as a mammal (e.g., a human), which comprises administering to the animal a therapeutically effective amount of the compound of formula (I).

The present invention further provides a method for the treatment or prophylaxis of human papilloma virus in an animal such as a mammal (e.g., a human), which comprises administering to the animal a therapeutically effective amount of the compound of formula (I).

The present invention further provides a method for the treatment or prophylaxis of HIV in an animal such as a mammal (e.g., a human), which comprises administering to the animal a therapeutically effective amount of the compound of formula (I).

The present invention also provides the use of the compound of formula (I) in the preparation of a medicament for the treatment or prophylaxis of a viral infection in an animal such as a mammal (e.g., a human), particularly a herpes viral infection; the use of the comound of formula (I) in the preparation of a medicament for the treatment of conditions or disease associated with a herpes viral infection; and the use of the compound of formula (I) in the preparation of a medicament for the treatment or prophylaxis of hepatitis B or hepatitis C viruses, human papilloma virus and HIV. In particular, the present invention also provides the use of a compound of formula (I) in the preparation of a medicament for the treatment or prophylaxis of chronic fatigue syndrome or multiple sclerosis. In one embodiment, the present invention provides the use of a compound of formula (I) in the preparation of a medicament for the treatment or prophylaxis of cardiovascular disease, such as restenosis and atherosclerosis.

The compounds of formula (I) are conveniently administered in the form of pharmaceutical compositions. Such compositions may conveniently be presented for use in any conventional manner in admixture with one or more physiologically acceptable carriers or diluents.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical composition or formulation comprising a compound of formula (I) with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition, age, and disorder of the recipient as well as the viral infection or disease being treated. The formulations may conveniently be presented in unit dosage form and may be prepared by any of the methods well known in the art of pharmacy. All methods include the step of bringing into association the compound(s) ("active ingredient") with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured base such as sucrose and acacia or tragacanth, and pastilles comprising the active ingredient in a base such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, preferably 100–1500 mg per day. The desired dose may conveniently be presented in a single dose or as divided doses administered at appropriate intervals, for example as two, three, four or more sub-doses per day. The formulations according to the invention may contain between 0.1–99% of the active ingredient, conveniently from 30–95% for tablets and capsules and 3–50% for liquid preparations.

The compound of formula (I) for use in the instant invention may be used in combination with other therapeutic agents for example, non-nucleotide reverse transcriptase inhibitors, nucleoside reverse transcriptase inhibitors, protease inhibitors and/or other antiviral agents. The invention thus provides in a further aspect the use of a combination comprising a compound of formula (I) with a further therapeutic agent in the treatment of viral infections. Particular antiviral agents which may be combined with the compounds of the present invention include aciclovir, valaciclovir, fameyclovir, gancyclovir, docosanol, miribavir, amprenavir, lamivudine, zidovudine, and abacavir. Preferred antiviral agents for combining with the compounds of the present invention include aciclovir and valaciclovir. Thus the present invention provides in a further aspect, a combination comprising a compound of formula (I) and an antiviral agent selected from the group consisting of aciclovir and valaciclovir; the use of such combination in the treatment of viral infections and the preparation of a medicament for the treatment of viral infections, and a method of treating viral infections comprising administering a compound of formula (I) and an antiviral agent selected from the group consisting of aciclovir and valaciclovir.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optionally together with a pharmaceutically acceptable carrier or diluent comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, in such a manner as are known for such compounds in the art.

When a compound of formula (I) is used in combination with a second therapeutic agent active against the viral infection, the dose of each compound may differ from that when the compound is used alone. Appropriate doses will be readily appreciated by those skilled in the art.

Compounds of formula (I) wherein Y is N, $R^2$ is selected from the group consisting of H, alkyl, cycloalkyl, alkenyl, cycloalkenyl, $-NR^7R^8$, $-OR^7$, $-OAy$, $-S(O)_nR^7$, $-S(O)_nAy$, $-R^{10}NR^7R^8$, $-R^{10}NR^7Ay$, Ay, Het, $-NH$ $(CH_2)_m$Het and $-O(CH_2)_m$Het; and $R^3$ and $R^4$ are H, may be conveniently prepared by a general process outlined in Scheme 1 below.

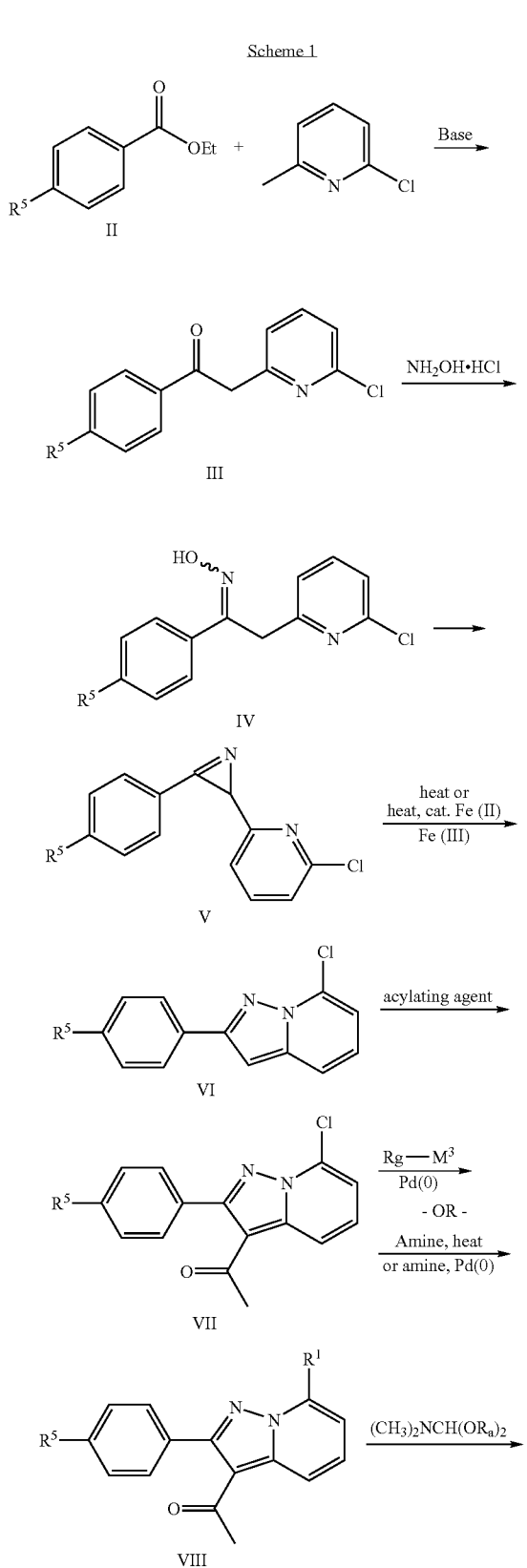

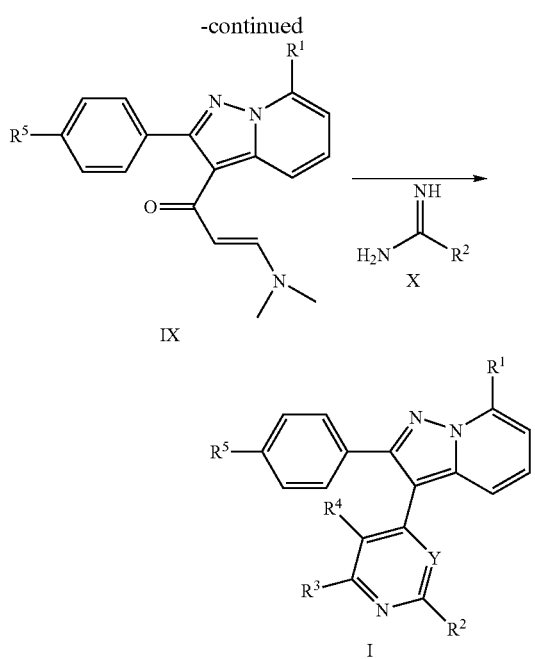

wherein:
R¹ is selected from the group consisting of halo, —NR⁷R⁸, Ay, —NR⁷Ay, Het, —NH(CH₂)ₘHet, and —NH(CH₂)ₗAy;
  each R⁷ and R⁸ are the same or different and are independently selected from the group consisting of H, alkyl, cycloalkyl, alkenyl, cycloalkenyl, alkylhydroxy, amine, alkylamine, alkylcarboxy, alkylcarboxamide, alkyl alkoxycarbonyl, alkylthioamide, alkylsulfonyl, alkylsulfonamide, alkylether, —(CH₂)ₗ-cycloalkyl, —(CH²)ᵢNHCOR⁹ and —(CH₂)ₘSO₂NHCOR⁹;
  l is 1–6;
  m is 0–6;
  R⁹ is H, alkyl, cycloalkyl, alkylhydroxy, amine, alkylamine, alkylcarboxy and alkylether;
Ay is aryl;
Het is a 5- or 6-membered heterocyclic or heteroaryl group;
R² is selected from the group consisting of H, alkyl, cycloalkyl, alkenyl, cycloalkenyl, —NR⁷R⁸, —OR⁷, —OAy, —S(O)ₙR⁷, —S(O)ₙAy, —R¹⁰NR⁷R⁸, —R¹⁰NR⁷Ay, Ay, Het, —NH(CH₂)ₘHet and —O(CH₂)ₘHet;
n is 0, 1 or 2;
R¹⁰ is alkyl or alkenyl;
Y is N;
R³ and R⁴ are both H;
R⁵ is halo;
Rg is Ay or Het as defined above;
M³ is B(OH)₂, B(ORa)₂, B(Ra)₂, Sn(Ra)₃, Zn-halide; Zn—Ra or Mg-halide;
Ra is alkyl or cycloalkyl and
halide is halo.

Generally, the process for preparing the compounds of formula (I) wherein Y is N, R² is selected from the group consisting of H, alkyl, cycloalkyl, alkenyl, cycloalkenyl, —NR⁷R⁸, —OR⁷, —OAy, —S(O)ₙR⁷, —S(O)ₙAy, —R¹⁰NR⁷R⁸, —R¹⁰NR⁷R⁸, Ay, Het, —NH(CH₂)ₘHet and —O(CH₂)ₘHet; and R³ and R⁴ are H, (all formulas and all other variables having been defined above in connection with Scheme 1) comprises the steps of:
(a) reacting 2-chloro-6-picoline with a benzoylating agent of formula (II) to prepare a compound of formula (III);
(b) reacting the compound of formula (III) with a hydroxylamine source to prepare a compound of formula (IV);
(c) reacting the compound of formula (IV) with an acylating or sulfonylating agent to prepare a compound of formula (V);
(d) rearranging the compound of formula (V) to prepare a compound of formula (VI);
(e) acylating the compound of formula (VI) to prepare a compound of formula (VII);
(f) either:
  (1) replacing the C-7 halogen of the compound of formula (VII) with an amine; or
  (2) coupling the compound of formula (VII) with a metal compound of the formula Rg-M₃ to prepare a compound of formula (VIII);
(g) reacting the compound of formula (VIII) with a dimethylformamide dialkyl acetal of formula (CH₃)₂NCH(ORa)₂ to prepare a compound of formula (IX); and
(h) reacting the compound of formula (IX) with a compound of formula (X) to prepare the compounds of formula (I).

More specifically, compounds of formula (I) wherein Y is N, R² is selected from the group consisting of H, alkyl, cycloalkyl, alkenyl, cycloalkenyl, —NR⁷R⁸, —OR⁷, —OAy, —S(O)ₙR⁷, —S(O)ₙAy, —R¹⁰NR⁷R⁸, —R¹⁰NR⁷R⁸, Ay, Het, —NH(CH₂)ₘHet and —O(CH₂)ₘHet; and R³ and R⁴ are H can be prepared by reacting a compound of formula (IX) with a compound of formula (X).

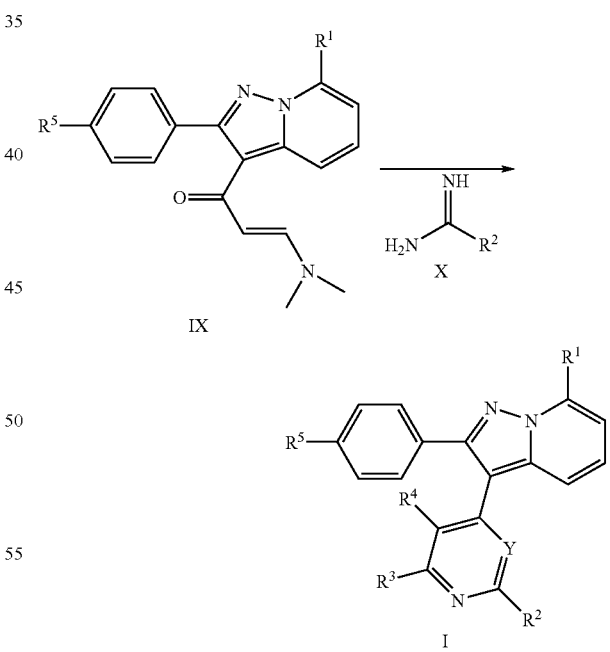

wherein all variables are as defined above in connection with Scheme 1.

This general method can be readily carried out by mixing a compound of formula (IX) with a compound of formula (X) in a suitable solvent, optionally in the presence of a base (preferably when the amidine is in a salt form), and heating the reaction to about 50–150° C. Typical solvents include lower alcohols such as methanol, ethanol, isopropanol, dimethylformamide, or the like. The base is typically a sodium alkoxide, potassium carbonate, or an amine base such as triethylamine. In one embodiment, the solvent is dimethylformamide and the base is potassium carbonate, or an amine base such as triethylamine.

Compounds of the formula (IX) may be conveniently prepared by reacting a compound of formula (VIII) with a dimethylformamide dialkyl acetal.

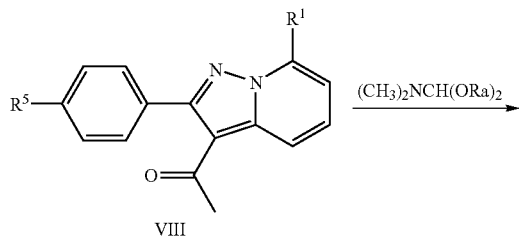

VIII

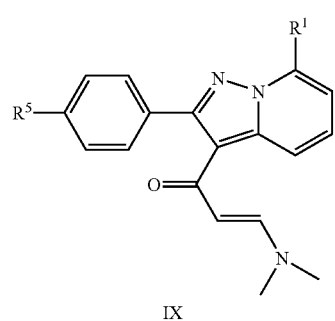

IX wherein all variables are as defined above in connection with Scheme 1.

Typical dimethylformamide dialkylacetal compounds for use in this method include but are not limited to dimethylformamide dimethylacetal and dimethylformamide di-tert-butylacetal. The reaction is carried out by mixing a compound of formula (VIII) with the dimethylformamide dialkyl acetal, optionally with heating.

Compounds of the formula (VIII) may be prepared by two general methods. According to one method, compounds of formula (VIII) are prepared from compounds of formula (VII) by replacement of the C-7 halogen (chloro is depicted in formula (VII) but other halogens are similarly useful) with an amine nucleophile.

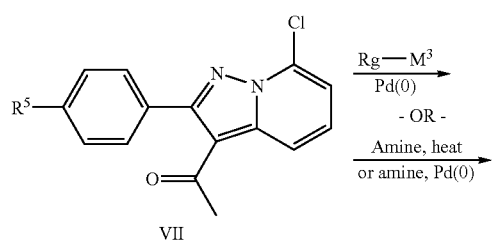

VII

-continued

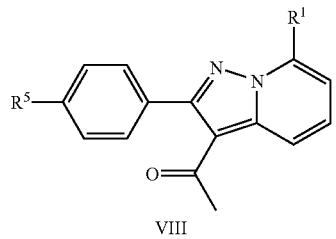

VIII wherein all variables are as defined above in connection with Scheme 1.

Typically the replacement is carried out by mixing the compound of formula (VII) with an amine nucleophile of formula $R^{1a}$ where $R^{1a}$ is selected from the group consisting of $-NR^7R^8$, $-NR^7Ay$, Het, $-NH(CH_2)_m$Het, and $-N(CH_2)_tAy$; and optionally heating the reaction.

The reaction can also be carried out via an adaptation of procedures found in the literature (Wolfe, J. P.; Buchwald, S. L. *J. Org. Chem.* 2000, 65, 1144) wherein a compound of the general formula (VII) is treated with an amine, a palladium (0) or nickel (0) source and a base in a suitable solvent. Suitable sources of palladium (0) include but are not limited to palladium(II) acetate and tris(dibenzylideneacetone) dipalladium (0). Typical bases for use in the reaction include, for example sodium tert-butoxide and cesium carbonate. Toluene is an example of a suitable solvent.

According to the second method, compounds of formula (VIII) are prepared from compounds of formula (VII) by coupling with metal compounds of the formula Rg-$M^3$ wherein Rg is Ay or Het as defined above and $M^3$ is $B(OH)_2$, $B(ORa)_2$, $B(Ra)_2$, $Sn(Ra)_3$, Zn-halide, Zn—Ra or Mg-halide, wherein Ra is alkyl or cycloalkyl and halide is halo. This general method can be conveniently performed in an inert solvent, in the presence of a palladium (0) catalyst, optionally with heating. Preferably the reaction is performed by reacting equimolar amounts of a compound of the general formula (VII) with the metal compound of formula Rg-$M^3$ or optionally adding an excess of the metal compound. The palladium catalyst is preferably present in 1–10 mol % compared to the compound of formula (VII). Palladium catalysts that may be used may include, but are not limited to, tetrakistriphenylphosphine palladium (0) dichlorobis(triphenyl-phosphine)palladium(II), and bis(diphenylphosphinoferrocene)-palladium (II) dichloride. Inert solvents for use in the reaction include but are not limited to, N,N-dimethylformamide, toluene, tetrahydrofuran, dioxane and 1-methyl-2-pyrrolidinone.

When the metal compound of formula Rg-$M^3$ is an arylboronic acid or ester or an arylborinate, the reaction is more conveniently carried out by adding a base in a proportion equivalent to, or greater than, that of the metal compound.

Metal compounds of the formula Rg-$M^3$ can be purchased from commercial sources or prepared either as discreet isolated compounds or generated in situ by using methods known to one skilled in the art. (Suzuki, A. *J. Organomet. Chem.* 1999, 576, 147; Stille, J. *Angew. Chem. Int. Ed. Engl.* 1986, 25, 508; Snieckus, V. *J. Org. Chem.* 1995, 60, 292.)

Compounds of the formula (VII) may be conveniently prepared from compounds of formula (VI) using an acylation procedure.

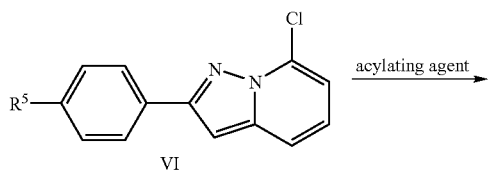

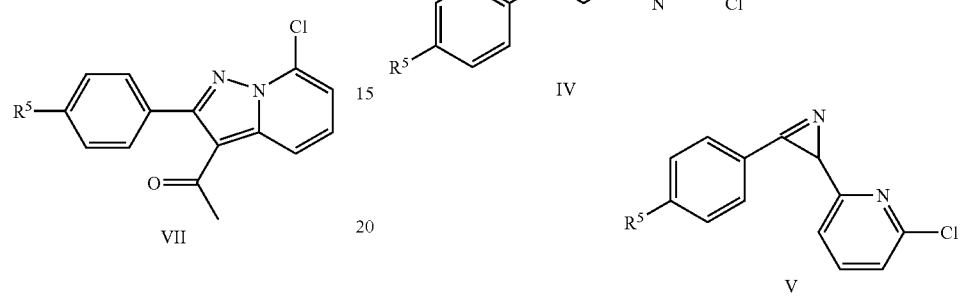

wherein all variables are as defined above in connection with Scheme 1.

Typically the acylation is carried out by treating the compounds of formula (VI) with an acylating agent, optionally in the presence of an acid or Lewis acid catalyst in an inert solvent with optional heating. Typical acylating agents will be readily determined by those skilled in the art One preferred acylating agent is acetic anhydride. Lewis acid catalysts are also known to those skilled in the art. One preferred Lewis acid catalyst for use in this reaction is boron trifluoride diethyl etherate. A suitable solvent is toluene.

Compounds of formula (VI) are conveniently prepared by rearranging an azirine compound of formula (V).

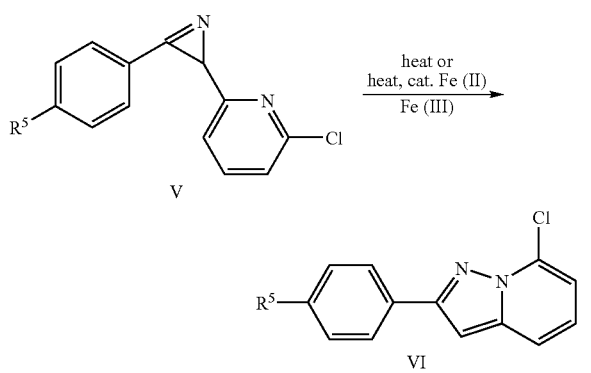

wherein all variables are as defined above in connection with Scheme 1.

The rearrangement of the azirines of formula (V) can be accomplished by heating a solution of the azirine of formula (V) in a suitable solvent at a temperature of about 160–200° C. Suitable inert solvents include, but are not limited to, 1-methyl-2-pyrrolidinone, and 1,2,4-trichlorobenzene. A more preferred method for rearrangement of the azirine of formula (V) to compounds of formula (VI) involves reacting the compound of formula (V) with ferrous chloride ($FeCl_2$) or ferric chloride ($FeCl_3$). This reaction is typically done in an inert solvent with heating. A preferred solvent for this reaction is 1,2-dimethoxyethane and the like.

Typically the azirines of formula (V) are prepared from oxime compounds of formula (IV) by treatment with acylating or sulfonylating agents in the presence of a base.

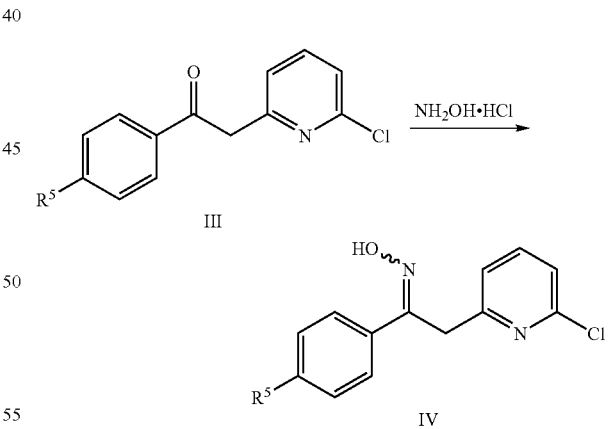

wherein all variables are as defined above in connection with Scheme 1.

Typical acylating or sulfonylating agents include but are not limited to, acetic anhydride, trifluoroacetic anhydride, methanesulfonyl chloride, toluenesulfonyl chloride and the like. Typical bases include, but are not limited to triethylamine, diisopropylethylamine, pyridine, or the like. The reaction may be carried out in an inert solvent such as for example, chloroform, dichloromethane, toluene or the like.

The oxime compounds of formula (IV) are readily prepared by treating ketone compounds of formula (III) with a hydroxylamine source, in a suitable solvent, and optionally with a base.

wherein all variables are as defined above in connection with Scheme 1.

Preferably the hydroxylamine is hydroxylamine hydrochloride and the base is an aqueous solution of sodium hydroxide. Suitable solvents include lower alcohols such as methanol, ethanol, or isopropanol.

The ketone compounds of formula (III) can be prepared by treatment of 2-chloro-6-picoline with a benzoylating agent of formula (II) in the presence of a base.

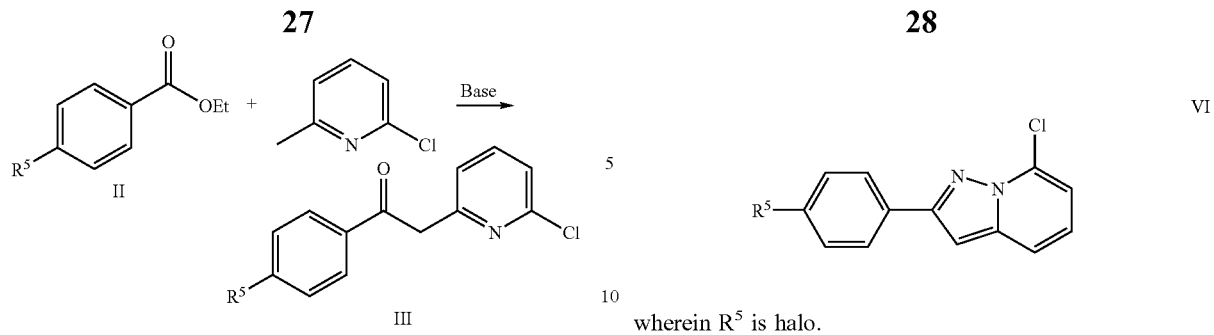

wherein all variables are as defined above in connection with Scheme 1.

Preferred benzoylating agents of formula (II) include, but are not limited to, benzoyl esters. An example of a suitable base is lithium bis(trimethylsilyl)amide in an inert solvent such as tetrahydrofuran. Ketones such as those of formula (III) can be readily prepared using procedures known to one skilled in the art and/or described in the literature (Cassity, R. P.; Taylor, L. T.; Wolfe, J. F. *J. Org. Chem.* 1978, 2286).

In addition to the foregoing process for preparing certain compounds of formula (I), the present invention also provides certain intermediate compounds for use in the preparation of such compounds of formula (I) according to the foregoing process. As one aspect, the present invention provides compounds of formula (III)

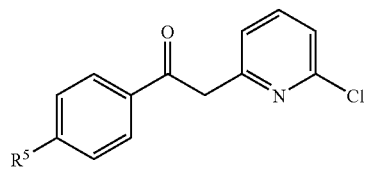

III wherein $R^5$ is halo.

As another aspect, the present invention provides compounds of formula (IV)

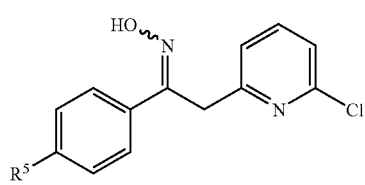

IV wherein $R^5$ is halo.

As another aspect, the present invention provides compounds of formula (V)

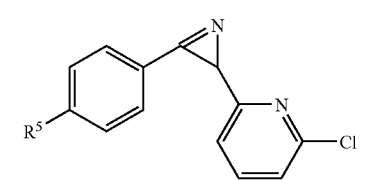

V wherein $R^5$ is halo.

As another aspect, the present invention provides compounds of formula (VI)

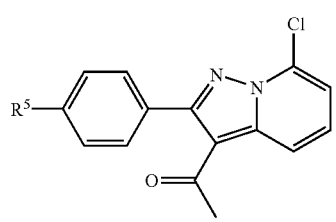

VI wherein $R^5$ is halo.

As another aspect, the present invention provides compounds of formula (VII)

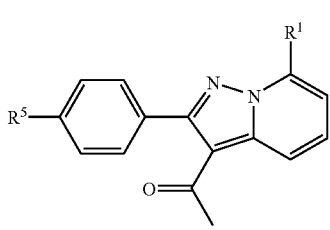

VII wherein $R^5$ is halo.

As another aspect, the present invention provides compounds of formula (VIII)

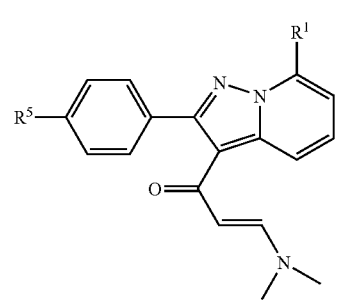

VIII wherein $R^1$ and $R^5$ are as defined above.

As another aspect, the present invention provides compounds of formula (IX)

IX wherein $R^1$ and $R^5$ are as defined above.

In a further embodiment of the present invention, compounds of formula (I) wherein Y is N; $R^2$ is selected from the group consisting of H, alkyl, cycloalkyl, alkenyl, cycloalkenyl, —$NR^7R^8$, —$OR^7$, —OAy, —$S(O)_nR^7$, —$S(O)_nAy$, —$R^{10}NR^7R^8$, —$R^{10}NR^7R^8$, Ay, Het, —$NH(CH_2)_m$Het and —$O(CH_2)_m$Het; $R^3$ is selected from the group consisting of H, alkyl, alkylhydroxy, alkylamine, —NR⁷R⁸ where R⁷ and R⁸ are not H, —NR⁷Ay where R⁷ is not H, carboxy, carboxamide, —SO₂NHR⁹, Het and Ay; and R⁴ is H, may be conveniently prepared by a general process outlined in Scheme 2 below.

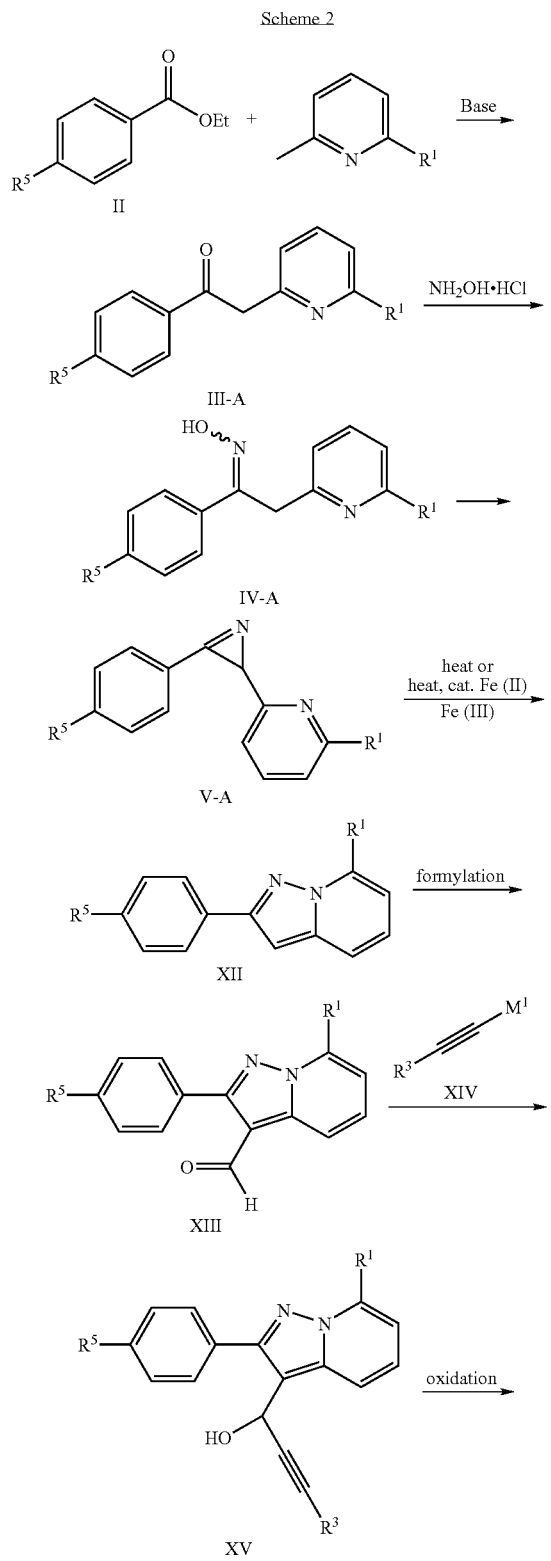

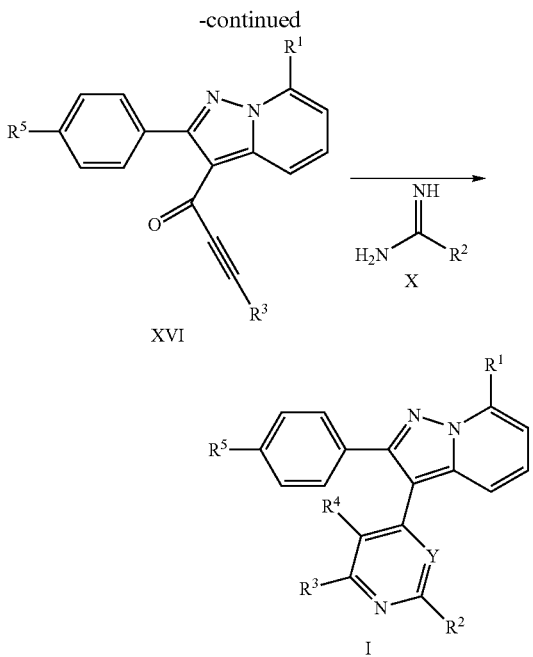

wherein R¹ is selected from the group consisting of halo, —NR⁷R⁸, —NR⁷Ay, Ay, Het, —NH(CH₂)$_m$Het, and —NH(CH₂)$_l$Ay;

each R⁷ and R⁸ are the same or different and are independently selected from the group consisting of H, alkyl, cycloalkyl, alkenyl, cycloalkenyl, alkylhydroxy, amine, alkylamine, alkylcarboxy, alkylcarboxamide, alkyl alkoxycarbonyl, alkylthioamide, alkylsulfonyl, alkylsulfonamide, alkylether, —(CH₂)$_l$-cycloalkyl, —(CH²)$_l$NHCOR⁹ and —(CH₂)$_m$SO₂NHCOR⁹;

l is 1–6;

m is 0–6;

R⁹ is H, alkyl, cycloalkyl, alkylhydroxy, amine, alkylamine, alkylcarboxy and alkylether;

Ay is aryl;

Het is a 5- or 6-membered heterocyclic or group;

R² is selected from the group consisting of H, alkyl, cycloalkyl, alkenyl, cycloalkenyl, —NR⁷R⁸, —OR⁷, —OAy, —S(O)$_n$R⁷, —S(O)$_n$Ay, —R¹⁰NR⁷R⁸, —R¹⁰NR⁷Ay, Ay, Het, —NH(CH₂)$_m$Het and —O(CH₂)$_m$Het;

R³ is selected from the group consisting of H, alkyl, alkylhydroxy, alkylamine, alkylether, —NR⁷R⁸ where R⁷ and R⁸ are not H, —NR⁷Ay where R⁷ is not H, carboxy, carboxamide, —SO₂NHR⁹, Het and Ay;

R⁴ is H;

R⁵ is halo; and

M¹ is Li, Mg-halide or cerium-halide, wherein halide is halo.

Generally, the process for preparing compounds of formula (I) wherein Y is N; R² is selected from the group consisting of H, alkyl, cycloalkyl, alkenyl, cycloalkenyl, —NR⁷R⁸, —OR⁷, —OAy, —S(O)$_n$R⁷, —S(O)$_n$Ay, —R¹⁰NR⁷R⁸, —R¹⁰NR⁷R⁸, Ay, Het, —NH(CH₂)$_m$Het and —O(CH₂)$_m$Het; R³ is selected from the group consisting of H, alkyl, alkylhydroxy, alkylamine, alkylether, —NR⁷R⁸ where R⁷ and R⁸ are not H, —NR⁷Ay where R⁷ is not H, carboxy, carboxamide, —SO₂NHR⁹, Het and Ay; and R⁴ is H (all formulas and all other variables having been defined above in connection with Scheme 2), comprises the following steps:
(a) reacting a picoline with a benzoylating agent of formula (II) to prepare a compound of formula (III-A);
(b) reacting the compound of formula (III-A) with a hydroxylamine source to prepare a compound of formula (IV-A);
(c) reacting the compound of formula (IV-A) with an acylating or sulfonylating agent to prepare a compound of formula (V-A);
(d) rearranging the compound of formula (V-A) to prepare a compound of formula (XII);
(e) formylating the compound of formula (XII) to prepare a compound of formula (XIII);
(f) reacting the compound of formula (XIII) with a compound of formula (XIV) to prepare a compound of formula (XV);
(g) oxidizing the compound of formula (XV) to prepare a compound of formula (XVI); and
(h) reacting a compound of formula (XVI) with a compound of formula (X) to prepare the compound of formula (I).

More specifically, compounds of formula (I) wherein Y is N; $R^2$ is selected from the group consisting of H, alkyl, cycloalkyl, alkenyl, cycloalkenyl, —$NR^7R^8$, —$OR^7$, —OAy, —$S(O)_nR^7$, —$S(O)_nAy$, —$R^{10}NR^7R^8$, —$R^{10}NR^7Ay$, Ay, Het, —$NH(CH_2)_m$Het and —$O(CH_2)_m$Het; $R^3$ is selected from the group consisting of H, alkyl, alkylhydroxy, alkylamine, alkylether, —$NR^7R^8$ where $R^7$ and $R^8$ are not H, —$NR^7Ay$ where $R^7$ is not H, carboxy, carboxamide, —$SO_2NHR^9$, Het and Ay; and $R^4$ is H, can be prepared by reacting a compound of formula (XVI) with a compound of formula (X).

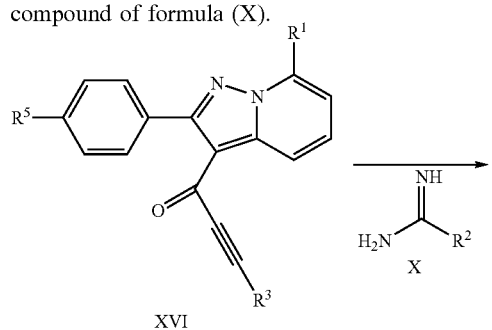

wherein all variables are as defined above in connection with Scheme 2.

This method can be readily carried out by mixing a compound of formula (XVI) with a compound of formula (X) in a suitable solvent, optionally in the presence of a base. The reaction may be heated to 50–150° C. or performed at ambient temperature. Typical solvents include but are not limited to lower alcohols such as methanol, ethanol, isopropanol and the like. Typical bases include for example, sodium alkoxide, potassium carbonate, or an amine base such as triethylamine. In another embodiment, the solvent is N,N-dimethylformamide and the base is potassium carbonate, or an amine base such as triethylamine.

Compounds of formula (XVI) may be conveniently prepared by oxidation of a compound of formula (XV).

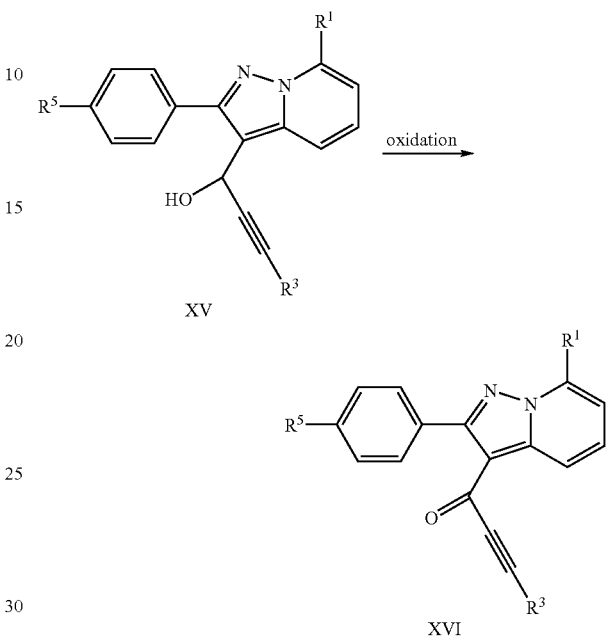

wherein all variables are as defined above in connection with Scheme 2.

Preferred oxidizing agents include but are not limited to, manganese dioxide, and the like, in an inert solvent Suitable inert solvents include but are not limited to, dichloromethane, chloroform, N,N-dimethylformamide, ether, and the like.

Compounds of formula (XV) may be conveniently prepared by reacting a compound of formula (XIII) with a compound of formula (XIV).

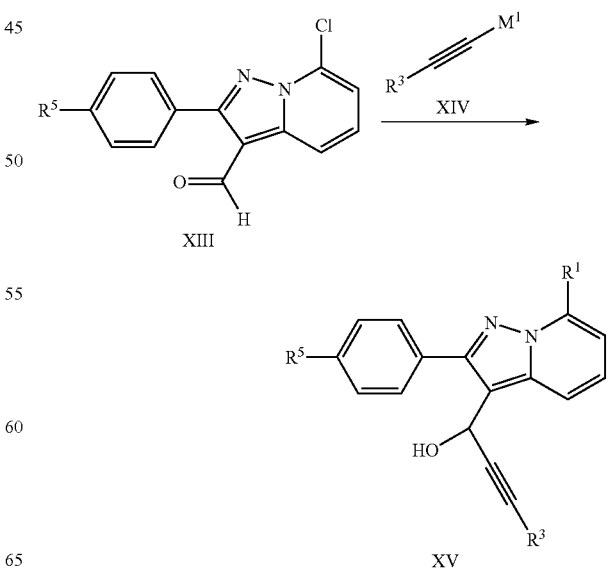

wherein all variables are as defined above in connection with Scheme 2.

Preferred metals (M¹) in the compounds of formula (XIV) include but are not limited to, lithium, magnesium(II) halides, cerium(III) halides, and the like. Compounds of general formula (XIV) may be purchased from commercial sources or prepared by methods known to one skilled in the art.

Compounds of formula (XIII) may be conveniently prepared from compounds of formula (XII) by a formylation procedure.

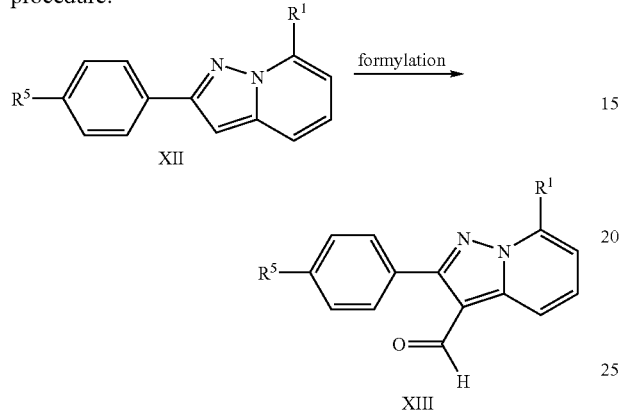

wherein all variables are as defined above in connection with Scheme 2.

Typically the formylation is carried out via the Vilsmeier-Haack reaction. The Vilsmeier-Haack reagents can be purchased from commercial sources or prepared in situ. Preferable conditions include, but are not limited to treating compounds of formula (XII) with a premixed solution of phosphorous oxychloride in N,N-dimethylformamide optionally with heating the reaction to 50–150° C.

The compounds of formula (XII) are prepared by a process analogous to the process employed for the preparation of compounds of formula (VI) in Scheme 1 above.

In addition to the foregoing process for preparing certain compounds of formula (I), the present invention also provides certain intermediate compounds for use in the preparation of such compounds of formula (I) according to the foregoing process. Thus, as one aspect, the present invention provides compounds of formula (III-A)

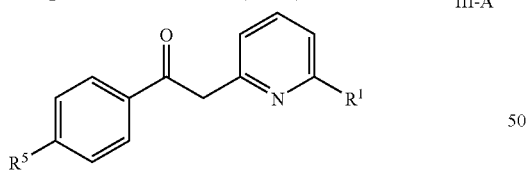

wherein $R^1$ and $R^5$ are as defined above.

As another aspect, the present invention provides compounds of formula (IV-A)

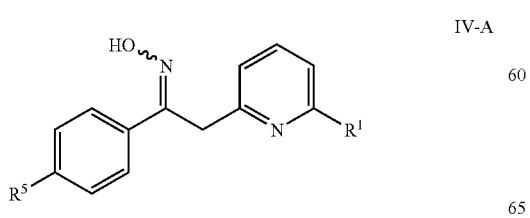

wherein $R^1$ and $R^5$ are as defined above.

As another aspect, the present invention provides compounds of formula (V-A)

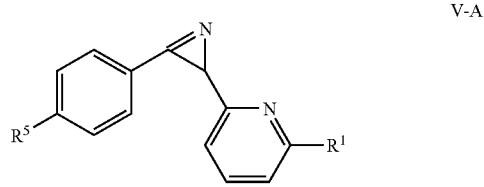

wherein $R^1$ and $R^5$ are as defined above.

As another aspect, the present invention provides compounds of formula (XII)

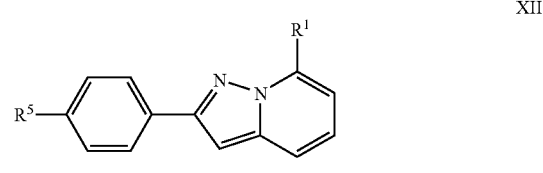

wherein $R^1$ and $R^5$ are as defined above.

In another aspect, the present invention provides compounds of formula (XIII)

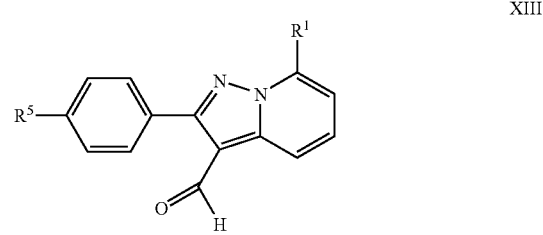

wherein $R^1$ and $R^5$ are as defined above.

In another aspect, the present invention provides compounds of formula (XV)

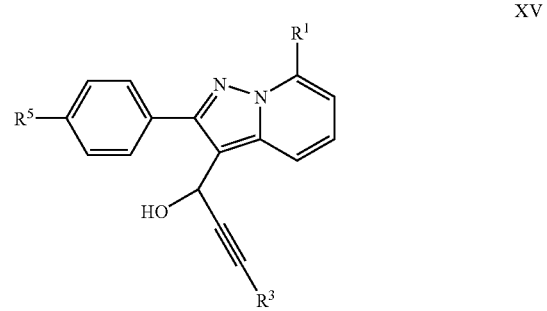

wherein $R^1$, $R^3$ and $R^5$ are as defined above.

In another aspect, the present invention provides compounds of formula (XVI)

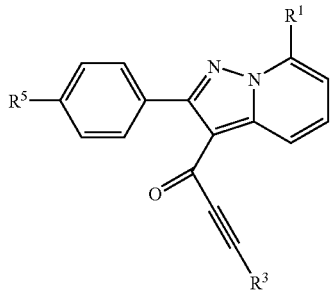

XVI

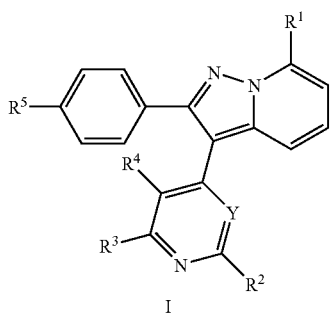

I wherein $R^1$, $R^3$ and $R^5$ are as defined above.

Compounds of formula (I) wherein Y is N and $R^2$ is selected from the group consisting of H, alkyl, cycloalkyl, alkenyl, cycloalkenyl, —$NR^7R^8$, —$OR^7$, —OAy, —$S(O)_nR^7$, —$S(O)_nAy$, —$R^{10}NR^7R^8$, —$R^{10}NR^7Ay$, Ay, Het, —NH$(CH_2)_m$Het and —O$(CH_2)_m$Het; may be conveniently prepared by a general process outlined in Scheme 3 below.

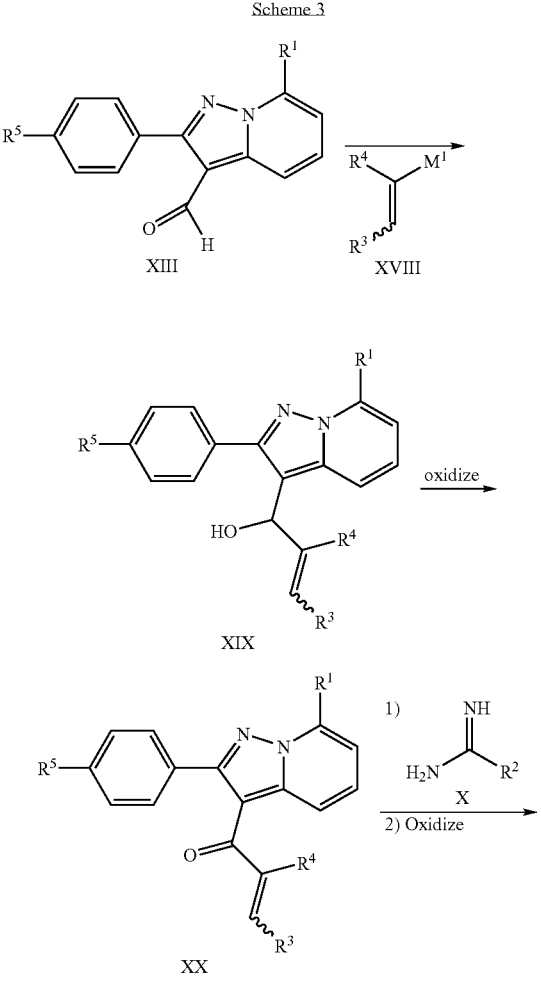

Scheme 3 wherein $R^1$ is selected from the group consisting of halo, —$NR^7R^8$, Ay, —$NR^7Ay$, Het, —NH$(CH_2)_m$Het, and —NH$(CH_2)_tAy$;

each $R^7$ and $R^8$ are the same or different and are independently selected from the group consisting of H, alkyl, cycloalkyl, alkenyl, cycloalkenyl, alkylhydroxy, amine, alkylamine, alkylcarboxy, alkylcarboxamide, alkyl alkoxycarbonyl, alkylthioamide, alkylsulfonyl, alkylsulfonamide, alkylether, —$(CH_2)_t$-cycloalkyl, —$(CH^2)_t$NHCOR$^9$ and —$(CH_2)_m$SO$_2$NHCOR$^9$;

l is 1–6;

m is 0–6;

$R^9$ is H, alkyl, cycloalkyl, alkylhydroxy, amine, alkylamine, alkylcarboxy and alkylether;

Ay is aryl;

Het is a 5- or 6-membered heterocyclic or heteroaryl group;

$R^2$ is selected from the group consisting of H, alkyl, cycloalkyl, alkenyl, cycloalkenyl, —$NR^7R^8$, —$OR^7$, —OAy, —$S(O)_nR^7$, —$S(O)_nAy$, —$R^{10}NR^7R^8$, —$R^{10}NR^7Ay$, Ay, Het, —NH$(CH_2)_m$Het and —O$(CH_2)_m$Het;

n is 0, 1 or 2;

$R^{10}$ is alkyl or alkenyl;

Y is N or CH;

$R^3$ and $R^4$ are each independently selected from the group consisting of H, halo, hydroxy, alkyl, alkylhydroxy, alkylamine, alkylether, —$OR^7$, —OAy, —$NR^7R^8$, —$NR^7Ay$, carboxy, carboxamide, —SO$_2$NHR$^9$, Het and Ay;

$R^5$ is halo; and $M^1$ is Li, Mg-halide or cerium-halide, wherein halide is halo.

Generally, the process for preparing compounds of formula (I) wherein Y is N and $R^2$ is selected from the group consisting of H, alkyl, cycloalkyl, alkenyl, cycloalkenyl, —$NR^7R^8$, —$OR^7$, —OAy, —$S(O)_nR^7$, —$S(O)_nAy$, —$R^{10}NR^7R^8$, —$R^{10}NR^7Ay$, Ay, Het, —NH$(CH_2)_m$Het and —O$(CH_2)_m$Het; (all formulas and all other variables having been defined above in connection with Scheme 3), comprises the following steps:

(a) reacting a compound of formula (XIII) with a compound of formula (XVIII) to prepare a compound of formula (XIX);

(b) oxidizing the compound of formula (XIX) to prepare a compound of formula (XX); and (c) reacting a compound of formula (XX) with a compound of formula (X) followed by oxidative aromatization to prepare the compound of formula (I).

More specifically, compounds of formula (I) wherein Y is N and $R^2$ is selected from the group consisting of H, alkyl, cycloalkyl, alkenyl, cycloalkenyl, —$NR^7R^8$, —$OR^7$, —OAy, —$S(O)_nR^7$, —$S(O)_nAy$, —$R^{10}NR^7R^8$, —$R^{10}NR^7Ay$, Ay, Het, —$NH(CH_2)_m$Het and —$O(CH_2)_m$Het; can be prepared by reacting a compound of formula (XX) with a compound of formula (X) followed by oxidative aromatization.

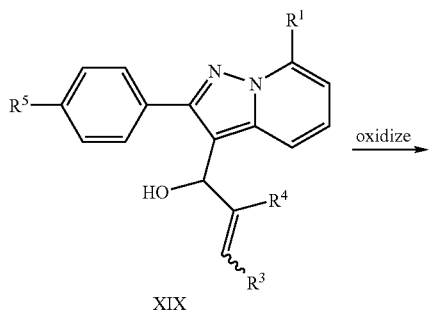

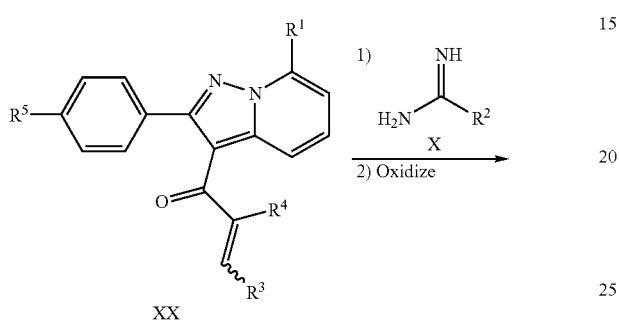

wherein all variables are as defined above in connection with Scheme 3.

The condensation is conveniently carried out by treating the compound of formula (XX) with a compound of formula (X) in an inert solvent, optionally in the presence of a base. The reaction may be heated to 50–150° C. or performed at ambient temperature. Suitable inert solvents include lower alcohols such as, for example, methanol, ethanol, isopropanol and the like. The base is typically sodium alkoxide, potassium carbonate, or an amine base such as triethylamine. In another embodiment, the solvent is N,N-dimethylformamide and the base is potassium carbonate, or amine base such as triethylamine. The reaction produces a dihydropyrimidine intermediate.

Preferrably in the same reaction vessel, the dihydropyrimidine intermediate may be oxidized to a compound of formula (I) by the addition of an oxidizing agent. Preferrably, the oxidizing agent is oxygen ($O_2$), palladium on carbon, 2,3-dichloro-5,6-dicyano-1,4-benzoquinone, or the like.

Compounds of formula (XX) may be conveniently prepared by oxidation of compounds of formula (XIX).

wherein all variables are as defined above in connection with Scheme 2.

Preferred oxidizing agents for the oxidation of compounds of formula (XIX) include but are not limited to manganese dioxide, and the like. The oxidation is typically carried out in an inert solvent such as for example, dichloromethane, chloroform, N,N-dimethylformamide, ether, or the like.

Compounds of formula (XIX) may be conveniently prepared by reacting a compound of formula (XIII) with a compound of formula (XVIII).

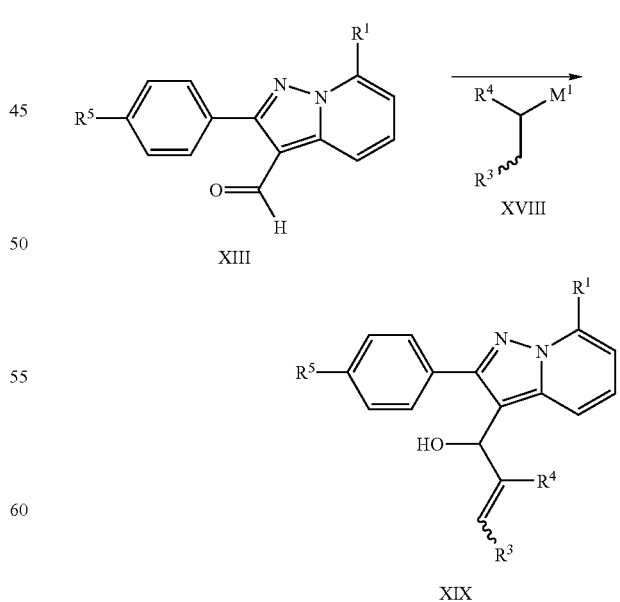

wherein all variables are as defined above in connection with Scheme 2.

Compounds of formula (XVIII) may be purchased from commercial sources or prepared by methods known to one skilled in the art. The compounds of formula (XIII) may be prepared using the methods described in connection with Scheme 2 above.

In addition to the foregoing process for preparing certain compounds of formula (I), the present invention also provides certain intermediate compounds for use in the preparation of such compounds of formula (I) according to the foregoing process. Thus, as one aspect, the present invention provides compounds of formula (XIX)

XIX wherein all variables are as defined above.

In another aspect, the present invention provides compounds of formula (XX)

XX wherein all variables are as defined above.

Compounds of formula (I) wherein Y is CH or N, may be conveniently prepared by a general process outlined in Scheme 4 below.

Scheme 4

XII

Halogenation →

XXII

+

-continued

XXIV

Pd(0) or Ni(0) →

I wherein:
R$^1$ is selected from the group consisting of halo, —NR$^7$R$^8$, Ay, —NR$^7$Ay, Het, —NH(CH$_2$)$_m$Het, and —NH(CH$_2$)$_l$Ay;

each R$^7$ and R$^8$ are the same or different and are independently selected from the group consisting of H, alkyl, cycloalkyl, alkenyl, cycloalkenyl, alkylhydroxy, amine, alkylamine, alkylcarboxy, alkylcarboxamide, alkyl alkoxycarbonyl, alkylthioamide, alkylsulfonyl, alkylsulfonamide, alkylether, —(CH$_2$)$_l$-cycloalkyl, —(CH$^2$)$_l$NHCOR$^9$ and —(CH$_2$)$_m$SO$_2$NHCOR$^9$;

l is 1–6;
m is 0–6;
R$^9$ is H, alkyl, cycloalkyl, alkylhydroxy, amine, alkylamine, alkylcarboxy and alkylether;
Ay is aryl;
Het is a 5- or 6-membered heterocyclic or heteroaryl group;
R$^2$ is selected from the group consisting of H, halo, alkyl, cycloalkyl, alkenyl, cycloalkenyl, —NR$^7$R$^8$, —OR$^7$, —OAy, —S(O)$_n$R$^7$, —S(O)$_n$Ay, —R$^{10}$NR$^7$R$^8$, —R$^{10}$NR$^7$Ay, Ay, Het, —NH(CH$_2$)$_m$Het and —O(CH$_2$)$_m$Het;
n is 0, 1 or 2;
R$^{10}$ is alkyl or alkenyl;
Y is N or CH;
R$^3$ and R$^4$ are each independently selected from the group consisting of H, halo, hydroxy, alkyl, alkylhydroxy, alkylamine, alkylether, —OR$^7$, —OAy, —NR$^7$R$^8$, —NR$^7$Ay, carboxy, carboxamide, —SO$_2$NHR$^9$, Het and Ay;
R$^5$ is halo;
X$^1$ is chloro, bromo, or iodo; and
M$^2$ is —B(OH)$_2$, —B(ORa)$_2$, —B(Ra)$_2$, —Sn(Ra)$_3$, Zn-halide, ZnRa, or Mg-halide where Ra is alkyl or cycloalkyl and halide is halo.

Generally, the process for preparing compounds of formula (I) (all formulas and variables having been defined above in connection with Scheme 4), comprises the following steps:

a) halogenating a compound of formula (XII) to prepare a compound of formula (XXII); and b) reacting the compound of formula (XXII) with a compound of formula (XXIV) to prepare the compound of formula (I).

More specifically, compounds of formula (I) can be prepared by reacting a compound of formula (XXII) with a compound of formula (XXIV).

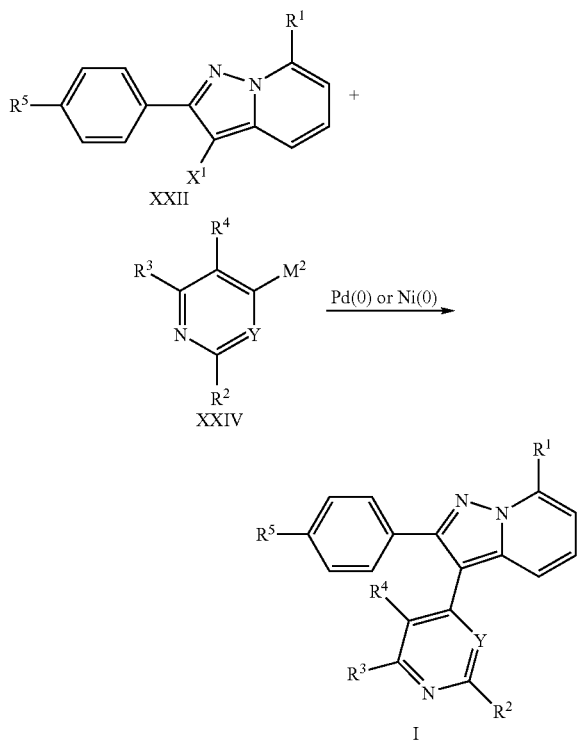

wherein all variables are as defined above in connection with Scheme 4.

The reaction may be carried out in an inert solvent, in the presence of a palladium (0) or nickel (0) catalyst. The reaction may optionally be heated to about 50–150° C. Preferably the reaction is performed by reacting equimolar amounts of a compound of formula (XXII) with a Het-metal compound of formula (XXIV), but the reaction may also be performed in the presence of an excess of compound of the formula (XXIV). The palladium or nickel catalyst is preferrably present in 1–10 mol % compared to the compound of formula (XXII). Examples of suitable palladium catalysts include but are not limited to, tetrakis(triphenylphosphine) palladium (0), dichlorobis(triphenyl-phosphine)palladium (II), and bis(diphenylphosphinoferrocene)palladium (II) dichloride. Suitable solvents include but are not limited to, N,N-dimethylformamide, toluene, tetrahydrofuran, dioxane, and 1-methyl-2-pyrrolidinone. When the Het-metal compound of formula (XXIV) is an arylboronic acid or ester or an arylborinate the reaction is more conveniently carried out by adding a base in a proportion equivalent to, or greater than, that of the compound of formula (XXIV). Het-metal compounds of formula (XXIV) may be obtained from commercial sources or prepared either as discreet isolated compounds or generated in situ using methods known to one skilled in the art. (Suzuki, A. *J. Organomet. Chem.* 1999, 576, 147; Stille, J. *Angew. Chem. Int. Ed. Engl.* 1986, 25, 508; Snieckus, V. *J. Org. Chem.* 1995, 60, 292.)

Compounds of formula (XXII) can be prepared from compounds of formula (XII) by a halogenation procedure.

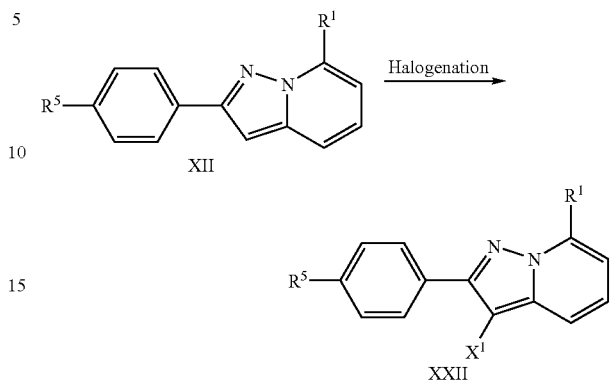

wherein all variables are as defined above in connection with Scheme 4.

Typically, the halogenation reaction is carried out by subjecting the compounds of formula (XII) to a halogenating agent in a suitable solvent. Suitable halogenating agents include but are not limited to, N-bromosuccinimide, trialkylammonium tribromides, bromine, N-chlorosuccinimide, N-iodosuccinimide, iodine monochloride, and the like. Suitable solvents include, for example, N,N-dimethylformamide, tetrahydrofuran, dioxane, 1-methyl-2-pyrrolidinone, carbon tetrachloride, toluene, dichloromethane, diethyl ether, or the like.

In the embodiments wherein the compound of formula (XXII) is defined where $R^1$ is chloro, (i.e., compounds of formula (XXII-A)) and compounds of formula (I) where $R^1$ is other than chloro are desired, it may be desireable to convert the compounds of formula (XXII-A) to compounds of formula (XXII-B) prior to reacting with the Het-metal of formula (XXIV). Compounds of formula (XXII-B) can be conveniently and surprisingly prepared from compounds of formula (XXII-A) by an amination procedure.

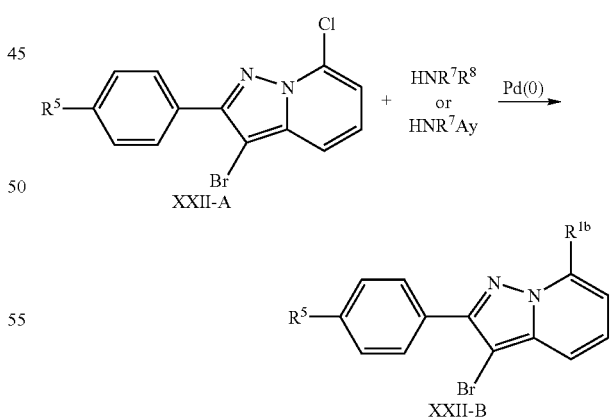

wherein $R^{1b}$ is —$NR^7R^8$ or —$NR^7Ay$ and all other variables are as defined above in connection with Scheme 4.

The ability to replace the chlorine in preference to the bromine of the heterocyclic ring system is unexpected. Preferably, a compound of formula (XXII-A) is reacted with a primary or secondary amine having substitutions corresponding to those of $R^1$, in the presence of a palladium catalyst and a base. The procedure represents a modification of procedures found in the literature (Wolfe, J. P.; Buchwald, S. L. *J. Org. Chem.* 2000, 65, 1144) wherein amines are cross-coupled to aryl halides. Suitable palladium (0) catalysts include palladium(II) acetate and tris(dibenzylideneacetone) dipalladium (0). Suitable bases include sodium tert-butoxide and cesium carbonate. Solvents such as toluene may be employed.

In addition to the foregoing process for preparing compounds of formula (I), the present invention also provides certain intermediate compounds for use in the preparation of compounds of formula (I) according to the foregoing process. Thus, as one aspect, the present invention provides compounds of formula (XXII)

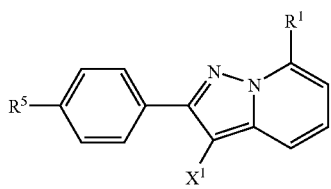

XXII wherein all variables are as defined above.

Another method for the preparation of the compounds of Formula (XXII) in this invention is the decarboxylation/bromination sequence as shown below.

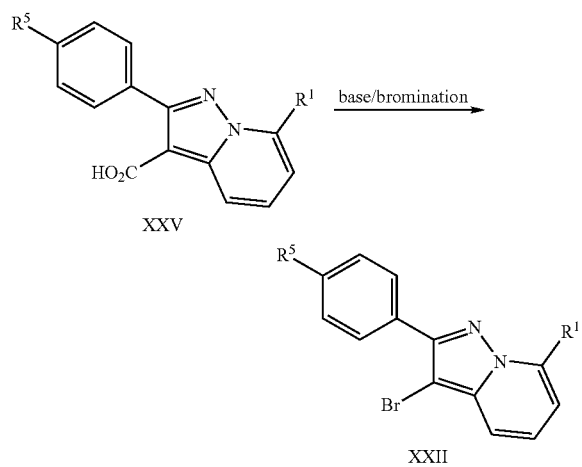

wherein $R^1$ and $R^5$ are as defined above in connection with Scheme 4.

This reaction can be achieved by treatment of a compound of formula (XXV), dissolved in a suitable solvent, with a base followed by a brominating agent and stirring the mixture at, or about, 25° C. until the reaction is judged complete by the disappearance of (XXV). Suitable solvents include, but are not limited to, dimethylformamide, dimethylacetamide, dioxane and the like. Conveniently the base is sodium hydrogen carbonate and the brominating agent can be, for example, N-bromosuccinimide.

Compounds of formula (XXV) can be prepared most readily by simple hydrolysis of lower alkyl esters of formula (XXVI). Esters such as (XXVI) may be prepared by a cycloaddition reaction between compounds of formula (XXVII) and acetylenes of formula (XXVIII), as summarized below.

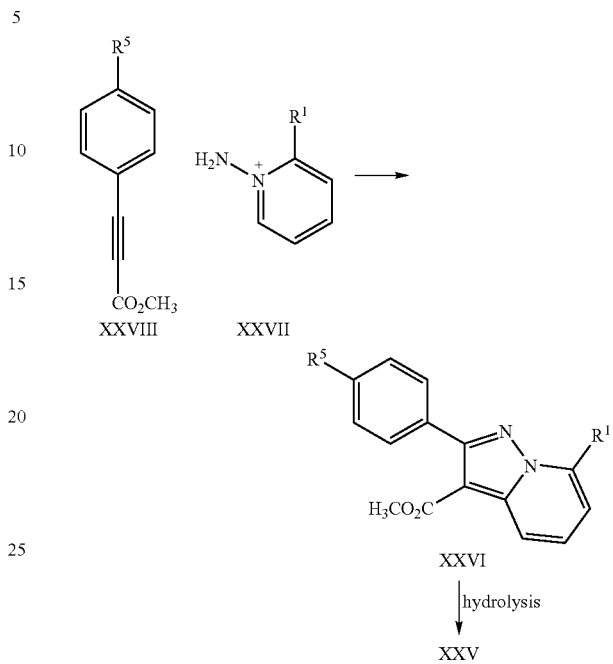

wherein $R^1$ and $R^5$ are as defined above in connection with Scheme 4.

Cycloaddition reactions such as these are commonly known as [3+2] dipolar cycloaddition reactions. Conveniently the reaction may be carried out by mixing the reactants (XXVII) and (XXVIII), in equimolar amounts, in an inert solvent and adding a suitable base. The mixture is then stirred at between 20–100° C. until the reaction is judged complete by the disappearance of one of the reactants. Preferred solvents include but are not limited to acetonitrile, dioxane, tetrahydrofuran, dimethylformamide and the like. Preferred bases include non-nucleophilic amines such as 1,8-diazabicyclo[5.4.0]undec-7-ene, 1,5-diazabicyclo[4.3.0]non-5-ene, 1,4-diazabicyclo[2.2.2]octane and the like.

Esters such as those of Formula (XXVI) can be conveniently hydrolyzed to their corresponding carboxylic acids by standard hydrolysis conditions employed to effect similar hydrolysis reactions (Larock, Comprehensive Organic Transformations, 1989, 981). For example, treatment of a solution of a compound of formula (XXVI) in a lower alcohol, for example methanol, with sodium hydroxide followed by heating the mixture for an appropriate time gives the compound of formula (XXV). Compounds of formula (XXVII) are aminated pyridine derivatives and are either commercially available or can be conveniently prepared by reacting a suitable pyridine with an aminating reagent such as O-(mesitylsulfonyl)hydroxylamine, O-(diphenylphosphinyl)hydroxylamine, hydroxylamine-O-sulfonic acid and the like.

Acetylenic esters such as those of general formula (XXVIII) are either known compounds or can be prepared by methods described in the literature. Preferred methods include the reaction of acetylenes such as those of formula (XXIX) with a suitable base to generate an acetylenic anion and subsequent reaction of the anion with an alkoxycarbonylating agent, as summarized below.

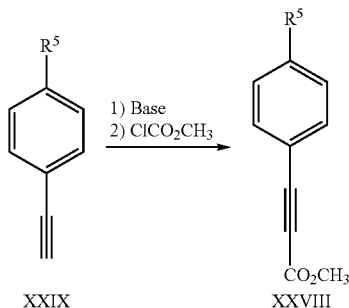

wherein R⁵ is as defined above in connection with Scheme 4.

Preferably the acetylene (XXIX) is dissolved in an inert solvent, such as tetrahydrofuran, and the solution is cooled to about −75° C. A non-nuclephilic base is added in sufficient quantity to effect deprotonation of the acetylene (XXIX). The preferred bases include, but are not limited to, n-butyllithium, lithium diisopropylamide, sodium bis(trimethylsilyl)amide and the like. To the reaction mixture is then added a reagent capable of reacting with an anion to introduce an alkoxycarbonyl group. Preferred reagents include, but are not limited to, methyl chloroformate, ethyl chloroformate, benzyl chloroformate and the like. Arylalkynes such as (XIX) are either known compounds or can be prepared by literature methods such as those described in, for example, Negishi, E. *J. Org. Chem.* 1997, 62, 8957.

Compounds of general formula (XXII) can also be prepared via a number of other convenient routes. Disubstituted acetylenes as represented by formula (XXX) can be treated with an aminating agent, optionally in the presence of a base, to give compounds of general formula (XII). The aminating agent is, preferably, O-(mesitylsulfonyl)hydroxylamine and the base is potassium carbonate.

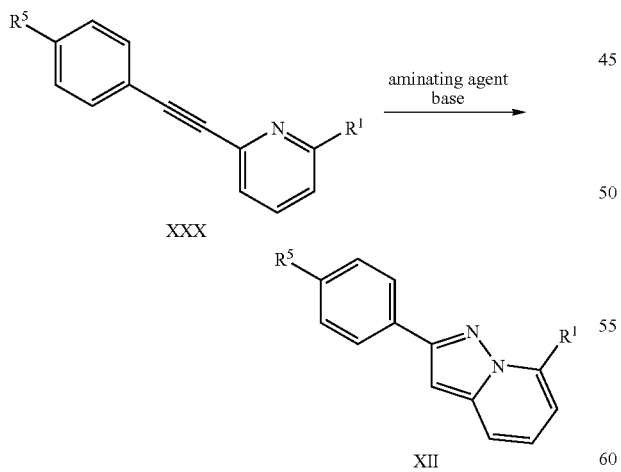

wherein R¹ and R⁵ are as defined above in connection with Scheme 4.

Disubstituted acetylenes such as (XXX) are readily prepared by a palladium catalyzed coupling reaction between aryl acetylenes and 2-halopyridines using methods described in the literature (Yamanake et al, *Chem. Pharm. Bull.* 1988, 1890). A compound of formula (XII) can be brominated to give a compound of formula (XXII) as outlined previously.

As will be apparent to those skilled in the art, the compounds of formula (I) may be converted to other compounds of formula (I) using techniques well known in the art. For example, one method of converting compounds of formula (I) to other compounds of formula (I) comprises a) oxidizing the compound of formula (I-A) to prepare a compound of formula (I-B) and then b) optionally reacting a compound of formula (I-B) with an oxygen or amine nucleophile of formula R², wherein R² is selected from the group consisting of —NR⁷R⁸, —OR⁷, —OAy, Het attached through N, —NH(CH₂)$_m$Het and —O(CH₂)$_m$Het to produce a compound of formula I wherein R² is selected from the group consisting of —NR⁷R⁸, —OR⁷, —OAy, Het attached through N, —NH(CH₂)$_m$Het and —O(CH₂)$_m$Het.

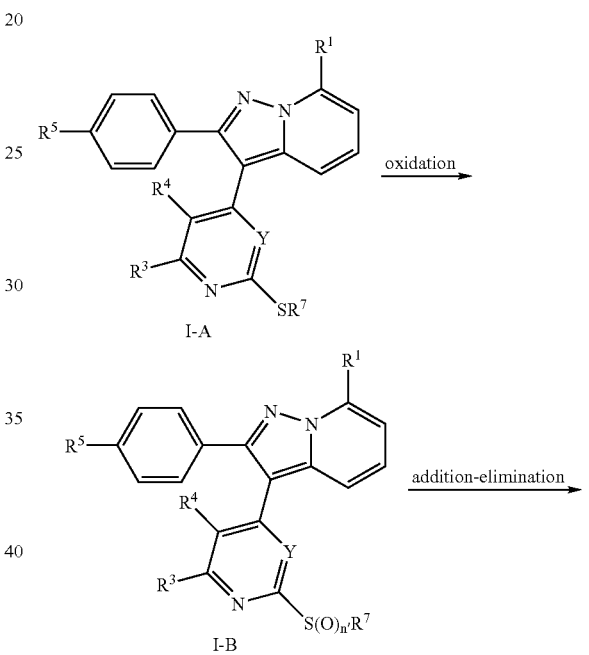

wherein n' is 1 or 2 and all other variables are as defined according to any of the processes described above.

More specifically, compounds of formula (I) wherein Y is N or CH can be prepared by reacting a compound of formula (I-B) (i.e., compounds of formula I wherein R² is S(O)$_{n'}$R⁷ where n' is 1 or 2) with an oxygen or amine nucleophile of formula R², wherein R² is selected from the group consisting of —NR⁷R⁸, —OR⁷, —OAy, Het attached through N, —NH(CH₂)$_m$Het and —O(CH₂)$_m$Het. The reaction may be carried out neat or in a suitable solvent and may be heated to 50–150° C. Typically the solvent is a lower alcohol such as methanol, ethanol, isopropanol or the like, or solvent such as N,N-dimethylformamide or tetrahydrofuran, or the like. Optionally a base may be used to facilitate the reaction. Typically the base can be potassium carbonate, or an amine base such as triethylamine.

Compounds of formula (I-B) may be conveniently prepared by reacting a compound of formula (I-A) (i.e., compounds of formula I wherein $R^2$ is $S(O)_n R^7$ where n is 0) with an oxidizing agent in an inert solvent, optionally in the presence of a base.

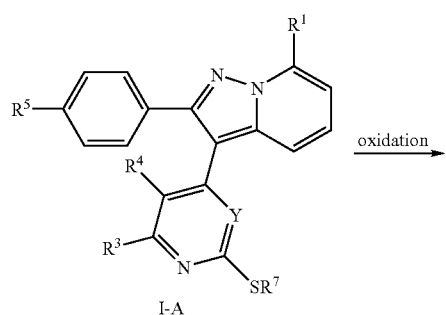

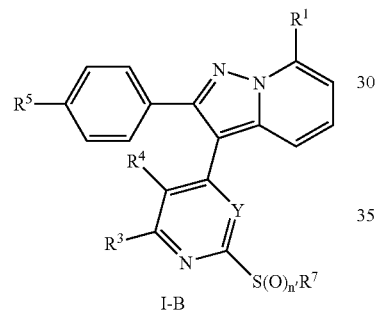

wherein the variables are as defined above.

Typically the oxidizing agent is a peracid such as m-chloroperbenzoic acid or the like optionally with a base such as sodium bicarbonate. Careful monitoring of the stoichiometry between the oxidizing agent and the substrate allows the product distribution between sulfoxide (n'=1), and sulfone (n'=2) to be controlled. Suitable solvents include but are not limited to, dichloromethane, chloroform or the like.

Compounds of formula (I-A) are prepared by methods described above wherein $R^2$=$SR^7$ from from the reaction of compounds selected from the group consisting of compounds of formula (XVI), compounds of formula (IX) and compounds of formula (XX) with a compound of formula (X-A) (i.e., the compound of formula (X) wherein $R^2$ is $SR^7$). The requisite compound of formula (X-A) can be obtained from commercial sources or prepared by methods known to one skilled in the art.

Another particularly useful method for converting compounds of formula (I) to other compounds of formula (I) comprises reacting a compound of formula (I-C) (i.e., a compound of formula (I) wherein $R^2$ is fluoro) with an amine, and optionally heating the mixture to 50–150° C. to prepare a compound of formula (I-D) (i.e., a compound of formula (I) wherein $R^2$ is —$NR^7R^8$).

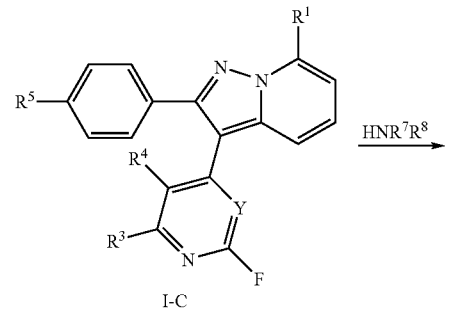

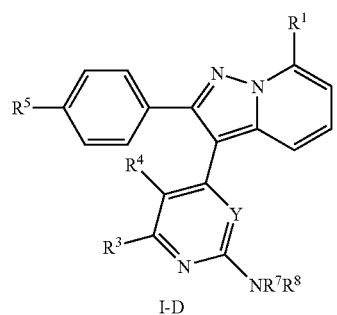

wherein all variables are as defined in connection with any of the processes described above.

This procedure may be carried out by mixing a compound of formula (I-C) in an amine neat, or in a suitable solvent with an excess of amine to produce a compound of formula (I-D). Typically the solvent is a lower alcohol such as methanol, ethanol, isopropanol or the like. Other suitable solvents may include N,N-dimethylformamide, 1-methyl-2-pyrrolidine or the like.

As a further example, compounds of formula (I-E) may be converted to compounds of formula (I-F) using either of two methods.

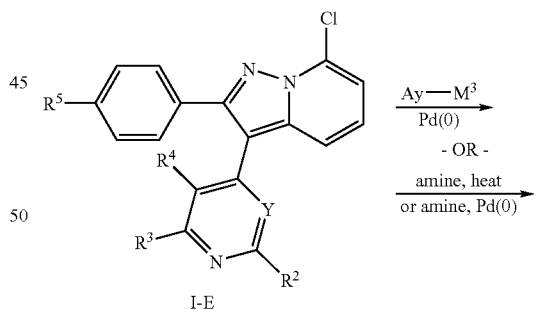

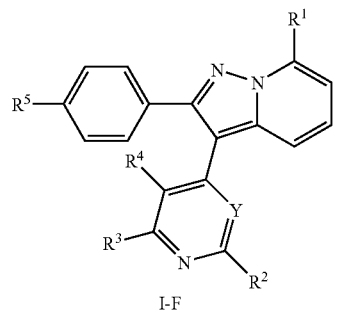

wherein $M^3$ is $B(OH)_2$, $B(ORa)_2$, $Sn(Ra)_3$, Zn-halide, Zn—Ra or Mg-halide where Ra is alkyl or cycloalkyl, halide is halo and all other variables are as defined in connection with any process described above.

Such method can be carried out using the reaction and conditions described above in connection with Scheme 1 and the conversion of compounds of formula VII to compounds of formula VIII. Thus, the present invention provides a process for converting compounds of formula (I-E) to compounds of formula (I-F) which comprises either: (1) replacing the C-7 halogen of the compound of formula (I-E) with an amine; or (2) coupling the compound of formula (I-E) with an aryl metal of the formula Ay-$M^3$ where $M^3$ is $B(OH)_2$, $B(ORa)_2$, $B(Ra)_2$, $Sn(Ra)_3$, Zn-halide; Zn—Ra or Mg-halide.

Based upon this disclosure and the examples contained herein one skilled in the art can readily convert compounds of formula (I) or a pharmaceutically acceptable salt, solvate, or physiologically functional derivative thereof into other compounds of formula (I), or salts, solvates or physiologically functional derivatives thereof.

The present invention also provides radiolabeled compounds of formula (I). Radiolabeled compounds of formula (I) can be prepared using conventional techniques. For example, radiolabeled compounds of formula (I) can be prepared by reacting the compound of formula (I) with tritium gas in the presence of an appropriate catalyst to produce radiolabeled compounds of formula (I).

In one preferred embodiment, the compounds of formula (I) are tritiated.

The radiolabeled compounds of formula (I) are useful in assays for the identification of compounds for the treatment or prophylaxis of viral infections such as herpes viral infections. Accordingly, the present invention provides an assay method for identifying compounds which have activity for the treatment or prophylaxis of viral infections such as herpes viral infections, which method comprises the step of specifically binding the radiolabeled compound of formula (I) to the target protein. More specifically, suitable assay methods will include competition binding assays. The radiolabeled compounds of formula (I) can be employed in assays according to the methods conventional in the art.

The following examples are intended for illustration only and are not intended to limit the scope of the invention in any way. Reagents are commercially available or are prepared according to procedures in the literature. Example numbers refer to those compounds listed in the tables above. $^1$H and $^{13}$C NMR spectra were obtained on Varian Unity Plus NMR spectrophotometers at 300 or 400 MHz, and 75 or 100 MHz respectively. $^{19}$F NMR were recorded at 282 MHz. Mass spectra were obtained on Micromass Platform, or ZMD mass spectrometers from Micromass Ltd. Altrincham, UK, using either Atmospheric Chemical Ionization (APCI) or Electrospray Ionization (ESI). Analytical thin layer chromatography was used to verify the purity of some intermediates which could not be isolated or which were too unstable for full characterization, and to follow the progress of reactions. Unless otherwise stated, this was done using silica gel (Merck Silica Gel 60 F254). Unless otherwise stated, column chromatography for the purification of some compounds, used Merck Silica gel 60 (230–400 mesh), and the stated solvent system under pressure. All compounds were characterized as their free-base form unless otherwise stated. On occasion the corresponding hydrochloride salts were formed to generate solids where noted.

EXAMPLE 1

N-cyclopentyl-3-[2-(cyclopentylamino)-4-pyrimidinyl]-2-(4-fluorophenyl)pyrazolo[1,5-α]pyridin-7-amine

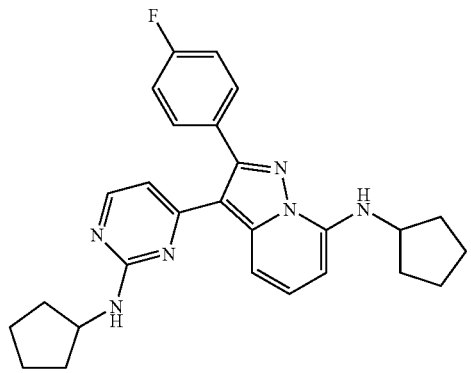

a) 2-(6-Chloro-2-pyridinyl)-1-(4-fluorophenyl)ethanone

To a cold (0° C.) solution of 6-chloro-2-picoline (21.4 mL, 196.0 mmol) and ethyl 4-fluorobenzoate (57.5 mL, 391.2 mmol) in tetrahydrofuran (311 mL) was added lithium bis(trimethylsilyl)amide (391 mL, 1.0 M in tetrahydrofuran, 391.0 mmol) dropwise via a pressure equalizing funnel over 1 hour. Upon complete addition, the cold bath was removed and the resultant solution was heated to 45° C. for 15 hours. The mixture was cooled to room temperature and quenched by the addition of water. Ether was added and the organic layer was washed with brine. The aqueous layer was extracted with ether and the combined organics were dried over magnesium sulfate. Filtration and concentration gave a solid residue which was purified by recrystallization from ethyl acetate-hexanes to provide 2-(6-chloro-2-pyridinyl)-1-(4-fluorophenyl)ethanone (32.2 g, 66%) as a tinted off-white solid existing as a keto-enol tautomeric mixture. $^1$H NMR (CDCl$_3$): for the keto tautomer δ 8.11 (m, 2H), 7.66 (t, 1H), 7.30–7.25 (m 2H), 7.17 (t, 2H), 4.48 (s 2H), $^{19}$F NMR (CDCl$_3$) δ −104.72 (keto), −111.64 (enol); MS m/z 250 (M+1).

b) 2-(6-Chloro-2-pyridinyl)-1-(4-fluorophenyl)ethanone oxime

To a solution of 2-(6-chloro-2-pyridinyl)-1-(4-fluorophenyl)ethanone (74.9 g, 299.8 mmol) in methanol (900 mL) was added hydroxylamine hydrochloride (104 g, 1.49 mol) followed by sodium hydroxide (600 mL, 10% aqueous, 1.5 mol). The resultant suspension was heated to reflux for 2 hours and then cooled to room temperature. The mixture was concentrated in vacuo and the residue taken up in ether and water. The organic layer was washed with brine. The aqueous layer was extracted with ether and the combined organics were dried over magnesium sulfate. Filtration and concentration gave a solid residue which was purified by recrystallization from ethyl acetate-hexanes to provide 2-(6-chloro-2-pyridinyl)-1-(4-fluorophenyl)ethanone oxime (67.9 g, 86%) as a white solid. $^1$H NMR (CDCl$_3$): δ 8.69 (s, 1H), 7.71 (dd, 2H), 7.53 (t, 1H), 7.18–7.16 (m, 2H), 7.03 (t, 2H), 4.37 (s, 2H); $^{19}$F NMR (CDCl$_3$) δ −111.77; MS m/z 265 (M+1).

c) 7-Chloro-2-(4-fluorophenyl)pyrazolo[1,5-α]pyridine

To a solution of 2-(6-chloro-2-pyridinyl)-1-(4-fluorophenyl)ethanone oxime (109.2 g, 414 mmol) in 1,2-dimethoxyethane (500 mL) at 0° C. was added trifluoroacetic anhydride (59 mL, 414 mmol), keeping the temperature below 10° C. After the addition was complete, the reaction was warmed to 15° C. The solution was then cooled to 4° C. and a solution of triethylamine (116 mL, 828 mmol) in 1,2-dimethoxyethane (60 mL) was added over 0.5 hours. After warming to room temperature, the mixture was stirred for 1.5 hours. To this was added iron(II) chloride (0.52 g, 4.1 mmol) and the reaction was heated to reflux for 3 hours. The reaction was concentrated and the resulting solid was recrystallized from ethyl acetate-hexanes to give 7-chloro-2-(4-fluorophenyl)pyrazolo[1,5-α]pyridine (69.7 g, 68%) as off-white needles. $^1$H NMR (CDCl$_3$): δ 8.03 (m, 2H), 7.54 (d, 1H), 7.16 (m, 3H), 6.93 (d, 1H), 6.91 (s, 1H); MS m/z 247 (M+1); mp 156–157° C.

d) 1-[7-Chloro-2-(4-fluorophenyl)pyrazolo[1,5-α]pyridin-3-yl]ethanone

To a solution of 7-chloro-2-(4-fluorophenyl)pyrazolo[1,5-α]pyridine (10.0 g, 40.5 mmol) in toluene (225 mL) at room temperature was added acetic anhydride (4.6 mL, 48.6 mmol). Boron trifluoride diethyletherate (5.6 mL, 44.6 mmol) was then added dropwise and the resultant solution was heated to reflux for 3.5 hours. The reaction mixture was cooled to room temperature and quenched by the dropwise addition of aqueous sodium bicarbonate. Ether was added and the organic layer was washed with brine. The aqueous layer was extracted with ether and the combined organics were dried over magnesium sulfate, filtered and concentrated. The residue was purified by recrystallization from ethyl acetate-hexanes to give 1-[7-chloro-2-(4-fluorophenyl)pyrazolo[1,5-α]pyridin-3-yl]ethanone (9.0 g, 77%) as redish needles. $^1$H NMR (CDCl$_3$): δ 8.41 (d, 1H), 7.59 (m, 2H), 7.45 (dd, 1H), 7.26–7.13 (m 3H), 2.15 (s, 3H); $^{19}$F NMR (CDCl$_3$) δ −112.06; MS m/z 289 (M+1).

e) 1-[7-(Cyclopentylamino)-2-(4-fluorophenyl)pyrazolo[1,5-α]pyridin-3-yl]ethanone To a solution of 1-[7-chloro-2-(4-fluorophenyl)pyrazolo[1,5-α]pyridin-3-yl]ethanone (2.7 g, 9.5 mmol) in toluene (50 mL) was added successively racemic-BINAP (378 mg, 0.6 mmol), cesium carbonate (4.7 g, 14.3 mmol), cyclopentylamine (4.7 mL, 47.5 mmol), and palladium (II) acetate (86 mg, 0.4 mmol). The resultant mixture was heated to 95° C. for 2.5 hours at which time the reaction was judged complete by thin layer chromatography. The solution was cooled to room temperature and ether was added. The organic layer was washed with water and brine. The aqueous layer was extracted with ether and the combined organics dried over magnesium sulfate. Filtration and concentration followed by flash chromatography (4:1 hexanes-ethyl acetate) provided 1-[7-(cyclopentylamino)-2-(4-fluorophenyl)pyrazolo[1,5-α]pyridin-3-yl]ethanone (3.1 g, 95%) as a yellow solid. $^1$H NMR (CDCl$_3$): δ 7.62 (d, 1H), 7.55 (dd, 2H), 7.40 (t, 1H), 7.15 (t, 2H), 6.10 (d, 1H), 5.99 (d, 1H), 3.94 (m, 1H), 2.09 (s, 3H), 2.12–2.04 (m, 2H), 1.78–1.58 (m, 6H); $^{13}$C NMR (CDCl$_3$) δ 192.63, 163.28 (d, J$_{CF}$=247.3 Hz), 154.89, 142.65, 142.38, 131.66 (d, J$_{CF}$=8.3 Hz) 131.09, 130.03 (d, J$_{CF}$=3.8 Hz), 115.33 (d, J$_{CF}$=22.0 Hz), 111.32, 105.41, 91.97, 53.81, 33.21, 30.10, 23.96; $^{19}$F NMR (CDCl$_3$) δ −112.70; MS m/z 338 (M+1).

f) (2E)-1-[7-(Cyclopentylamino)-2-(4-fluorophenyl)pyrazolo[1,5-α]pyridin-3-yl]-3-(dimethylamino)-2-propen-1-one A solution of 1-[7-(cyclopentylamino)-2-(4-fluorophenyl)pyrazolo[1,5-α]pyridin-3-yl]ethanone (3.1 g, 9.2 mmol) in N,N-dimethylformamide dimethyl acetal (25 mL) was heated to reflux for 6 days. The mixture was cooled to room temperature, ethyl acetate was added followed by water. The organic layer was washed with brine. The aqueous layer was extracted with ethyl acetate and the combined organics were dried over magnesium sulfate. Filtration and concentration followed by flash chromatography (ethyl acetate) provided (2E)-1-[7-(cyclopentylamino)-2-(4-fluorophenyl)pyrazolo[1,5-α]pyridin-3-yl]-3-(dimethylamino)-2-propen-1-one (3.6 g, 99%) as a tinted oil: $^1$H NMR (CDCl$_3$): δ 7.73–7.61 (m, 4H), 7.32 (t, 1H), 7.14 (t, 2H), 6.03 (d, 1H), 5.96 (d, 1H), 5.05 (d, 1H), 3.99 (m, 1H), 5.15–2.42 (broad, 6H), 2.19–2.08 (m, 2H), 1.86–1.62 (m, 6H); $^{19}$F NMR (CDCl$_3$) δ −113.75; MS m/z 393 (M+1).

g) N-Cyclopentylguanidine hydrochloride (prepared by modification of a procedure from Bannard, R. A. B.; Casselman, A. A.; Cockburn, W. F.; and Brown, G. M. Can. J. Chem. 1958, 36, 1541–1549). To a solution of 2-methyl-2-thiopseudourea sulfate (13.9 g, 50.0 mmol) in water (40 mL) was added cyclopentylamine (14.8 mL, 150 mmol). The resultant mixture was heated to 55° C. for 20 minutes and then to reflux for 2.5 hours. The mixture was cooled to room temperature and concentrated in vacuo and azeotroped with methanol. Water was added (~100 mL) and Amberlite IRA 400 (Cl$^-$) resin was added. The mixture was stirred for 1 hour and then the resin was removed by filtration. The solution was concentrated in vacuo and azeotroped with methanol. The residue was recrystallized from methanol-acetone to yield N-cyclopentylguanidine hydrochloride (7.0 g, 86%) as a fine white solid. $^1$H NMR (D$_2$O): δ 3.62 (m, 1H), 1.75 (m, 2H), 1.52–1.32 (m, 6H); $^{13}$C NMR (D$_2$O) δ 156.23, 53.11, 32.15, 23.13; MS m/z 128 (M+1).

h) N-Cyclopentyl-3-[2-(cyclopentylamino)-4-pyrimidinyl]-2-(4-fluorophenyl)pyrazolo[1,5-α]pyridin-7-amine To a solution of (2E)-1-[7-(cyclopentylamino)-2-(4-fluorophenyl)pyrazolo[1,5-α]pyridin-3-yl]-3-(dimethylamino)-2-propen-1-one (3.5 g, 8.9 mmol) in tetrahydrofuran (36 mL, 0.25 M) was added N-cyclopentylguanidine hydrochloride (1.89 g, 11.6 mmol), followed by solid potassium tert-butoxide (2.6 g, 23.2 mmol) in two portions. The resultant solution was heated to reflux for 23 hours. Upon cooling to room temperature, ether was added followed by water. The organics were washed with brine, and the aqueous layer was extracted with ether. The combined organics were dried over magnesium sulfate, filtered and concentrated in vacuo. The residue was purified by flash chromatography on silica to give N-cyclopentyl-3-[2-(cyclopentylamino)-4-pyrimidinyl]-2-(4-fluorophenyl)pyrazolo[1,5-α]pyridin-7-amine (3.7 g, 91%) as an off white solid. $^1$H NMR (CDCl$_3$): δ 7.97 (d, 1H), 7.68 (d, 1H), 7.59 (dd, 2H), 7.27 (t, 1H), 7.10 (t, 2H), 6.24 (d, 1H), 5.99 (d, 1H), 5.96 (d, 1H), 5.01 (d, 1H), 4.28 (m, 1H), 3.97 (m, 1H), 2.12–1.99 (m, 4H), 1.79–1.44 (m, 12H); $^{13}$C NMR (CDCl$_3$) δ 163.12 (d, $J_{CF}$=246.6 Hz), 162.09, 161.53, 156.67, 152.15, 142.66, 141.09, 131.46 (d, $J_{CF}$=8.0 Hz), 129.92 (d, $J_{CF}$=3.1 Hz), 128.39, 115.45(d, $J_{CF}$=21.3 Hz), 108.68, 107.13, 105.15, 90.13, 53.84, 52.87, 33.50, 33.30, 24.05, 23.70; $^{19}$F NMR (CDCl$_3$) δ −113.49; MS m/z 457 (M+1); Anal. Calcd for C$_{27}$H$_{29}$FN$_6$: C, 71.03; H, 6.40; N, 18.41. Found: C, 71.20; H, 6.37; N, 18.52.

EXAMPLE 2

2-(4-Bromophenyl)-N-butyl-3-[2-(butylamino)-4-pyrimidinyl]pyrazolo[1,5-α]pyridin-7-amine

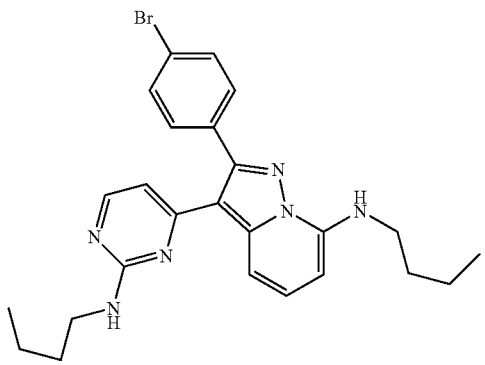

a) 1-(4-Bromophenyl)-2-(6-chloro-2-pyridinyl)ethanone

In a similar manner as described in Example 1, from ethyl 4-bromobenzoate (12.8 mL, 78.3 mmol) and 6-chloro-2-picoline (4.3 mL, 39.2 mmol), 1-(4-bromophenyl)-2-(6-chloro-2-pyridinyl)ethanone (9.6 g, 82%) was obtained as a crystalline solid existing as a keto-enol tautomeric mixture. $^1$H NMR (CDCl$_3$): for the keto tautomer δ 7.95 (d, 2H), 7.74–7.56 (m, 3H), 7.27 (m, 2H), 4.47 (s, 2H); MS m/z 310 (M+1).

b) 1-(4-Bromophenyl)-2-(6-chloro-2-pyridinyl)ethanone oxime

In a similar manner as described in Example 1, from 1-(4-bromophenyl)-2-(6-chloro-2-pyridinyl)ethanone (9.5 g, 30.6 mmol) was obtained 1-(4-bromophenyl)-2-(6-chloro-2-pyridinyl)ethanone oxime (10.0 g, 99%) as a white solid. $^1$H NMR (CDCl$_3$): δ 9.78 (broad, 1H), 7.74–7.47 (m, 5H), 7.21–7.17 (m, 2H), 4.39 (s, 2H); MS m/z 325 (M+1).

c) 2-(4-Bromophenyl)-7-chloropyrazolo[1,5-α]pyridine

In a similar manner as described in Example 1, from 1-(4-bromophenyl)-2-(6-chloro-2-pyridinyl)ethanone oxime (45.2 g, 139 mmol), 2-(4-bromophenyl)-7-chloropyrazolo[1,5-α]pyridine (30.5 g, 72%) was obtained as a pale yellow crystalline solid. $^1$H NMR (CDCl$_3$): δ 7.85 (dd, 2H), 7.54 (dd, 2H), 7.46 (d, 1H), 7.04 (m, 1H), 6.87 (m, 2H); MS m/z 307 (M+1).

d) 1-[2-(4-Bromophenyl)-7-chloropyrazolo[1,5-α]pyridin-3-yl]ethanone

In a similar manner as described in Example 1, from 2-(4-bromophenyl)-7-chloropyrazolo[1,5-α]pyridine (10.0 g, 32.5 mmol), 1-[2-(4-bromophenyl)-7-chloropyrazolo[1,5-α]pyridin-3-yl]ethanone (7.63 g, 67%) was obtained as pink needles. $^1$H NMR (CDCl$_3$): δ 8.37 (d, 1H), 7.62 (d, 2H), 7.43 (m, 3H), 7.14 (d, 1H), 2.13 (s, 3H); MS m/z 349 (M+1).

e) 1-[2-(4-Bromophenyl)-7-(butylamino)pyrazolo[1,5-α]pyridin-3-yl]ethanone

In a similar manner as described in Example 1, from 1-[2-(4-bromophenyl)-7-chloropyrazolo[1,5-α]pyridin-3-yl]ethanone (2.55 g, 7.3 mmol), 1-[2-(4-bromophenyl)-7-(butylamino)pyrazolo[1,5-α]pyridin-3-yl]ethanone (2.15 g, 76%) was obtained as a yellow oil. $^1$H NMR (CDCl$_3$): δ 7.61 (m, 3H), 7.43 (m, 3H), 6.08 (d, 1H), 6.02 (bs, 1H), 3.33 (q, 2H), 2.12 (s, 3H), 1.70 (m, 2H), 1.44 (m, 2H), 0.94 (t, 3H); MS m/z 386 (M+1).

f) (2E)-1-[2-(4-Bromophenyl)-7-(butylamino)pyrazolo[1,5-α]pyridin-3-yl]-3-(dimethylamino)-2-propen-1-one In a similar manner as described in Example 1, from 1-[2-(4-bromophenyl)-7-(butylamino)pyrazolo[1,5-α]pyridin-3-yl]ethanone (5.5 g, 14.2 mmol), (2E)-1-[2-(4-bromophenyl)-7-(butylamino)pyrazolo[1,5-α]pyridin-3-yl]-3-(dimethylamino)-2-propen-1-one (5.78 g, 92%) was obtained as a brown oil. $^1$H NMR (CDCl$_3$): δ 7.57 (m, 6H), 7.28 (t, 1H), 5.95 (m, 2H), 5.03 (d, 1H), 3.32 (q, 2H), 2.92 (bs, 3H), 2.52 (bs, 3H), 1.71 (m, 2H), 1.44 (m, 2H), 0.94 (t, 3H); MS m/z 441 (M+1).

g) 2-(4-Bromophenyl)-N-butyl-3-[2-(butylamino)-4-pyrimidinyl]pyrazolo[1,5-α]pyridin-7-amine In a similar manner as described in Example 1, from (2E)-1-[2-(4-bromophenyl)-7-(butylamino)pyrazolo[1,5-α]pyridin-3-yl]-3-(dimethylamino)-2-propen-1-one (5.78 g, 13.1 mmol) and N-butylguanidine sulfate (Weiss, S.; Krommer, H. Chem.-Zgt. 1974, 98, 617–618) was obtained 2-(4-bromophenyl)-N-butyl-3-[2-(butylamino)-4-pyrimidinyl] pyrazolo[1,5-α]pyridin-7-amine (5.18 g, 80%) as a pale yellow solid. $^1$H NMR (CDCl$_3$): δ 7.98 (d, 1H), 7.71 (d, 1H), 7.56 (m, 4H), 7.33 (t, 1H), 6.35 (d, 1H), 6.03 (m, 2H), 3.46 (q, 2H), 3.38 (q, 2H), 1.81–1.40 (m, 8H), 0.98 (m, 6H); MS m/z 493 (M+1).

EXAMPLE 3

N-Butyl-3-[2-(butylamino)-4-pyrimidinyl]-2-(4-fluorophenyl)pyrazolo-[1,5-α]pyridin-7-amine

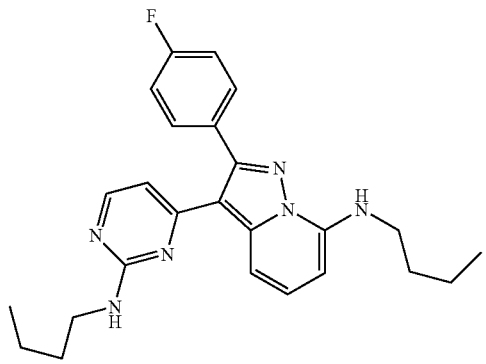

a) 1-[7-(Butylamino)-2-(4-fluorophenyl)pyrazolo[1,5-α]pyridin-3-yl]ethanone

A mixture of 1-[7-chloro-2-(4-fluorophenyl)pyrazolo[1,5-α]pyridin-3-yl]ethanone (969 mg, 3.4 mmol) and potassium carbonate (9.6 g, 69.4 mmol) in n-butylamine (20 mL) was heated to reflux for 5 hours. The mixture was cooled to room temperature and concentrated in vacuo. The residue was taken up in ethyl acetate and water. The organic layer was washed with brine. The aqueous layer was extracted with ethyl acetate and the combined organics were dried over sodium sulfate. Filtration and concentration followed by flash chromatography (2:1 hexanes-ethyl acetate) provided 1-[7-(butylamino)-2-(4-fluorophenyl)pyrazolo[1,5-α]pyridin-3-yl]ethanone (921 mg, 84%) as a tinted oil. $^1$H NMR (CDCl$_3$): δ 7.71 (d, 1H), 7.63 (dd, 2H), 7.49 (t, 1H), 7.23 (t, 2H), 6.16 (d, 1H), 6.10 (m, 1H), 3.40 (m, 2H), 2.18 (s, 3H), 1.78 (m, 2H), 1.52 (m, 2H), 1.02 (t, 3H); MS m/z 326 (M+1); R$_f$ 0.6 (1:1 hexanes:ethyl acetate).

b) (2E)-1-[7-(Butylamino)-2-(4-fluorophenyl)pyrazolo[1,5-α]pyridin-3-yl]-3-(dimethylamino)-2-propen-1-one In a similar manner as described in Example 1, from 1-[7-(butylamino)-2-(4-fluorophenyl)pyrazolo[1,5-α]pyridin-3-yl]ethanone (880 mg, 2.7 mmol) was formed (2E)-1-[7-(butylamino)-2-(4-fluorophenyl)pyrazolo[1,5-α]pyridin-3-yl]-3-(dimethylamino)-2-propen-1-one (971 mg, 95%) as yellow foam. $^1$H NMR (CDCl$_3$): δ 7.67 (dd, 2H), 7.60 (d, 1H), 7.53 (d, 1H), 7.27 (t, 1H), 7.09 (t, 2H), 5.96–5.93 (m 2H), 5.01 (d, 1H), 3.30 (m, 2H), 3.10–2.30 (broad, 6H), 1.69 (m, 2H), 1.43 (m, 2H), 0.93 (t, 3H); MS m/z 381 (M+1).

c) N-Butyl-3-[2-(butylamino)-4-pyrimidinyl]-2-(4-fluorophenyl)pyrazolo[1,5-α]pyridin-7-amine In a similar manner as described in Example 1, from (2E)-1-[7-(butylamino)-2-(4-fluorophenyl)pyrazolo[1,5-α]pyridin-3-yl]-3-(dimethylamino)-2-propen-1-one (34 mg, 0.09 mmol), N-butylguanidine sulfate and potassium carbonate in N,N-dimethylformamide was obtained N-butyl-3-[2-(butylamino)-4-pyrimidinyl]-2-(4-fluorophenyl)pyrazolo[1,5-α]pyridin-7-amine (33 mg, 85%) as a yellow solid. $^1$H NMR (CDCl$_3$): δ 7.98 (d, 1H), 7.68 (d, 1H), 7.59 (m, 2H), 7.27 (t, 1H), 7.10 (t, 2H), 6.25 (d, 1H), 6.00–5.96 (m, 2H), 5.05 (m, 1H), 3.41 (m, 2H), 3.33 (m, 2H), 1.71 (m, 2H), 1.60 (m, 2H), 1.50–1.36 (m, 4H), 0.97–0.91 (m, 6H); MS m/z 433 (M+1); R$_f$ 0.67 (1:1 hexanes-ethyl acetate).

EXAMPLE 4

N-Butyl-3-[2-(cyclopropylamino)-4-pyrimidinyl]-2-(4-fluorophenyl)-pyrazolo[1,5-α]pyridin-7-amine

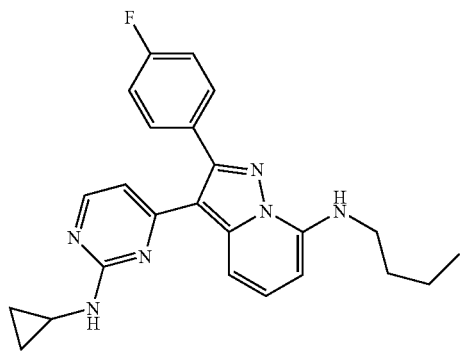

In a similar manner as described in Example 1, from (2E)-1-[7-(butylamino)-2-(4-fluorophenyl)pyrazolo[1,5-α]pyridin-3-yl]-3-(dimethylamino)-2-propen-1-one (71 mg, 0.19 mmol), N-cyclopropylguanidine sulfate and potassium carbonate in dimethylformamide was obtained N-butyl-3-[2-(cyclopropylamino)-4-pyrimidinyl]-2-(4-fluorophenyl)pyrazolo[1,5-α]pyridin-7-amine (57 mg, 73%) as a white solid. $^1$H NMR (CDCl$_3$): δ 8.09 (d, 1H), 7.92 (d, 1H), 7.67 (dd, 2H), 7.34 (t, 1H), 7.18 (t, 2H), 6.37 (d, 1H), 6.09–6.04 (m, 2H), 5.53 (broad, 1H), 3.40 (m, 2H), 2.88 (m, 1H), 1.79 (m, 2H), 1.52 (m, 2H), 1.02 (t, 3H), 0.88 (m, 2H), 0.64 (m, 2H); MS m/z 417 (M+1); R$_f$ 0.55 (1:1 hexanes:ethyl acetate).

EXAMPLE 5

N-Butyl-2-(4-fluorophenyl)-3-[2-(1-pyrrolidinyl)-4-pyrimidinyl]pyrazolo[1,5-α]pyridin-7-amine

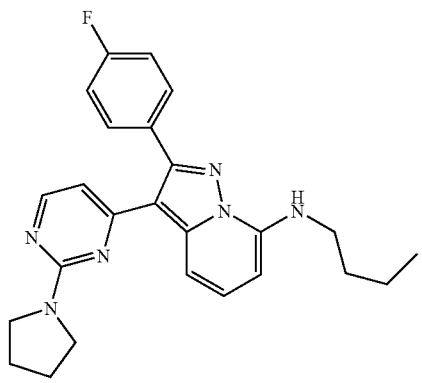

In a similar manner as described in Example 1, from (2E)-1-[7-(butylamino)-2-(4-fluorophenyl)pyrazolo[1,5-α]pyridin-3-yl]-3-(dimethylamino)-2-propen-1-one (70 mg, 0.18 mmol), 1-pyrrolidinecarboximidamide sulfate and potassium carbonate in dimethylformamide was obtained N-butyl-2-(4-fluorophenyl)-3-[2-(1-pyrrolidinyl)-4-pyrimidinyl]pyrazolo[1,5-α]pyridin-7-amine (64 mg, 81%) as a yellow solid. $^1$H NMR (CDCl$_3$): δ 8.03 (d, 1H), 7.76 (d, 1H), 7.59 (m, 2H), 7.26 (t, 1H), 7.09 (t, 2H), 6.20 (d, 1H), 5.99–5.95 (m, 2H), 3.61 (m, 4H), 3.32 (m, 2H), 1.98 (m, 4H), 1.70 (m, 2H), 1.44 (m, 2H), 0.94 (t, 3H); $^{13}$C NMR (CDCl$_3$) δ 163.07 (d, J$_{CF}$=246.5 Hz), 161.04, 160.48, 156.56, 152.19, 143.01, 141.13, 131.45 (d, J$_{CF}$=8.4 Hz), 130.05 (d, J$_{CF}$=3.0 Hz), 128.34, 115.38 (d, J$_{CF}$=21.2 Hz), 107.46, 107.22, 105.50, 89.19, 46.59, 42.33, 31.11, 25.55, 20.19, 13.75; MS m/z 431 (M+1).

EXAMPLE 6

N-Butyl-3-[2-(cyclopentylamino)-4-pyrimidinyl]-2-(4-fluorophenyl)pyrazolo[1,5-α]pyridin-7-amine

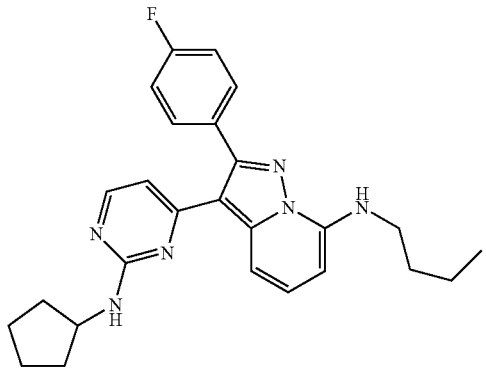

In a similar manner as described in Example 1, from (2E)-1-[7-(butylamino)-2-(4-fluorophenyl)pyrazolo[1,5-α]pyridin-3-yl]-3-(dimethylamino)-2-propen-1-one (258 mg, 0.68 mmol) was obtained N-butyl-3-[2-(cyclopentylamino)-4-pyrimidinyl]-2-(4-fluorophenyl)pyrazolo[1,5-α]pyridin-7-amine (260 mg, 87%) as a yellow solid. $^1$H NMR (CDCl$_3$): δ 8.01 (d, 1H), 7.73 (d, 1H), 7.62 (m, 2H), 7.29 (t, 1H), 7.12 (t, 2H), 6.28 (d, 1H), 6.05 (m, 1H), 5.98 (d, 1H), 5.27 (broad, 1H), 4.32 (m, 1H), 3.34 (m, 2H), 2.10–2.00 (m, 2H), 1.77–1.41 (m, 10H), 0.97 (t, 3H); $^{13}$C NMR (CDCl$_3$) δ 163.03 (d, J$_{CF}$=244.5 Hz), 162.14, 161.41, 156.74, 152.10, 142.99, 141.02, 131.36 (d, J$_{CF}$=8.0 Hz) 129.92 (d, J$_{CF}$=3.0 Hz), 128.31, 115.36 (d, J$_{CF}$=21.0 Hz), 108.58, 107.9, 105.17, 89.21, 52.79, 42.27, 33.40, 31.06, 23.65, 20.13, 13.70; $^{19}$F NMR (CDCl$_3$) δ −113.42; MS m/z 445 (M+1).

EXAMPLE 7

4-[7-Chloro-2-(4-fluorophenyl)pyrazolo[1,5-α]pyridin-3-yl]-N-cyclopentyl-6-methyl-2-pyrimidinamine

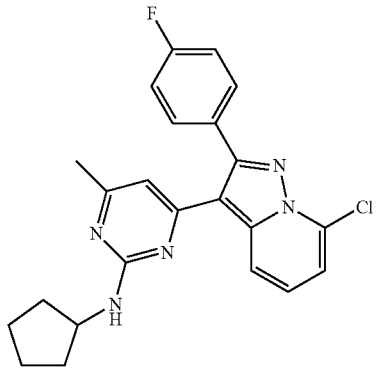

a) 7-Chloro-2-(4-fluorophenyl)pyrazolo[1,5-α]pyridine-3-carbaldehyde

N,N-Dimethylformamide (100 mL) was cooled to 0° C. and treated with phosphorous oxychloride (5.7 mL, 60.8 mmol). After the addition was complete, the mixture was warmed to room temperature and stirred for 1 hour. To this was added 7-chloro-2-(4-fluorophenyl)pyrazolo[1,5-α]pyridine (10.0 g, 40.5 mmol) and the resultant solution was stirred overnight. Water was added, followed by dichloromethane. The aqueous layer was extracted with dichloromethane. The combined organics were washed with brine, dried over magnesium sulfate, filtered and concentrated. The residue was recrystallized from diethyl ether and hexanes to give 7-chloro-2-(4-fluorophenyl)pyrazolo[1,5-α]pyridine-3-carbaldehyde (10.6 g, 95%) as a fluffy white solid. $^1$H NMR (CDCl$_3$): δ 10.07 (s, 1H), 8.37 (d, 1H), 7.78 (m, 2H), 7.48 (t, 1H), 7.20 (m, 3H); $^{19}$F NMR (CDCl$_3$) δ −111.25; MS m/z 275 (M+1); Anal. Calcd for C$_{14}$H$_8$ClFN$_2$O: C, 61.22; H, 2.94; N, 10.20. Found: C, 61.34; H, 2.90; N, 10.15; mp 212–213° C. (decomp.).

b) 1-[7-Chloro-2-(4-fluorophenyl)pyrazolo[1,5-α]pyridin-3-yl]-2-butyn-1-ol

To a cold (−78° C.) suspension of 7-chloro-2-(4-fluorophenyl)pyrazolo[1,5-α]pyridine-3-carbaldehyde (1.50 g, 5.47 mmol) in tetrahydrofuran (10 mL) was added 1-propynyl magnesium bromide (12.0 mL, 0.5 M in tetrahydrofuran, 6.02 mmol) dropwise. The reaction mixture was stirred at −78° C. for 1 hour, then at 0° C. for 2 hours. The resultant solution was poured into saturated aqueous sodium bicarbonate and extracted with ethyl acetate. The organic layer was washed with water and brine and the combined organics were dried over magnesium sulfate. Filtration and concentration followed by flash chromatography (4:1 hexanes:ethyl acetate to 1:1 hexanes:ethyl acetate) provided 1-[7-chloro-2-(4-fluorophenyl)pyrazolo[1,5-α]pyridin-3-yl]-2-butyn-1-ol (1.3 g, 72%) as a white solid. R$_f$ 0.44 (2:1 hexanes:ethyl acetate); $^1$H NMR (CDCl$_3$) δ 7.99 (d, 1H), 7.78 (m, 2H), 7.14 (m, 3H), 6.95 (d, 1H), 5.70 (m, 1H), 2.21 (d, 1H), 1.85 (d, 3H); MS m/z 315 (M+1).

c) 1-[7-Chloro-2-(4-fluorophenyl)pyrazolo[1,5-α]pyridin-3-yl]-2-butyn-1-one

To a solution of 1-[7-chloro-2-(4-fluorophenyl)pyrazolo[1,5-α]pyridin-3-yl]-2-butyn-1-ol (1.04 g, 3.30 mmol) in chloroform (50 mL) was added manganese dioxide (5.70 g, 65.6 mmol). The reaction mixture was stirred at room temperature for 3 hours. The suspension was filtered through a pad of Celite and the filtrate was concentrated in vacuo to give 1-[7-chloro-2-(4-fluorophenyl)pyrazolo[1,5-α]pyridin-3-yl]-2-butyn-1-one (950 mg, 91%). R$_f$ 0.44 (3:1 hexanes: ethyl acetate); $^1$H NMR (CDCl$_3$) δ 8.49 (d, 1H), 7.73 (m, 2H), 7.50 (t, 1H), 7.19 (m, 3H), 1.71 (3H); $^{19}$F NMR (CDCl$_3$) δ −112.58; mp 182–183° C.

d) 4-[7-Chloro-2-(4-fluorophenyl)pyrazolo[1,5-α]pyridin-3-yl]-N-cyclopentyl-6-methyl-2-pyrimidinamine To a dry round bottom flask was added sodium metal (81 mg, 3.5 mmol). Ethanol (20 mL) was added and allowed to react with sodium at room temperature until completely dissolved. N-Cyclopentylguanidine hydrochloride (572 mg, 3.5 mmol) was added and the mixture was allowed to stir at room temperature for 10 minutes. To the resultant mixture was added 1-[7-chloro-2-(4-fluorophenyl)pyrazolo[1,5-α]pyridin-3-yl]-2-butyn-1-one (842 mg, 2.69 mmol) and the reaction mixture was allowed to stir at room temperature for 72 hours, then heated to 70° C. for 12 hours. The reaction mixture was cooled to room temperature and diluted with water. The mixture was extracted with ethyl acetate, and the combined extracts were washed with water and brine. The organic layer was dried over magnesium sulfate. Filtration and concentration followed by flash chromatography (4:1 hexanes:ether to 3:2 hexanes:ether) provided 4-[7-chloro-2-(4-fluorophenyl)pyrazolo[1,5-α]pyridin-3-yl]-N-cyclopentyl-6-methyl-2-pyrimidinamine (1.11 g, 98%) as a yellow foam. $R_f$ 0.45 (3:1 hexanes:ethyl acetate). $^1$H NMR (CDCl$_3$) δ 8.35 (d, 1H), 7.64 (m, 2H), 7.24 (m, 1H), 7.13 (m, 2H), 7.03 (d, 1H), 6.22 (s, 1H), 5.10 (m, 1H), 4.35 (m, 1H), 2.19 (s, 3H), 2.03 (m, 2H), 1.60 (m, 6H); MS m/z 422 (M+1).

EXAMPLE 8

N-Cyclopentyl-3-[2-(cyclopentylamino)-6-methyl-4-pyrimidinyl]-2-(4-fluorophenyl)pyrazolo[1,5-α]pyridin-7-amine

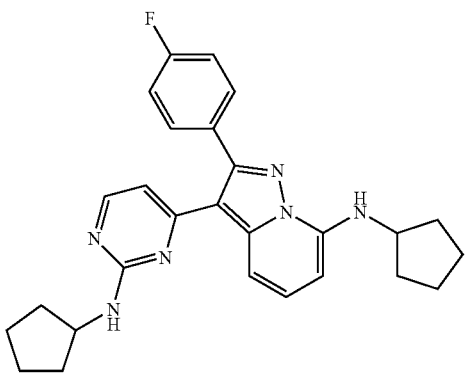

In a similar manner as described in Example 1, from 4-[7-chloro-2-(4-fluorophenyl)pyrazolo[1,5-α]pyridin-3-yl]-N-cyclopentyl-6-methyl-2-pyrimidinamine (58 mg, 0.14 mmol) and cyclopentylamine was formed N-cyclopentyl-3-[2-(cyclopentylamino)-6-methyl-4-pyrimidinyl]-2-(4-fluorophenyl)pyrazolo[1,5-α]pyridin-7-amine (41 mg, 64%) as a clear oil. $^1$H NMR (CDCl$_3$): δ 7.69–7.62 (m, 3H), 7.28 (t, 1H), 7.12 (t, 2H), 6.21 (s, 1H), 6.02–5.99 (m, 2H), 5.05 (d, 1H), 4.33 (m, 1H), 3.99 (m, 1H), 2.15 (s, 3H), 2.15–1.45 (m, 16H); $^{19}$F NMR (CDCl$_3$) δ −113.70; MS m/z 471 (M+1). This material was treated with anhydrous hydrochloric acid in ether to provide a hydrochloride salt as a yellow solid.

EXAMPLE 9

2-(4-Bromophenyl)-N-butyl-3-[2-(1-pyrrolidinyl)-4-pyrimidinyl]pyrazolo[1,5-α]pyridin-7-amine

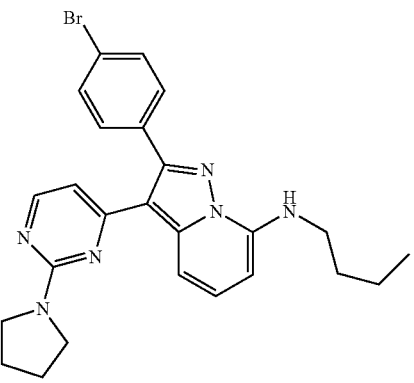

In a similar manner as described in Example 1, from (2E)-1-[2-(4-bromophenyl)-7-(butylamino)pyrazolo[1,5-α]pyridin-3-yl]-3-(dimethylamino)-2-propen-1-one (47 mg, 0.11 mmol) and 1-pyrrolidinecarboximidamide sulfate was obtained 2-(4-bromophenyl)-N-butyl-3-[2-(1-pyrrolidinyl)-4-pyrimidinyl]pyrazolo[1,5-α]pyridin-7-amine (34 mg, 66%) as a yellow solid. $^1$H NMR (CDCl$_3$): δ 8.05 (d, 1H), 7.74 (d, 1H), 7.52 (ABq, 4H), 7.27 (t, 1H), 6.22 (d, 1H), 5.99–5.95 (m, 2H), 3.61 (m, 4H), 3.33 (m, 2H), 1.98 (m, 4H), 1.71 (m, 2H), 1.44 (m, 2H), 0.94 (t, 3H); MS m/z 491 (M+1).

EXAMPLE 10

2-(4-Bromophenyl)-N-butyl-3-[2-(cyclopentylamino)-4-pyrimidinyl]pyrazolo[1,5-α]pyridin-7-amine

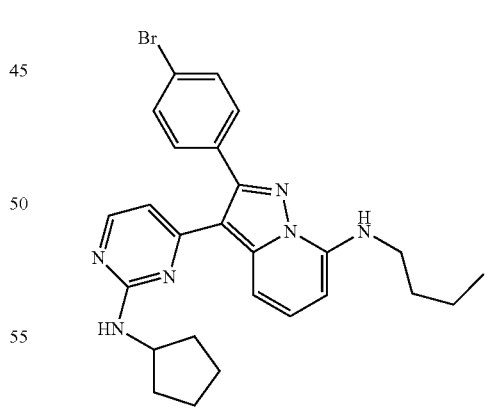

In a similar manner as described in Example 1, from (2E)-1-[2-(4-bromophenyl)-7-(butylamino)pyrazolo[1,5-α]pyridin-3-yl]-3-(dimethylamino)-2-propen-1-one (299 mg, 0.68 mmol) was obtained 2-(4-bromophenyl)-N-butyl-3-[2-(cyclopentylamino)-4-pyrimidinyl]pyrazolo[1,5-α]pyridin-7-amine (251 mg, 74%) as a yellow crystalline solid. $^1$H NMR (CDCl$_3$): δ 8.07 (d, 1H), 7.74 (d, 1H), 7.60 (ABq, 4H), 7.35 (t, 1H), 6.34 (d, 1H), 6.07–6.04 (m, 2H), 5.09 (d, 1H), 4.34 (m, 1H), 3.41 (m, 2H), 2.10 (m, 2H), 1.85–1.47 (m, 10H), 1.02 (t, 3H); MS m/z 505 (M+1).

EXAMPLE 11

N-Cyclopentyl-3-[2-(dimethylamino)-4-pyrimidinyl]-2-(4-fluorophenyl)pyrazolo[1,5-α]pyridin-7-amine

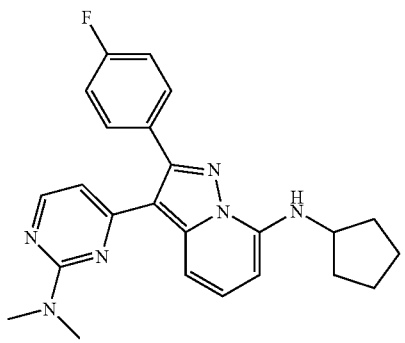

In a similar manner as described in Example 1, from (2E)-1-[7-(cyclopentylamino)-2-(4-fluorophenyl)pyrazolo [1,5-α]pyridin-3-yl]-3-(dimethylamino)-2-propen-1-one (250 mg, 0.64 mmol) and N,N-dimethylguanidine sulfate was obtained N-cyclopentyl-3-[2-(dimethylamino)-4-pyrimidinyl]-2-(4-fluorophenyl)pyrazolo[1,5-α]pyridin-7-amine (233 mg, 87%) as a white solid. $^1$H NMR (CDCl$_3$): δ 8.13 (d, 1H), 7.75 (d, 1H), 7.67 (dd, 2H), 7.33 (t, 1H), 7.16 (t, 2H), 6.30 (d, 1H), 6.06–6.04 (m, 2H), 4.02 (m, 1H), 3.26 (s, 6H), 2.16 (m, 2H), 1.84–1.65 (m, 6H); MS m/z 417 (M+1).

EXAMPLE 12

3-(2-Amino-4-pyrimidinyl)-N-cyclopentyl-2-(4-fluorophenyl)pyrazolo[1,5-α]pyridin-7-amine

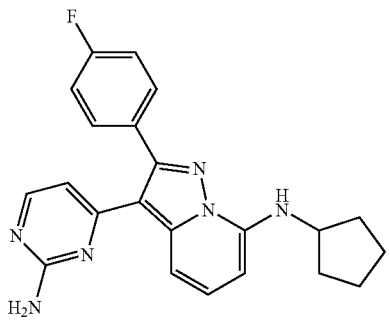

In a similar manner as described in Example 1, from (2E)-1-[7-(cyclopentylamino)-2-(4-fluorophenyl)pyrazolo [1,5-α]pyridin-3-yl]-3-(dimethylamino)-2-propen-1-one (375 mg, 0.96 mmol) and guanidine hydrochloride was obtained 3-(2-amino-4-pyrimidinyl)-N-cyclopentyl-2-(4-fluorophenyl)pyrazolo[1,5-α]pyridin-7-amine (220 mg, 60%) as a white solid. $^1$H NMR (CDCl$_3$): δ 7.98 (d, 1H), 7.66 (d, 1H), 7.59 (m, 2H), 7.28 (t, 1H), 7.10 (t, 2H), 6.31 (d, 1H), 6.00 (d, 1H), 5.96 (d, 1H), 4.97 (broad s, 2H), 3.96 (m, 1H), 2.14–2.06 (m, 2H), 1.83–1.63 (m, 6H); $^{13}$C NMR (CDCl$_3$) δ 163.39 (d, J$_{CF}$=246.6 Hz), 163.20, 162.25, 157.27, 152.33, 142.88, 141.32, 131.64 (d, J$_{CF}$=8.4 Hz), 129.91 (d, J$_{CF}$=3.8 Hz), 128.84, 115.75 (d, J$_{CF}$=22.0 Hz), 110.31, 106.85, 105.31, 90.53, 54.06, 33.53, 24.27; $^{19}$F NMR (CDCl$_3$) δ –113.20; MS m/z 389 (M+1); Anal. Calcd for C$_{22}$H$_{21}$FN$_6$: C, 68.03; H, 5.45; N, 21.63. Found: C, 67.96; H, 5.50; N, 21.82.

EXAMPLE 13

N-Cyclopentyl-2-(4-fluorophenyl)-3-(2-{[3-(4-morpholinyl)propyl]-amino}-4-pyrimidinyl)pyrazolo[1, 5-α]pyridin-7-amine

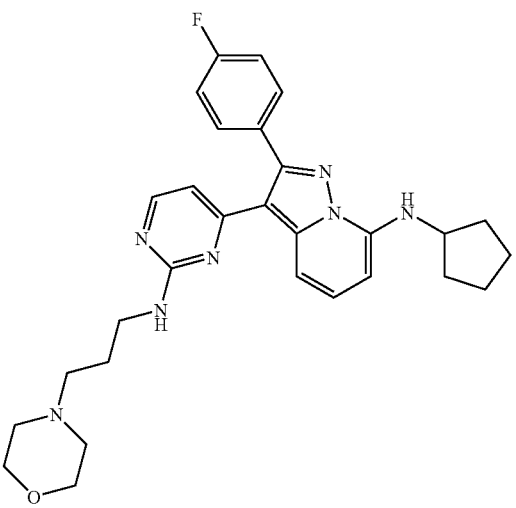

In a similar manner as described in Example 1, from (2E)-1-[7-(cyclopentylamino)-2-(4-fluorophenyl)pyrazolo [1,5-α]pyridin-3-yl]-3-(dimethylamino)-2-propen-1-one (250 mg, 0.64 mmol) and N-[3-(4-morpholinyl)propyl] guanidine sulfate was obtained N-cyclopentyl-2-(4-fluorophenyl)-3-(2-{[3-(4-morpholinyl)propyl]amino}-4-pyrimidinyl)pyrazolo[1,5-α]pyridin-7-amine (200 mg, 61%) as a tan solid. $^1$H NMR (CDCl$_3$): δ 7.97 (d, 1H), 7.69 (d, 1H), 7.59 (dd, 2H), 7.26 (t, 1H), 7.10 (t, 2H), 6.24 (d, 1H), 6.00 (d, 1H), 5.96 (d, 1H), 5.70 (broad, 1H), 3.97 (m, 1H), 3.71 (m, 4H), 3.49 (m, 2H), 2.48–2.45 (m, 6H), 2.10 (m, 2H), 1.83–1.59 (m, 8H); $^{19}$F NMR (CDCl$_3$) δ –113.46; MS m/z 516 (M+1).

EXAMPLE 14

N-Cyclopentyl-4-[2-(4-fluorophenyl)-7-hydrazinopyrazolo[1,5-α]pyridin-3-yl]-6-methyl-2-pyrimidinamine

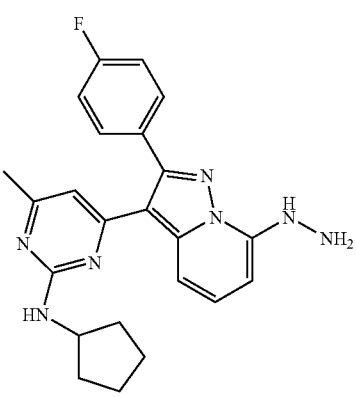

To a solution of 4-[7-chloro-2-(4-fluorophenyl)pyrazolo[1,5-α]pyridin-3-yl]-N-cyclopentyl-6-methyl-2-pyrimidinamine (100 mg, 0.237 mmol) in ethanol (1 mL) was added hydrazine (500 uL, 15.9 mmol). The reaction mixture was heated in a sealed tube at 90° C. for 72 hours. The mixture was cooled and diluted with ethyl acetate and washed with saturated aqueous sodium bicarbonate, water and brine. The combined organics were dried over magnesium sulfate. Filtration and concentration followed by flash chromatography (38:2 dichloromethane-methanol) provided N-cyclopentyl-4-[2-(4-fluorophenyl)-7-hydrazinopyrazolo[1,5-α]pyridin-3-yl]-6-methyl-2-pyrimidinamine (45 mg, 46%) as a yellow solid. $R_f$ 0.43 (38:2 $CH_2Cl_2$-MeOH); $^1$H NMR ($CDCl_3$) δ 7.78 (1H), 7.62 (2H), 7.35 (1H), 7.20 (1H), 7.12 (2H), 6.45 (1H), 6.24 (1H), 5.03 (1H), 4.35 (1H), 3.85 (2H), 2.18 (3H), 2.02 (2H), 1.62 (6H); MS m/z 418 (M+1).

EXAMPLE 15

N-Cyclopentyl-4-[2-(4-fluorophenyl)-7-(4-methyl-1-piperazinyl)pyrazolo[1,5-α]pyridin-3-yl]-6-methyl-2-pyrimidinamine

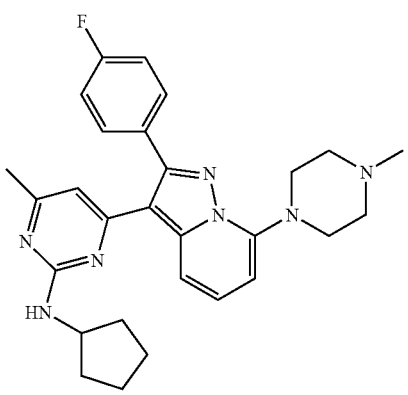

In a similar manner to Example 14, from 4-[7-chloro-2-(4-fluorophenyl)pyrazolo[1,5-α]pyridin-3-yl]-N-cyclopentyl-6-methyl-2-pyrimidinamine (100 mg, 0.237 mmol) and N-methylpiperazine (1 mL, 9.01 mmol) was formed N-cyclopentyl-4-[2-(4-fluorophenyl)-7-(4-methyl-1-piperazinyl)pyrazolo[1,5-α]pyridin-3-yl]-6-methyl-2-pyrimidinamine (80 mg, 70%) as a clear oil. $R_f$ 0.31 (3:2 hexanes:ethyl acetate) $^1$H NMR ($CDCl_3$) δ 8.00 (d, 1H), 7.66 (m, 2H), 7.25 (d, 1H), 7.08 (t, 2H), 6.31 (d, 1H), 6.27 (s, 1H), 5.02 (d, 1H), 4.34 (m, 1H), 3.50 (m, 4H), 2.72 (m, 4H), 2.41 (s, 3H), 2.18 (s, 3H), 2.03 (m, 2H), 1.65 (m, 6H); MS m/z 486 (M+1). This material was taken up in ether and treated with hydrochloric acid in ether to yield an orange precipitate which was isolated by filtration as a hydrochloride salt.

EXAMPLE 16

N-Cyclopentyl-3-{2-(cyclopentylamino)-6-[(tetrahydro-2H-pyran-2-yloxy)methyl]-4-pyrimidinyl}-2-(4-fluorophenyl)pyrazolo[1,5-α]pyridin-7-amine

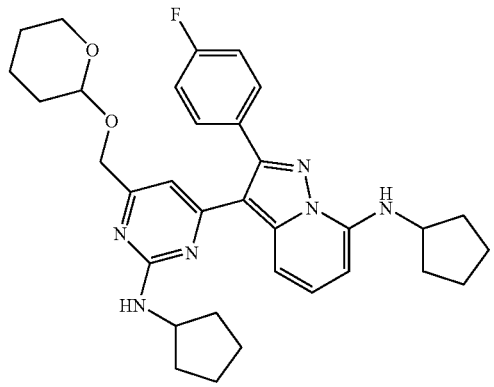

a) 1-[7-Chloro-2-(4-fluorophenyl)pyrazolo[1,5-α]pyridin-3-yl]-4-(tetrahydro-2H-pyran-2-yloxy)-2-butyn-1-ol To a cold (−78° C.) solution of tetrahydro-2-(2-propynyloxy)-2H-pyran (0.5 mL, 3.6 mmol) in tetrahydrofuran (10 mL) was added n-butyllithium (2.05 mL, 1.6 M in hexanes, 3.3 mmol) dropwise. The reaction mixture was allowed to warm to 0° C., then cooled to −78° C. A separate solution of 7-chloro-2-(4-fluorophenyl)pyrazolo[1,5-α]pyridine-3-carbaldehyde (200 mg, 0.73 mmol) in tetrahydrofuran (5 mL) was cooled to 0° C. The alkynyllithium solution was added to the aldehyde solution via canula. The reaction mixture was allowed to warm to room temperature and stirred for 1 hour. Water was added followed by ether. The organic layer was washed with water and brine. The aqueous layer was extracted with ether and the combined organics were dried over magnesium sulfate. Filtration and concentration followed by flash chromatography (2:1 hexanes:ethyl acetate) provided 1-[7-chloro-2-(4-fluorophenyl)pyrazolo[1,5-α]pyridin-3-yl]-4-(tetrahydro-2H-pyran-2-yloxy)-2-butyn-1-ol (301 mg, 99%) as a mixture of diastereomers. $^1$H NMR ($CDCl_3$) δ 8.00 (d, 1H), 7.79 (m, 2H), 7.17 (m 3H), 6.99 (m, 1H), 5.79 (s, 1H), 4.81–4.74 (m, 1H), 4.39–4.25 (m, 2H), 3.81 (m, 1H), 3.52 (m, 1H), 3.15 (broad, 1H), 1.90–1.48 (m, 6H); $^{19}$F NMR ($CDCl_3$) δ −113.01; MS m/z 437 (M+Na$^+$).

b) 1-[7-Chloro-2-(4-fluorophenyl)pyrazolo[1,5-α]pyridin-3-yl]-4-(tetrahydro-2H-pyran-2-yloxy)-2-butyn-1-one In a similar manner as described in Example 7, from 1-[7-chloro-2-(4-fluorophenyl)pyrazolo[1,5-α]pyridin-3-yl]-4-(tetrahydro-2H-pyran-2-yloxy)-2-butyn-1-ol (301 mg, 0.73 mmol) was formed 1-[7-chloro-2-(4-fluorophenyl)pyrazolo[1,5-α]pyridin-3-yl]-4-(tetrahydro-2H-pyran-2-yloxy)-2-butyn-1-one (280 mg, 93%) as a white solid. $^1$H NMR ($CDCl_3$) δ 8.48 (d, 1H), 7.71 (m, 2H), 7.50 (m, 1H), 7.17 (m, 3H), 4.59 (m, 1H), 4.11 (s, 2H), 3.72 (m, 1H), 3.49 (m, 1H), 1.82–1.50 (m, 6H); $^{19}$F NMR ($CDCl_3$) δ −111.89; MS m/z 435 (M+Na$^+$).

c) 4-[7-Chloro-2-(4-fluorophenyl)pyrazolo[1,5-α]pyridin-3-yl]-N-cyclopentyl-6-[(tetrahydro-2H-pyran-2-yloxy)methyl]-2-pyrimidinamine In a similar manner as described in Example 7, from 1-[7-chloro-2-(4-fluorophenyl)pyrazolo[1,5-α]pyridin-3-yl]-4-(tetrahydro-2H-pyran-2-yloxy)-2-butyn-1-one (186 mg, 0.45 mmol) was formed 4-[7-chloro-2-(4-fluorophenyl)pyrazolo[1,5-α]pyridin-3-yl]-N-cyclopentyl-6-[(tetrahydro-2H-pyran-2-yloxy)methyl]-2-pyrimidinamine (165 mg, 71%) as a clear oil. $R_f$ 0.12 (4:1 hexanes:ethyl acetate); $^1$H NMR (CDCl$_3$) δ 8.46 (d, 1H), 7.65 (m, 2H), 7.24 (m, 1H), 7.11 (t, 2H), 7.02 (d, 1H), 6.51 (s, 1H), 5.09 (d, 1H), 4.58 (m, 1H), 4.50 (d, 1H), 4.37 (m, 1H), 4.08 (d, 1H), 3.66 (m, 1H), 3.45 (m, 1H), 2.06 (m, 2H), 1.58 (m, 12H); $^{19}$F NMR (CDCl$_3$) δ −113.16; MS m/z 522 (M+1).

d) N-Cyclopentyl-3-{2-(cyclopentylamino)-6-[(tetrahydro-2H-pyran-2-yloxy)-methyl]-4-pyrimidinyl}-2-(4-fluorophenyl)pyrazolo[1,5-α]pyridin-7-amine In a similar manner as described in Example 8, from 4-[7-chloro-2-(4-fluorophenyl)pyrazolo[1,5-α]pyridin-3-yl]-N-cyclopentyl-6-[(tetrahydro-2H-pyran-2-yloxy)methyl]-2-pyrimidinamine (163 mg, 0.31 mmol) was formed N-cyclopentyl-3-{2-(cyclopentylamino)-6-[(tetrahydro-2H-pyran-2-yloxy)methyl]-4-pyrimidinyl}-2-(4-fluorophenyl)pyrazolo[1,5-α]pyridin-7-amine (146 mg, 82%) as a white solid. $^1$H NMR (CDCl$_3$) δ 7.80 (d, 1H), 7.68 (m, 2H), 7.37–7.13 (m, 3H), 6.53 (5, 1H), 6.06 (m, 2H), 5.04 (d, 1H), 4.63 (broad, 1H), 4.53 (d, 1H), 4.40 (m, 1H), 4.31 (d, 1H), 4.05 (m, 1H), 3.74 (m, 1H), 3.50 (m, 1H), 2.24–1.44 (m, 22H); $^{19}$F NMR (CDCl$_3$) δ −113.75; MS m/z 571 (M+1).

EXAMPLE 17

[6-[7-Chloro-2-(4-fluorophenyl)pyrazolo[1,5-α]pyridin-3-yl]-2-(cyclopentylamino)-4-pyrimidinyl]methanol

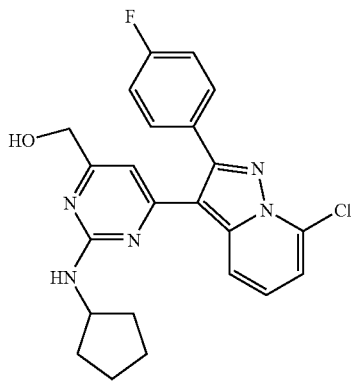

To a solution of 4-[7-chloro-2-(4-fluorophenyl)pyrazolo[1,5-α]pyridin-3-yl]-N-cyclopentyl-6-[(tetrahydro-2H-pyran-2-yloxy)methyl]-2-pyrimidinamine (1.18 g, 2.26 mmol) in tetrahydrofuran (20 mL) at 0° C. was added hydrochloric acid (8 mL, 4 N aqueous, 32 mmol). The reaction mixture was allowed to warm to room temperature and was stirred for 48 hours. The solution was diluted and extracted with ethyl acetate. The organic layer was washed with water and brine and dried over magnesium sulfate. Filtration and concentration followed by flash chromatography (2:1 hexanes:ethyl acetate) provided [6-[7-chloro-2-(4-fluorophenyl)pyrazolo[1,5-α]pyridin-3-yl]-2-(cyclopentylamino)-4-pyrimidinyl]methanol (815 mg, 82%) as a solid. $R_f$ 0.21 (2:1 hexanes:ethyl acetate); $^1$H NMR (CDCl$_3$) δ 8.31 (d, 1H), 7.60 (m, 2H), 7.22 (m, 1H), 7.10 (m, 2H), 7.01 (d, 1H), 6.23 (s, 1H), 5.37 (d, 1H), 4.33 (m, 3H), 3.95 (br, 1H), 2.03 (m, 2H), 1.62 (m, 6H); $^{19}$F NMR (CDCl$_3$) δ −112.70; MS m/z 438 (M+1).

EXAMPLE 18

[{4-[7-(Cyclopentylamino)-2-(4-fluorophenyl)pyrazolo[1,5-α]pyridin-3-yl]-2-pyrimidinyl}(methyl)amino]acetic acid

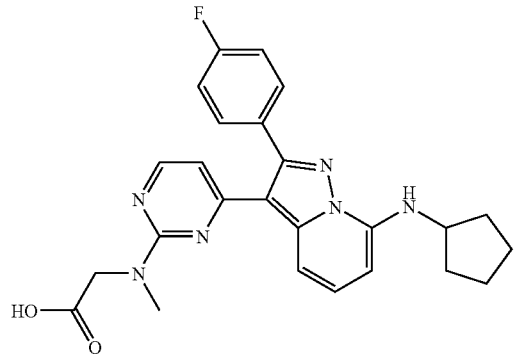

In a similar manner as described in Example 1, from (2E)-1-[7-(cyclopentylamino)-2-(4-fluorophenyl)pyrazolo[1,5-α]pyridin-3-yl]-3-(dimethylamino)-2-propen-1-one (200 mg, 0.51 mmol) and creatine was obtained [{4-[7-(cyclopentylamino)-2-(4-fluorophenyl)pyrazolo[1,5-α]pyridin-3-yl]-2-pyrimidinyl}(methyl)amino]acetic acid (30 mg, 13%) as a yellow solid. $^1$H NMR (DMSO-d$^6$; all peaks broad) δ 8.03 (1H), 7.61 (3H), 7.29 (3H), 6.58 (1H), 6.17 (2H), 4.17 (2H), 4.00 (1H), 3.12 (s, 3H), 2.03 (2H), 1.66 (6H); $^{19}$F NMR (DMSO-d$_6$) δ −113.51; MS m/z 461 (M+1).

EXAMPLE 19

N-Cyclopentyl-4-[2-(4-fluorophenyl)-7-(4-methyl-1-piperazinyl)pyrazolo[1,5-α]pyridin-3-yl]-6-phenyl-2-pyrimidinamine hydrochloride

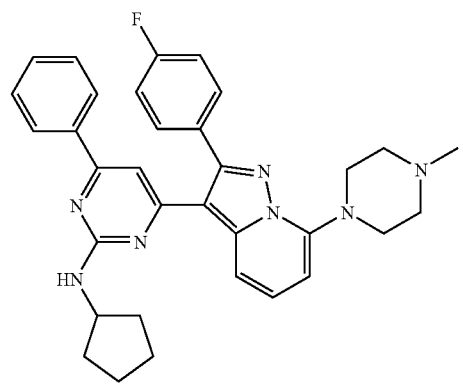

a) 1-[7-Chloro-2-(4-fluorophenyl)pyrazolo[1,5-α]pyridin-3-yl]-3-phenyl-2-propyn-1-ol In a similar manner to Example 16 from 7-chloro-2-(4-fluorophenyl)pyrazolo[1,5-α]pyridine-3-carbaldehyde (190 mg, 0.69 mmol) and phenylacetylene was formed 1-[7-chloro-2-(4-fluorophenyl)pyrazolo[1,5-α]pyridin-3-yl]-3-phenyl-2-propyn-1-ol (250 mg, 96%) as a white solid. $^1$H NMR (CDCl$_3$) δ 8.10 (d, 1H), 7.87 (dd, 2H), 7.44–7.41 (m, 2H), 7.37–7.33 (m, 3H), 7.25–7.19 (m, 3H), 7.02 (d, 1H), 6.02 (d, 1H), 2.66 (d, 1H); $^{19}$F NMR (CDCl$_3$) δ –113.02; MS m/z 399 (M+Na$^+$).

b) 1-[7-Chloro-2-(4-fluorophenyl)pyrazolo[1,5-α]pyridin-3-yl]-3-phenyl-2-propyn-1-one In a similar manner to Example 7, from 1-[7-chloro-2-(4-fluorophenyl)pyrazolo[1,5-α]pyridin-3-yl]-3-phenyl-2-propyn-1-ol (250 mg, 0.66 mmol) was formed 1-[7-chloro-2-(4-fluorophenyl)pyrazolo[1,5-α]pyridin-3-yl]-3-phenyl-2-propyn-1-one (246 mg, 99%) as a white solid. $^1$H NMR (CDCl$_3$) δ 8.47 (d, 1H), 7.76 (dd, 2H), 7.47 (dd, 1H), 7.34 (t, 1H), 7.24 (m, 2H), 7.16 (d, 1H), 7.13–7.05 (m, 4H).

c) 4-[7-Chloro-2-(4-fluorophenyl)pyrazolo[1,5-α]pyridin-3-yl]-N-cyclopentyl-6-phenyl-2-pyrimidinamine To a solution of 1-[7-chloro-2-(4-fluorophenyl)pyrazolo[1,5-α]pyridin-3-yl]-3-phenyl-2-propyn-1-one (246 mg, 0.66 mmol) in N,N-dimethylformamide (10 mL) was added N-cyclopentylguanidine hydrochloride (320 mg, 1.97 mmol) followed by solid potassium carbonate (274 mg, 1.97 mmol). The resultant mixture was heated to 75° C. for 4 hours The reaction mixture was cooled to room temperature, diluted with water and ether was added. The organic layer was washed with brine. The aqueous layer was extracted with ether and the combined organics were dried over magnesium sulfate. Filtration and concentration followed by flash chromatography (4:1, hexanes:ethyl acetate) provided 4-[7-chloro-2-(4-fluorophenyl)pyrazolo[1,5-α]pyridin-3-yl]-N-cyclopentyl-6-phenyl-2-pyrimidinamine (265 mg, 84%) as a solid. $^1$H NMR (CDCl$_3$) δ 8.49 (d, 1H), 7.80–7.75 (m, 4H), 7.44–7.41 (m, 3H), 7.33 (m, 1H), 7.22 (t, 2H), 7.09 (d, 1H), 6.82 (s, 1H), 5.25 (d, 1H), 4.49 (m, 1H), 2.22–2.12 (m, 2H), 1.88–1.61 (m, 6H); $^{19}$F NMR (CDCl$_3$) δ –112.89; MS m/z 484 (M+1).

d) N-Cyclopentyl-4-[2-(4-fluorophenyl)-7-(4-methyl-1-piperazinyl)pyrazolo[1,5-α]pyridin-3-yl]-6-phenyl-2-pyrimidinamine hydrochloride In a similar manner as described in Example 1, from 4-[7-chloro-2-(4-fluorophenyl)pyrazolo[1,5-α]pyridin-3-yl]-N-cyclopentyl-6-phenyl-2-pyrimidinamine (60 mg, 0.12 mmol) and N-methylpiperazine was formed N-cyclopentyl-4-[2-(4-fluorophenyl)-7-(4-methyl-1-piperazinyl)pyrazolo[1,5-α]pyridin-3-yl]-6-phenyl-2-pyrimidinamine (70 mg, 99%) as an oil. This material was taken up in ether and treated with hydrochloric acid in ether to yield a yellow precipitate which was isolated by filtration as an hydrochloride salt. $^1$H NMR (DMSO-d$_6$) δ 11.18 (broad, 1H), 8.22 (d, 1H), 7.78–7.73 (m, 4H), 7.63–7.36 (m, 6H), 6.77 (s, 1H), 4.29 (broad, 1H), 4.19–4.16 (m, 2H), 3.55 (m, 2H), 3.39–3.29 (m, 4H), 2.83 (d, 3H), 1.95 (m, 2H), 1.73–1.59 (m, 6H); $^{19}$F NMR (DMSO-d$_6$) δ –112.68; MS m/z 548 (M+1).

EXAMPLE 20

N'-[3-[2-(Cyclopentylamino)-6-phenyl-4-pyrimidinyl]-2-(4-fluorophenyl)pyrazolo[1,5-α]pyridin-7-yl]-1,2-ethanediamine

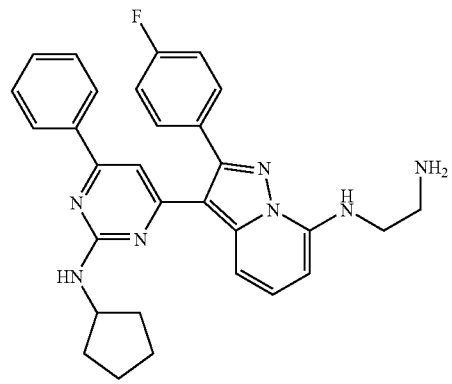

In a similar manner as described in Example 1, from 4-[7-chloro-2-(4-fluorophenyl)pyrazolo[1,5-α]pyridin-3-yl]-N-cyclopentyl-6-phenyl-2-pyrimidinamine (60 mg, 0.12 mmol) and ethylenediamine was formed N$^1$-[3-[2-(cyclopentylamino)-6-phenyl-4-pyrimidinyl]-2-(4-fluorophenyl)pyrazolo[1,5-α]pyridin-7-yl]-1,2-ethanediamine (30 mg, 48%) as an oil. $^1$H NMR (CDCl$_3$) δ 7.84–7.72 (m, 6H), 7.42–7.40 (m, 3H), 7.33 (t, 1H), 7.18 (t, 1H), 6.80 (s, 1H), 6.44 (m, 1H), 6.05 (d, 1H), 5.26 (d, 1H), 4.47 (m, 1H), 3.48 (m, 2H), 3.09 (broad, 2H), 2.93 (broad, 2H), 2.13 (m, 2H), 1.83–1.56 (m, 6H); $^{19}$F NMR (CDCl$_3$) δ –113.21; MS m/z 508 (M+1). This material was taken up in ether and treated with hydrochloric acid in ether to yield an orange precipitate which was isolated by filtration as a hydrochloride salt.

EXAMPLE 21

3-[2-(Cyclopentylamino)-4-pyrimidinyl]-2-(4-fluorophenyl)pyrazolo[1,5-α]pyridin-7-amine

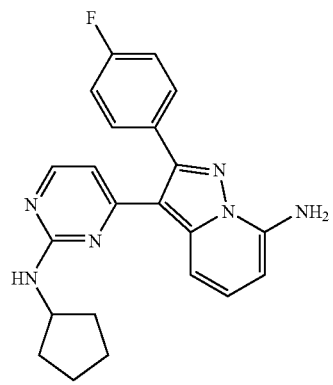

To a solution of 4-[7-chloro-2-(4-fluorophenyl)pyrazolo[1,5-α]pyridin-3-yl]-N-cyclopentyl-2-pyrimidinamine (53 mg, 0.13 mmol) in N,N-dimethylformamide (4 mL) was added sodium azide (85 mg, 1.3 mmol). The resultant mixture was heated to 100° C. for 18 hours. The reaction mixture was cooled to room temperature and ether was added. The organic layer was washed with brine. The aqueous layer was extracted with ether and the combined organics dried over magnesium sulfate. Filtration and concentration followed by flash chromatography (2:1 to 1:1 hexanes:ethyl acetate) provided 3-[2-(cyclopentylamino)-4-pyrimidinyl]-2-(4-fluorophenyl)pyrazolo[1,5-α]pyridin-7-amine (30 mg, 60%) as an oil. $^1$H NMR (CDCl$_3$) δ 7.97 (d, 1H), 7.77 (d, 1H), 7.60 (m, 2H), 7.22 (m, 1H), 7.10 (t, 2H), 6.26 (d, 1H), 6.14 (d, 1H), 5.26 (s, 2H), 5.09 (d, 1H), 4.29 (m, 1H), 2.06–1.99 (m, 2H), 1.75–1.45 (m, 6H); MS m/z 389 (M+1). This material was taken up in ether and treated with hydrochloric acid in ether to yield a yellow precipitate which was isolated by filtration as a hydrochloride salt.

EXAMPLE 22

{2-(Cyclopentylamino)-6-[7-(cyclopentylamino)-2-(4-fluorophenyl)pyrazolo[1,5-α]pyridin-3-yl]-4-pyrimidinyl}methanol

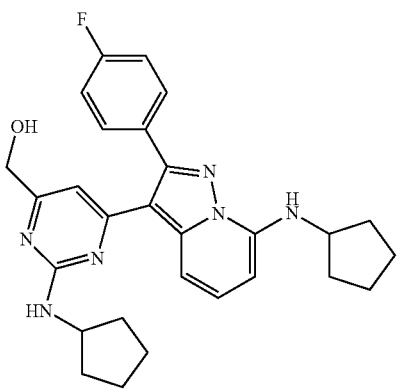

To a solution of N-cyclopentyl-3-{2-(cyclopentylamino)-6-[(tetrahydro-2H-pyran-2-yloxy)methyl]-4-pyrimidinyl}-2-(4-fluorophenyl)pyrazolo[1,5-α]pyridin-7-amine (134 mg, 2.23 mmol) in tetrahydrofuran (8 mL) was added hydrochloric acid (4 mL, 4 N aqueous, 32 mmol). After 30 minutes, the solution was made basic with sodium bicarbonate and ether was added. The organic layer was washed with water and brine and dried over magnesium sulfate. Filtration and concentration followed by flash chromatography (2:1 to 1:1 hexanes:ethyl acetate) provided {2-(cyclopentylamino)-6-[7-(cyclopentylamino)-2-(4-fluorophenyl) pyrazolo[1,5-α]pyridin-3-yl]-4-pyrimidinyl}methanol (80 mg, 71%). This material was taken up in ether and treated with anhydrous hydrochloric acid in ether to yield upon filtration a yellow solid. $^1$H NMR of hydrochloride salt (CDCl$_3$) δ 8.00–7.94 (broad, 1H), 7.78 (d, 1H), 7.54–7.44 (m, 3H), 7.17 (m, 2H), 6.22 (s, 1H), 6.19 (d, 1H), 6.07 (d, 1H), 4.74–4.60 (broad, 1H), 4.47 (s, 2H), 4.36 (m, 1H), 3.99 (m, 1H), 2.16–2.00 (m, 4H), 1.82–1.59 (m, 12H); $^{19}$F NMR (CDCl$_3$) δ –111.26; MS m/z 487 (M+1 of free base).

EXAMPLE 23

3-[2-(Cyclopentylamino)-4-pyrimidinyl]-2-(4-fluorophenyl)-N-(4-methoxyphenyl)pyrazo[1,5-α]pyridin-7-amine

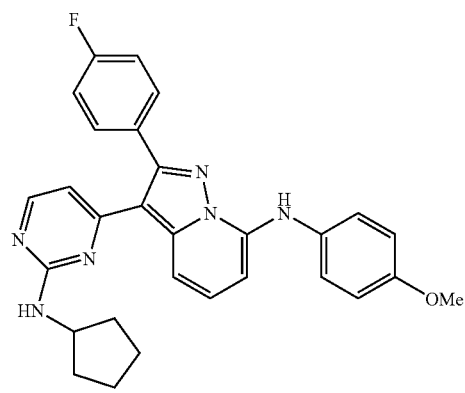

In a similar manner as described in Example 1, from 4-[7-chloro-2-(4-fluorophenyl)pyrazolo[1,5-α]pyridin-3-yl]-N-cyclopentyl-2-pyrimidinamine (48 mg, 0.12 mmol) and p-anisidine was formed 3-[2-(cyclopentylamino)-4-pyrimidinyl]-2-(4-fluorophenyl)-N-(4-methoxyphenyl)pyrazolo[1,5-α]pyridin-7-amine (35 mg, 60%) as a white solid. $^1$H NMR (CDCl$_3$) δ 7.99 (d, 1H), 7.84 (d, 1H), 7.70–7.64 (m, 3H), 7.32–7.26 (m, 3H), 7.17 (t, 2H), 9.67 (d, 2H), 6.34–6.31 (m, 2H), 5.43 (broad, 1H), 4.35 (m, 1H), 3.85 (s, 3H), 2.11–2.03 (m, 2H), 1.83–1.55 (m, 6H); $^{19}$F NMR (CDCl$_3$) δ –112.97; MS m/z 495 (M+1).

EXAMPLE 24

Methyl {[3-[2-(cyclopentylamino)-6-methyl-4-pyrimidinyl]-2-(4-fluorophenyl)pyrazolo[1,5-α]pyridin-7-yl]amino}acetate

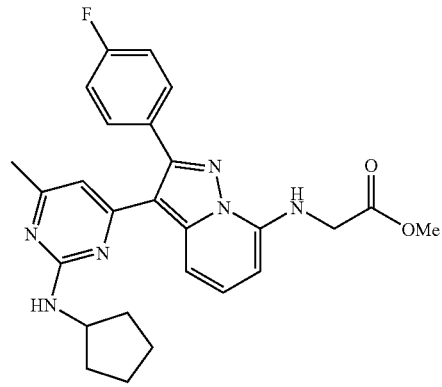

In a similar manner as described in Example 1, from 4-[7-chloro-2-(4-fluorophenyl)pyrazolo[1,5-α]pyridin-3-yl]-N-cyclopentyl-6-methyl-2-pyrimidinamine (94 mg, 0.22 mmol) and methyl glycinate hydrochloride was formed methyl {[3-[2-(cyclopentylamino)-6-methyl-4-pyrimidinyl]-2-(4-fluorophenyl)pyrazolo[1,5-α]pyridin-7-yl]amino}acetate (95 mg, 90%) as a yellow foam. $^1$H NMR (CDCl$_3$) δ 7.74 (d, 1H), 7.67 (dd, 2H), 7.30 (m, 1H), 7.13 (m, 2H), 6.56 (m, 1H), 6.24 (s, 1H), 5.90 (d, 1H), 5.07 (broad, 1H), 4.35 (m, 1H), 4.17 (d, 2H), 3.82 (s, 3H), 2.17 (s, 3H), 2.03 (m, 2H), 1.75–1.50 (m, 6H); $^{19}$F NMR (CDCl$_3$) δ −113.61; MS m/z 475 (M+1).

EXAMPLE 25

{[3-[2-(Cyclopentylamino)-6-methyl-4-pyrimidinyl]-2-(4-fluorophenyl)pyrazolo[1,5-α]pyridin-7-yl]amino}acetic acid

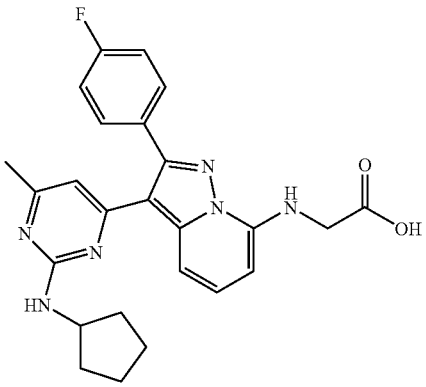

To a room temperature solution of methyl {[3-[2-(cyclopentylamino)-6-methyl-4-pyrimidinyl]-2-(4-fluorophenyl)pyrazolo[1,5-α]pyridin-7-yl]amino}acetate (76 mg, 0.16 mmol) in tetrahydrofuran (3 mL) and methanol (1 mL) was added lithium hydroxide (1 mL, 1.0 M in water, 1 mmol). The resultant mixture was stirred at room temperature for 24 hours then concentrated in vacuo. The residue was suspended in ether and acidified with aqueous hydrochloric acid (4N). The solids were filtered and azeotroped twice with methanol in vacuo to provide the hydrochloride salt of {[3-[2-(cyclopentylamino)-6-methyl-4-pyrimidinyl]-2-(4-fluorophenyl)pyrazolo[1,5-α]pyridin-7-yl]amino}acetic acid (70 mg, 95%) as a yellow solid. $^1$H NMR (CDCl$_3$) δ 7.72–7.34 (m, 7H), 6.40–6.26 (m, 2H), 4.17–4.04 (m, 3H), 2.20 (s, 3H), 1.88 (m, 2H), 1.69 (m, 2H), 1.54 (m, 4H); $^{19}$F NMR (CDCl$_3$) δ −112.96; MS m/z 461 (M+1).

EXAMPLE 26

4-[7-Chloro-2-(4-fluorophenyl)pyrazolo[1,5-α]pyridin-3-yl]-N-cyclopentyl-2-pyrimidinamine

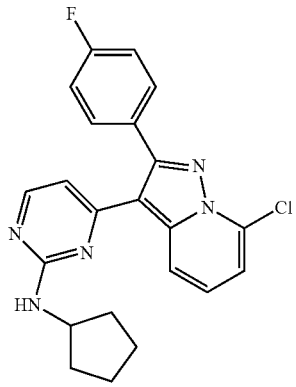

a) 1-[7-Chloro-2-(4-fluorophenyl)pyrazolo[1,5-α]pyridin-3-yl]-2-propyn-1-ol

In a similar manner as described in Example 7 from 7-chloro-2-(4-fluorophenyl)pyrazolo[1,5-α]pyridine-3-carbaldehyde (5.49 g, 20.0 mmol) and ethynylmagnesium bromide (100 mL, 0.5 M in tetrahydrofuran, 50.0 mmol) at 0° C., recrystallized from dichloromethane, was obtained 1-[7-chloro-2-(4-fluorophenyl)pyrazolo[1,5-α]pyridin-3-yl]-2-propyn-1-ol (5.3 g, 88%) as a pale yellow crystalline solid. $^1$H NMR (CDCl$_3$): δ 8.04 (d, 1H), 7.79 (m, 2H), 7.20 (m, 3H), 7.01 (d, 1H), 5.77 (m, 1H), 2.69 (d, 1H), 2.32 (d, 1H); MS m/z 301 (M+1).

b) 1-[7-Chloro-2-(4-fluorophenyl)pyrazolo[1,5-α]pyridin-3-yl]-2-propyn-1-one

In a similar manner as described in Example 7, from 1-[7-chloro-2-(4-fluorophenyl)pyrazolo[1,5-α]pyridin-3-yl]-2-propyn-1-ol (5.30 g, 17.6 mmol) was obtained 1-[7-chloro-2-(4-fluorophenyl)pyrazolo[1,5-α]pyridin-3-yl]-2-propyn-1-one (4.04 g, 77%) as a yellow solid. $^1$H NMR (CDCl$_3$): δ 8.45 (d, 1H), 7.67 (m, 2H), 7.50 (t, 1H), 7.19 (d, 1H), 7.12 (t, 2H), 2.93 (s, 1H); MS m/z 299 (M+1).

c) 4-[7-chloro-2-(4-fluorophenyl)pyrazolo[1,5-α]pyridin-3-yl]-N-cyclopentyl-2-pyrimidinamine In a similar manner as described in Example 7 1-[7-chloro-2-(4-fluorophenyl)pyrazolo[1,5-α]pyridin-3-yl]-2-propyn-1-one (210 mg, 0.70 mmol), cyclopentylguanidine hydrochloride (291 mg, 2.1 mmol), and potassium carbonate (345 mg, 2.1 mmol) were heated at 120° C. for 1.5 hours in 1-methyl-2-pyrrolidinone (8 mL) to form 4-[7-chloro-2-(4-fluorophenyl)pyrazolo[1,5-α]pyridin-3-yl]-N-cyclopentyl-2-pyrimidinamine (125 mg, 44%) as a white foam. $^1$H NMR (CDCl$_3$) δ 8.42 (d, 1H), 8.09 (d, 1H), 7.67 (dd, 2H), 7.30 (m, 1H), 7.17 (t, 2H), 7.06 (d, 1H), 6.33 (d, 1H), 5.30 (d, 1H), 4.35 (m, 1H), 2.18–2.05 (m, 2H), 1.84–1.52 (m, 6H); $^{19}$F NMR (CDCl$_3$) δ −112.78; MS m/z 408 (M+1).

EXAMPLE 27

6-[7-Chloro-2-(4-fluorophenyl)pyrazolo[1,5-α]pyridin-3-yl]-2-(cyclopentylamino)-4-pyrimidinecarboxylic acid

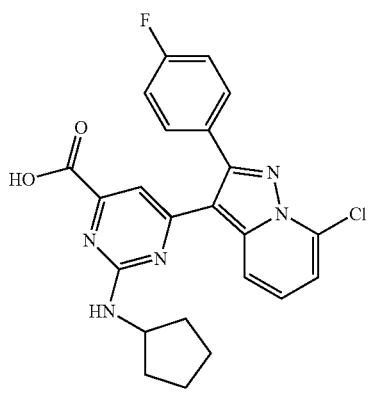

A solution of [6-[7-chloro-2-(4-fluorophenyl)pyrazolo[1,5-α]pyridin-3-yl]-2-(cyclopentylamino)-4-pyrimidinyl]

methanol (50 mg, 0.11 mmol) in dichloromethane (5 mL) was treated with manganese dioxide (397 mg, 4.6 mmol). The resultant heterogeneous mixture was stirred for 5 hours at which time an additional quantity of manganese dioxide (397 mg, 4.6 mmol) was added. After stirring for 3 hours the suspension was filtered through a plug of Celite and eluted sequentially with methanol and then chloroform:isopropanol (3:1). The eluents were removed in vacuo to provide 6-[7-chloro-2-(4-fluorophenyl)pyrazolo[1,5-α]pyridin-3-yl]-2-(cyclopentylamino)-4-pyrimidinecarboxylic acid (54 mg, 99%) as a white solid. $^1$H NMR (DMSO-d$_6$) δ 8.28 (d, 1H), 7.63 (dd, 2H), 7.49 (t, 1H), 7.37 (d, 1H), 7.30 (t, 2H), 7.10 (broad, 1H), 6.89 (broad, 1H), 4.09 (m, 1H), 1.90–1.83 (m, 2H), 1.73–1.62 (m, 2H), 1.56–1.43 (m, 4H); $^{19}$F NMR (DMSO-d$_6$) δ –113.40; MS m/z 452 (M+1).

EXAMPLE 28

N-cyclopentyl-2-(4-fluorophenyl)-3-(4-pyridinyl)pyrazolo[1,5-α]pyridin-7-amine

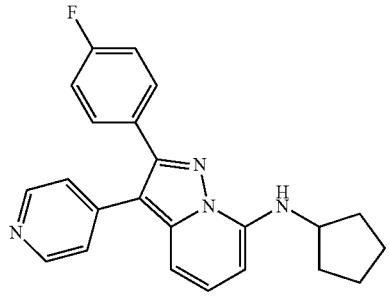

a) 3-bromo-7-chloro-2-(4-fluorophenyl)pyrazolo[1,5-α]pyridine

To a cold (0° C.) solution of 7-chloro-2-(4-fluorophenyl)pyrazolo[1,5-α]pyridine (5.0 g, 20.2 mmol) in tetrahydrofuran (81 mL) was added N-bromosuccinimide (3.79 g, 21.2 mmol) in two portions. The solution solidified after 5 minutes and additional tetrahydrofuran was added (20 mL). The resultant solution was stirred for 15 minutes. Saturated aqueous sodium bicarbonate and ether were added and the layers separated. The organic layer was washed with brine. The aqueous layers were extracted with ethyl acetate and the combined organics were dried over magnesium sulfate. Filtration and concentration followed by recrystallization from ethyl acetate-hexane-methanol provided 3-bromo-7-chloro-2-(4-fluorophenyl)pyrazolo[1,5-α]pyridine (5.7 g, 87%) as a crystalline solid. $^1$H NMR (CDCl$_3$) δ 8.07 (dd, 2H), 7.53 (d, 1H), 7.23–7.16 (m, 3H), 6.98 (d, 1H); $^{19}$F NMR (CDCl$_3$) δ –112.60; MS m/z 325 (M+1).

b) 3-Bromo-N-cyclopentyl-2-(4-fluorophenyl)pyrazolo[1,5-α]pyridin-7-amine

To a solution of 3-bromo-7-chloro-2-(4-fluorophenyl)pyrazolo[1,5-α]pyridine (1.26 g, 3.9 mmol) in toluene (39 mL) was added successively racemic-BINAP (153 mg, 0.23 mmol), cesium carbonate (1.44 g, 3.9 mmol), cyclopentylamine (1.14 mL, 11.5 mmol), and palladium (II) acetate (35 mg, 0.15 mmol). The resultant mixture was heated at 95° C. for 2.5 hours at which time the reaction was judged complete by thin layer chromatography. The solution was cooled to room temperature and ether was added. The organic layer was washed with water and brine. The aqueous layer was extracted with ether and the combined organics dried over magnesium sulfate. Filtration and concentration followed by flash chromatography (100:1 to 40:1 hexanes:ether) provided 3-bromo-N-cyclopentyl-2-(4-fluorophenyl)pyrazolo[1,5-α]pyridin-7-amine (1.2 g, 83%) as a white crystalline solid upon standing. $^1$H NMR (CDCl$_3$): δ 8.05 (dd, 2H), 7.22–7.14 (m, 3H), 6.87 (d, 1H), 5.95–5.92 (m, 2H), 4.00 (m, 1H). 2.13 (m, 2H), 1.84–1.67 (m, 6H); $^{19}$F NMR (CDCl$_3$) δ –113.44; MS m/z 374 (M+1).

c) N-Cyclopentyl-2-(4-fluorophenyl)-3-(4-pyridinyl)pyrazolo[1,5-α]pyridin-7-amine To a solution of 3-bromo-N-cyclopentyl-2-(4-fluorophenyl)pyrazolo[1,5-α]pyridin-7-amine (106 mg, 0.28 mmol) in N,N-dimethylformamide (5 mL) was added 4-pyridinylboronic acid (70 mg, 0.56 mmol), sodium carbonate (0.28 mL, 2 M aqueous, 0.56 mmol) and dichlorobis(triphenylphosphine)palladium(II) (10 mg, 0.01 mmol). The resultant solution was heated to 100° C. for 18 hours. The reaction mixture was cooled to room temperature and ether was added. The organic layer was washed with water and brine. The aqueous layer was extracted with ether and the combined organics dried over magnesium sulfate. Filtration and concentration followed by flash chromatography (2:1 hexanes:ether) provided N-cyclopentyl-2-(4-fluorophenyl)-3-(4-pyridinyl)pyrazolo[1,5-α]pyridin-7-amine (48 mg, 46%) as a yellow solid. $^1$H NMR (CDCl$_3$): δ 8.50 (d, 2H), 7.53 (m, 2H), 7.22–7.18 (m, 3H), 7.06–6.97 (m, 3H), 6.00 (d, 1H), 5.95 (d, 1H), 3.99 (m, 1H), 2.16–2.08 (m, 2H), 1.83–1.66 (m, 6H); $^{13}$C NMR (CDCl$_3$) δ 162.99 (d, J$_{CF}$=246.6 Hz), 150.07, 149.98, 142.77, 141.98, 140.13, 131.02 (d, J$_{CF}$=8.0 Hz), 129.04, 127.64, 123.98, 115.56 (d, J$_{CF}$=21.2 Hz), 106.51, 102.22, 89.25, 53.88, 33.36, 24.05; $^{19}$F NMR (CDCl$_3$) δ –113.49; MS m/z 373 (M+1).

EXAMPLE 29

N-Cyclopentyl-3-[2-(cyclopentylamino)-4-pyridinyl]-2-(4-fluorophenyl)pyrazolo[1,5-α]pyridin-7-amine

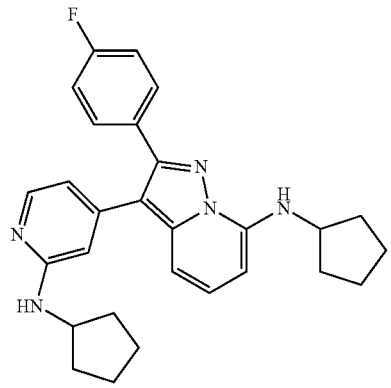

a) 2-Fluoropyridin-4-ylboronic acid

To a stirred solution of n-butyl lithium (3.2 mL, 2.5M, 8.0 mmol) in dry diethyl ether (20 mL) at –78° C. was added a solution of 2-fluoro-4-iodopyridine (1.5 g, 6.7 mmol) in dry ether (10 mL) and the reaction mixture was stirred at –78° C. for 10 minutes. Tributyl borate (2.4 mL, 2.01 g, 8.7 mmol) was added and the reaction mixture was allowed to warm to room temperature over 2 hours. Water (5 mL) was added followed by 2N aqueous sodium hydroxide solution (10 mL) to dissolve the solids. The organic phase was separated. The aqueous phase was acidified to pH3 using 6N hydrochloric acid and the resulting white solid was collected by filtration and dried under vacuum to give the title compound, 0.74 g (78%). $^1$H NMR (DMSO-d$_6$) δ 8.65 (br s, 2H), 8.21 (d, 1H), 7.59 (t, 1H), 7.37 (d, 1H).

b) N-Cyclopentyl-2-(4-fluorophenyl)-3-(2-fluoro-4-pyridinyl)pyrazolo[1,5-α]pyridin-7-amine In a similar manner to that in Example 28, from 3-bromo-N-cyclopentyl-2-(4-fluorophenyl)pyrazolo[1,5-α]pyridin-7-amine (240 mg, 0.64 mmol) and 2-fluoropyridin-4-ylboronic acid (271 mg, 1.92 mmol) after heating to 100° C. for 1.5 hours was formed N-cyclopentyl-2-(4-fluorophenyl)-3-(2-fluoro-4-pyridinyl)pyrazolo[1,5-α]pyridin-7-amine (180 mg, 72%) as a greenish solid. $^1$H NMR (CDCl$_3$): δ 8.12 (d, 1H), 7.56 (m, 2H), 7.27 (m, 1H), 7.13–7.02 (m, 4H), 6.90 (s, 1H), 6.05–6.01 (m, 2H), 4.02 (m, 1H), 2.16 (m, 2H), 1.86–1.68 (m, 6H); $^{19}$F NMR (CDCl$_3$) δ −68.65, −113.06; MS m/z 391 (M+1).

c) N-Cyclopentyl-3-[2-(cyclopentylamino)-4-pyridinyl]-2-(4-fluorophenyl)pyrazolo[1,5-α]pyridin-7-amine A solution of N-cyclopentyl-2-(4-fluorophenyl)-3-(2-fluoro-4-pyridinyl)pyrazolo[1,5-α]pyridin-7-amine (37 mg, 0.10 mmol) in cyclopentylamine (4 mL) was heated to 150° C. in a sealed tube for 12 hours. Upon cooling to room temperature, the mixture was concentrated in vacuo and the residue was taken up in ether and washed with water and then brine. The aqueous layer was extracted with ether and the combined organics were dried over magnesium sulfate. Filtration and concentration followed by flash chromatography (4:1 to 2:1 hexanes:ethyl acetate) provided N-cyclopentyl-3-[2-(cyclopentylamino)-4-pyridinyl]-2-(4-fluorophenyl)pyrazolo[1,5-α]pyridin-7-amine (31 mg, 72%) as a solid. $^1$H NMR (CDCl$_3$): δ 8.01 (d, 1H), 7.64 (dd, 2H), 7.21 (t, 1H), 7.10–7.02 (m, 3H), 6.57 (d, 1H), 6.34 (s, 1H), 6.01 (d, 1H), 5.97 (d, 1H), 4.63 (broad, 1H), 4.02 (m, 1H), 3.79 (m, 1H), 2.16 (m, 2H), 1.96–1.42 (m, 14H); $^{19}$F NMR (CDCl$_3$) δ −114.06; MS m/z 456 (M+1).

EXAMPLE 30

N-Cyclopentyl-2-(4-fluorophenyl)-3-(2-hydrazino-4-pyridinyl)pyrazolo[1,5-α]pyridin-7-amine

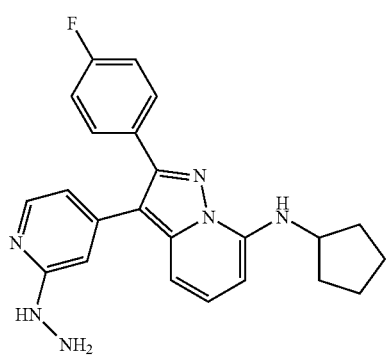

In a similar manner as described in Example 29, from N-cyclopentyl-2-(4-fluorophenyl)-3-(2-fluoro-4-pyridinyl)pyrazolo[1,5-α]pyridin-7-amine (45 mg, 0.12 mmol) and anhydrous hydrazine (0.5 mL) in ethanol (4 mL) at 100° C. for 13 hours was formed N-cyclopentyl-2-(4-fluorophenyl)-3-(2-hydrazino-4-pyridinyl)pyrazolo[1,5-α]pyridin-7-amine (30 mg, 65%) as a solid. $^1$H NMR (CDCl$_3$): δ 8.05 (d, 1H), 7.61 (m, 2H), 7.20 (t, 1H), 7.09–6.99 (m, 4H), 6.71 (s, 1H), 6.63 (d, 1H), 6.03–5.96 (m, 3H), 4.01 (broad m, 2H), 2.14 (m, 2H), 1.84–1.68 (m, 6H); $^{19}$F NMR (CDCl$_3$) δ −113.66; MS m/z 403 (M+1).

EXAMPLE 31

N-Cyclopentyl-4-[2-(4-fluorophenyl)-7-(1-pyrrolidinyl)pyrazolo[1,5-α]pyridin-3-yl]-2-pyrimidinamine

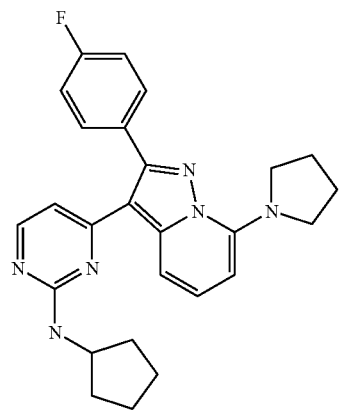

a) 1-[2-(4-Fluorophenyl)-7-(1-pyrrolidinyl)pyrazolo[1,5-α]pyridin-3-yl]ethanone

In a similar manner as described in Example 1, from 1-[7-chloro-2-(4-fluorophenyl)-pyrazolo[1,5-α]pyridin-3-yl]ethanone (0.30 g, 1.0 mmol) and pyrrolidine (0.43 mL, 5.2 mmol), 1-[2-(4-fluorophenyl)-7-(1-pyrrolidinyl)pyrazolo[1,5-α]pyridin-3-yl]ethanone (0.30 g, 91%) was obtained as a yellow solid. $^1$H NMR (CDCl$_3$): δ 7.78 (d, 1H), 7.56 (m, 2H), 7.36 (t, 1H), 7.13 (t, 2H), 6.16 (d, 1H), 3.72 (m, 4H), 2.11 (s, 3H), 1.99 (m, 4H); MS m/z 324 (M+1).

b) (2E)-3-(Dimethylamino)-1-[2-(4-fluorophenyl)-7-(1-pyrrolidinyl)pyrazolo[1,5-α]pyridin-3-yl]-2-propen-1-one In a similar manner as described in Example 1, from 1-[2-(4-fluorophenyl)-7-(1-pyrrolidinyl)pyrazolo[1,5-α]pyridin-3-yl]ethanone (0.28 g, 0.86 mmol), (2E)-3-(dimethylamino)-1-[2-(4-fluorophenyl)-7-(1-pyrrolidinyl)pyrazolo[1,5-α]pyridin-3-yl]-2-propen-1-one (0.25 g, 76%) was obtained as a yellow foam. $^1$H NMR (CDCl$_3$): δ 7.75 (m, 3H), 7.58 (d, 1H), 7.25 (t, 1H), 7.11 (t, 2H), 6.09 (d, 1H), 5.09 (d, 1H), 3.73 (m, 4H), 2.93 (bs, 3H), 2.62 (bs, 3H), 2.02 (m, 4H); MS m/z 379 (M+1).

c) N-Cyclopentyl-4-[2-(4-fluorophenyl)-7-(1-pyrrolidinyl)pyrazolo[1,5-α]pyridin-3-yl]-2-pyrimidinamine In a similar manner as described in Example 1, from (2E)-3-(dimethylamino)-1-[2-(4-fluorophenyl)-7-(1-pyrrolidinyl)pyrazolo[1,5-α]pyridin-3-yl]-2-propen-1-one (75 mg, 0.20 mmol), N-cyclopentylguanidine hydrochloride and potassium carbonate in N,N-dimethylformamide was obtained N-cyclopentyl-4-[2-(4-fluorophenyl)-7-(1-pyrrolidinyl)pyrazolo[1,5-α]pyridin-3-yl]-2-pyrimidinamine (28.7 mg, 33%) as a yellow solid. $^1$H NMR (CDCl$_3$): δ 7.95 (d, 1H), 7.82 (d, 1H), 7.61 (m, 2H), 7.22 (t, 1H), 7.08 (t, 2H), 6.28 (d, 1H), 6.07 (d, 1H), 5.25 (bs, 1H), 4.31 (m, 1H), 3.72 (m, 4H), 2.02 (m, 6H), 1.75–1.49 (m, 6H); MS m/z 443 (M+1).

EXAMPLE 32

4-[2-(4-Fluorophenyl)-7-(1-pyrrolidinyl)pyrazolo[1,5-α]pyridin-3-yl]-N,N-dimethyl-2-pyrimidinamine

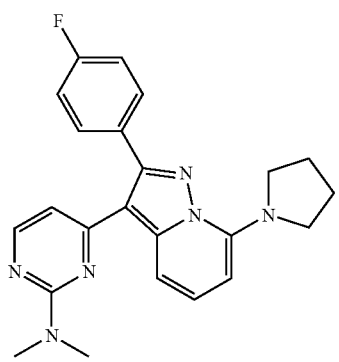

In a similar manner as described in Example 1, from (2E)-3-(dimethylamino)-1-[2-(4-fluorophenyl)-7-(1-pyrrolidinyl)pyrazolo[1,5-α]pyridin-3-yl]-2-propen-1-one (75 mg, 0.20 mmol), N,N-dimethylguanidine sulfate and potassium carbonate in N,N-dimethylformamide was obtained 4-[2-(4-fluorophenyl)-7-(1-pyrrolidinyl)pyrazolo[1,5-α]pyridin-3-yl]-N,N-dimethyl-2-pyrimidinamine (19.8 mg, 25%) as a yellow crystalline solid. $^1$H NMR (CDCl$_3$): δ 8.05 (d, 1H), 7.81 (d, 1H), 7.61 (m, 2H), 7.21 (t, 1H), 7.07 (t, 2H), 6.27 (d, 1H), 6.06 (d, 1H), 3.71 (m, 4H), 3.21 (s, 6H), 2.01 (m, 4H); MS m/z 403 (M+1).

EXAMPLE 33

3-[2-(Butylamino)-4-pyrimidinyl]-N-cyclopropyl-2-(4-fluorophenyl)pyrazolo[1,5-α]pyridin-7-amine

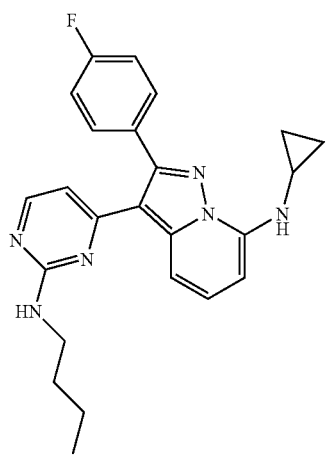

a) N-Butyl-4-[7-chloro-2-(4-fluorophenyl)pyrazolo[1,5-α]pyridin-3-yl]-2-pyrimidinamine In a similar manner as described in Example 7 from 1-[7-chloro-2-(4-fluorophenyl)pyrazolo[1,5-α]pyridin-3-yl]-2-propyn-1-one (0.50 g, 1.7 mmol), N-butylguanidine sulfate and sodium ethoxide (0.81 mL, 21 wt % in ethanol, 2.2 mmol) at room temperature was obtained N-butyl-4-[7-chloro-2-(4-fluorophenyl)pyrazolo[1,5-α]pyridin-3-yl]-2-pyrimidinamine (0.39 g, 59%) as a fluffy pale yellow solid. $^1$H NMR (CDCl$_3$): δ 8.40 (d, 1H), 8.07 (d, 1H), 7.65 (m, 2H), 7.29 (m, 1H), 7.15 (t, 2H), 7.06 (d, 1H), 6.32 (d, 1H), 5.16 (bs, 1H), 3.49 (q, 2H), 1.71–1.41 (m, 4H), 0.99 (t, 3H); $^{19}$F NMR (CDCl$_3$) δ −112.77; MS m/z 396 (M+1).

b) 3-[2-(Butylamino)-4-pyrimidinyl]-N-cyclopropyl-2-(4-fluorophenyl)pyrazolo[1,5-α]pyridin-7-amine In a similar manner as described in Example 1, from N-butyl-4-[7-chloro-2-(4-fluorophenyl)pyrazolo[1,5-α]pyridin-3-yl]-2-pyrimidinamine (46 mg, 0.12 mmol) and cyclopropylamine was obtained 3-[2-(butylamino)-4-pyrimidinyl]-N-cyclopropyl-2-(4-fluorophenyl)pyrazolo[1,5-α]pyridin-7-amine (36.5 mg, 75%) as a yellow foam. $^1$H NMR (CDCl$_3$): δ 7.95 (d, 1H), 7.75 (d, 1H), 7.58 (m, 2H), 7.32 (t, 1H), 7.11 (t, 2H), 6.36 (d, 1H), 6.27 (s, 1H), 6.24 (d, 1H), 5.15 (bs, 1H), 3.43 (q, 2H), 2.63 (m, 1H), 1.61 (m, 2H), 1.42 (m, 2H), 0.94 (t, 3H), 0.84 (m, 2H), 0.71 (m, 2H); MS m/z 417 (M+1).

EXAMPLE 34

3-[2-(Butylamino)-4-pyrimidinyl]-2-(4-fluorophenyl)-N,N-dimethylpyrazolo[1,5-α]pyridin-7-amine

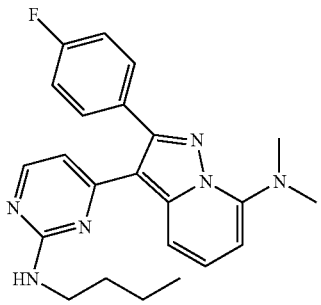

a) (2E)-1-[7-Chloro-2-(4-fluorophenyl)pyrazolo[1,5-α]pyridin-3-yl]-3-(dimethylamino)-2-propen-1-one In a similar manner as described in Example 1, from 1-[7-chloro-2-(4-fluorophenyl)pyrazolo[1,5-α]pyridin-3-yl]ethanone (1.83 g, 6.3 mmol) was obtained (2E)-1-[7-chloro-2-(4-fluorophenyl)pyrazolo[1,5-α]pyridin-3-yl]-3-(dimethylamino)-2-propen-1-one (1.47 g, 67%) as a yellow solid. $^1$H NMR (acetone-d$_6$): δ 8.21 (d, 1H), 7.79 (m, 2H), 7.50 (d, 1H), 7.38 (t, 1H), 7.23 (m, 3H), 5.07 (d, 1H), 3.04 (bs, 3H), 2.54 (bs, 3H); MS m/z 344 (M+1).

b) 3-[2-(Butylamino)-4-pyrimidinyl]-2-(4-fluorophenyl)-N,N-dimethylpyrazolo[1,5-α]pyridin-7-amine In a similar manner as described in Example 1, from (2E)-1-[7-chloro-2-(4-fluorophenyl)pyrazolo[1,5-α]pyridin-3-yl]-3-(dimethylamino)-2-propen-1-one (1.47 g, 4.3 mmol), N-butylguanidine sulfate and potassium carbonate in N,N-dimethylformamide was obtained 3-[2-(butylamino)-4-pyrimidinyl]-2-(4-fluorophenyl)-N,N-dimethylpyrazolo[1,5-α]pyridin-7-amine (0.40 g, 24%) as a yellow solid. $^1$H NMR (CDCl$_3$): δ 8.00 (m, 2H), 7.62 (m, 2H), 7.28 (t, 1H), 7.08 (t, 2H), 6.29 (m, 2H), 5.24 (bs, 1H), 3.44 (m, 2H), 3.09 (s, 6H), 1.65–1.38 (m, 4H), 0.94 (t, 3H); MS m/z 405 (M+1).

EXAMPLE 35

N-Butyl-4-[2-(4-fluorophenyl)-7-(4-methyl-1-piperazinyl)pyrazolo[1,5-α]pyridin-3-yl]-2-pyrimidinamine

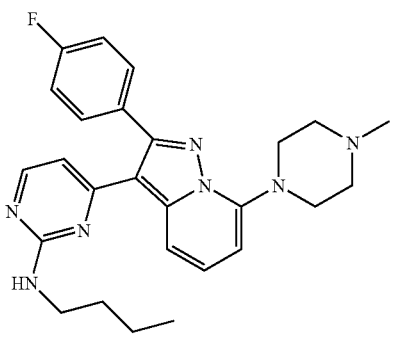

In a similar manner as described in Example 1, from N-butyl-4-[7-chloro-2-(4-fluorophenyl)pyrazolo[1,5-α]pyridin-3-yl]-2-pyrimidinamine (50 mg, 0.13 mmol) and 1-methylpiperazine was prepared N-butyl-4-[2-(4-fluorophenyl)-7-(4-methyl-1-piperazinyl)pyrazolo[1,5-α]pyridin-3-yl]-2-pyrimidinamine (28 mg, 48%) as an off-white foam. $^1$H NMR (DMSO-d$_6$): δ 7.98 (m, 2H), 7.58 (t, 2H), 7.35 (t, 1H), 7.26 (t, 2H), 7.04 (bs, 1H), 6.46 (d, 1H), 6.14 (bs, 1H), 3.37 (bs, 4H), 3.20 (d, 2H), 2.49 (s, 4H), 2.20 (s, 3H), 1.46 (m, 2H), 1.28 (m, 2H), 0.84 (t, 3H); $^{19}$F NMR (DMSO-d$_6$) δ −113.56; MS m/z 460 (M+1).

EXAMPLE 36

N-Butyl-4-[2-(4-fluorophenyl)-7-(4-morpholinyl)pyrazolo[1,5-α]pyridin-3-yl]-2-pyrimidinamine

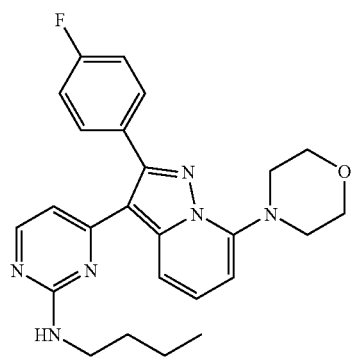

In a similar manner as described in Example 1, from N-butyl-4-[7-chloro-2-(4-fluorophenyl)pyrazolo[1,5-α]pyridin-3-yl]-2-pyrimidinamine (50 mg, 0.13 mmol) and morpholine was prepared N-butyl-4-[2-(4-fluorophenyl)-7-(4-morpholinyl)-pyrazolo[1,5-α]pyridin-3-yl]-2-pyrimidinamine (24 mg, 44%) as an off-white foam. $^1$H NMR (CDCl$_3$): δ 8.14 (d, 1H), 8.03 (m, 1H), 7.68 (m, 2H), 7.37 (t, 1H), 7.17 (t, 2H), 6.39 (m, 2H), 5.52 (bs, 1H), 4.04 (m, 4H), 3.66 (m, 6H), 1.70 (m, 2H), 1.52 (m, 2H), 1.02 (t, 3H); MS m/z 447 (M+1).

EXAMPLE 37

N-Butyl-2-(4-fluorophenyl)-3-[2-(methylsulfinyl)-4-pyrimidinyl]-pyrazolo[1,5-α]pyridin-7-amine

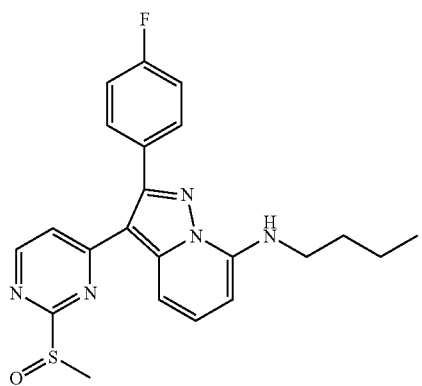

a) 4-[7-(Butylamino)-2-(4-fluorophenyl)pyrazolo[1,5-α]pyridin-3-yl]-2-pyrimidinethiolate A solution of (2E)-1-[7-(butylamino)-2-(4-fluorophenyl)pyrazolo[1,5-α]pyridin-3-yl]-3-(dimethylamino)-2-propen-1-one (5.92 g, 15.6 mmol), thiourea (2.37 g, 31.1 mmol) and potassium hydroxide (15.6 mL, 1.0 N in ethanol) in 200 mL of ethanol was heated to reflux until starting material was consumed. The reaction was cooled to room temperature and the resulting precipitate was isolated by filtration. After washing with ethyl acetate, 4-[7-(butylamino)-2-(4-fluorophenyl)pyrazolo[1,5-α]pyridin-3-yl]-2-pyrimidinethiolate (1.68 g, 44%) was isolated as a tan solid as the potassium salt. $^1$H NMR (DMSO-d$_6$): δ 7.68–7.61 (m, 4H), 7.29–7.23 (m, 3H), 6.88 (m, 1H), 6.08 (d, 1H), 6.00 (d, 1H), 3.32–3.22 (m, 2H), 1.59 (m, 2H), 1.34 (m, 2H), 0.87 (t, 3H); MS m/z 392 (M+1).

b) N-Butyl-2-(4-fluorophenyl)-3-[2-(methylsulfanyl)-4-pyrimidinyl]pyrazolo[1,5-α]pyridin-7-amine A mixture of 4-[7-(butylamino)-2-(4-fluorophenyl)pyrazolo[1,5-α]pyridin-3-yl]-2-pyrimidinethiolate (2.87 g, 6.9 mmol) in 50 mL water was treated with iodomethane (0.86 mL, 13.8 mmol) and sodium hydroxide (4.1 mL, 5 N aqueous solution) and allowed to stir at room temperature for 4 hours. The mixture was diluted with additional water and extracted with dichloromethane. The organic layers were washed with brine, dried over magnesium sulfate and concentrated. Flash column chromatography eluting with 9:1 hexanes-ethyl acetate afforded N-butyl-2-(4-fluorophenyl)-3-[2-(methylsulfanyl)-4-pyrimidinyl]pyrazolo[1,5-α]pyridin-7-amine (1.64 g, 56%) as a yellow foam. $^1$H NMR (CDCl$_3$): δ 8.15 (d, 1H), 7.73 (d, 1H), 7.56 (m, 2H), 7.33 (t, 1H), 7.13 (t, 2H), 6.62 (d, 1H), 6.02 (m, 2H), 3.35 (q, 2H), 2.55 (s, 3H), 1.76–1.41 (m, 4H), 0.95 (t, 3H); $^{19}$F NMR (CDCl$_3$): δ −112.75; MS m/z 408 (M+1).

c) N-Butyl-2-(4-fluorophenyl)-3-[2-(methylsulfinyl)-4-pyrimidinyl]pyrazolo[1,5-α]pyridin-7-amine To a cold (0° C.) solution of N-butyl-2-(4-fluorophenyl)-3-[2-(methylsulfanyl)-4-pyrimidinyl]pyrazolo[1,5-α]pyridin-7-amine (1.51 g, 3.7 mmol) in 50 mL chloroform was added m-chloroperbenzoic acid (0.87 g, 70–75%, 3.7 mmol). The reaction was allowed to warm to rt. After stirring for 5 h, another 0.2 g m-chloroperbenzoic acid was added and the reaction was stirred for 15 min. The reaction was diluted with aqueous sodium bicarbonate and extracted with dichloromethane. The organic extracts were washed with brine, dried over magnesium sulfate and concentrated. The crude product was recrystallized from ethyl acetate-hexanes to afford N-butyl-2-(4-fluorophenyl)-3-[2-(methylsulfinyl)-4-pyrimidinyl]pyrazolo[1,5-α]pyridin-7-amine (0.95 g, 60%) as an orange solid. $^1$H NMR (CDCl$_3$): δ 8.40 (broad, 1H), 7.99 (d, 1H), 7.58 (m, 2H), 7.45 (t, 1H), 7.20 (t, 2H), 6.94 (d, 1H), 6.13 (d, 1H), 6.10 (broad, 1H), 3.38 (m, 2H), 2.98 (s, 3H), 1.79–1.42 (m, 4H), 0.97 (t, 3H); MS m/z 422 (M−1).

EXAMPLE 38

3-({4-[7-(Butylamino)-2-(4-fluorophenyl)pyrazolo[1,5-α]pyridin-3-yl]-2-pyrimidinyl}amino)-1-propanol

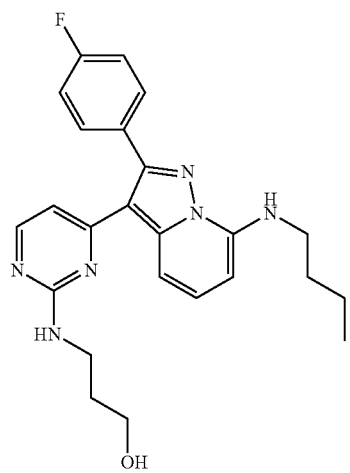

A solution of N-butyl-2-(4-fluorophenyl)-3-[2-(methylsulfinyl)-4-pyrimidinyl]pyrazolo[1,5-α]pyridin-7-amine (50 mg, 0.12 mmol) and 3-amino-1-propanol (0.45 mL, 5.9 mmol) in 2 mL tetrahydrofuran was heated to reflux for 4 hours, then the mixture was cooled to room temperature and concentrated. Flash column chromatography eluting with a gradient of 0% to 100% ethyl acetate in hexanes afforded 3-({4-[7-(butylamino)-2-(4-fluorophenyl)pyrazolo[1,5-α]pyridin-3-yl]-2-pyrimidinyl}amino)-1-propanol (46.3 mg, 90%) as a yellow foam. $^1$H NMR (CDCl$_3$): δ 7.97 (d, 1H), 7.67–7.61 (m, 3H), 7.35 (t, 1H), 7.16 (t, 2H), 6.34 (d, 1H), 6.04 (m, 2H), 3.67–3.60 (m, 4H), 3.39 (q, 2H), 1.79–1.45 (m, 6H), 1.00 (t, 3H); $^{19}$F NMR (CDCl$_3$): δ −113.10; MS m/z 435 (M+1).

EXAMPLE 39

3-[2-(Allylamino)-4-pyrimidinyl]-N-butyl-2-(4-fluorophenyl)pyrazolo-[1,5-α]pyridin-7-amine

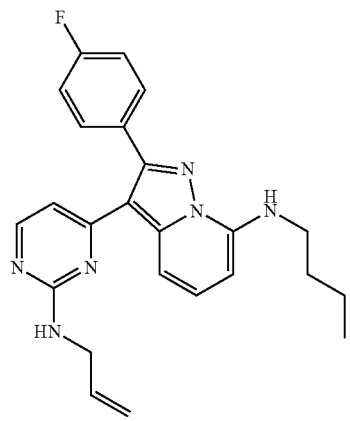

In a similar manner as described in Example 38, from N-butyl-2-(4-fluorophenyl)-3-[2-(methylsulfinyl)-4-pyrimidinyl]pyrazolo[1,5-α]pyridin-7-amine (50 mg, 0.12 mmol) and allylamine, heated at 60° C. for 24 h was prepared 3-[2-(allylamino)-4-pyrimidinyl]-N-butyl-2-(4-fluorophenyl)pyrazolo[1,5-α]pyridin-7-amine (44.6 mg, 91%) as a yellow foam. $^1$H NMR (CDCl$_3$): δ 7.99 (d, 1H), 7.74 (d, 1H), 7.63 (m, 2H), 7.34 (t, 1H), 7.17 (t, 2H), 6.33 (d, 1H), 6.06–5.98 (m, 3H), 5.32 (dd, 1H), 5.19 (dd, 1H), 4.15 (t, 2H), 3.39 (q, 2H), 1.80–1.46 (m, 4H), 1.00 (t, 3H); $^{19}$F NMR (CDCl$_3$): δ −113.17 MS m/z 417 (M+1).

EXAMPLE 40

N-Butyl-2-(4-fluorophenyl)-3-[2-(4-morpholinyl)-4-pyrimidinyl]pyrazolo[1,5-α]pyridin-7-amine

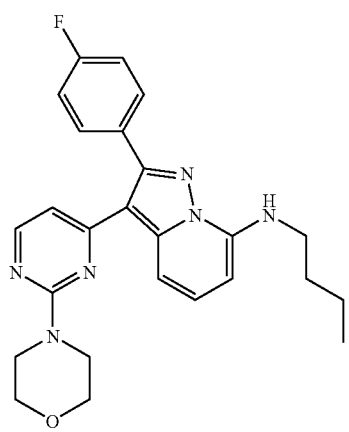

In a similar manner as described in Example 38, from N-butyl-2-(4-fluorophenyl)-3-[2-(methylsulfinyl)-4-pyrimidinyl]pyrazolo[1,5-α]pyridin-7-amine (50 mg, 0.12 mmol) and morpholine was prepared N-butyl-2-(4-fluorophenyl)-3-[2-(4-morpholinyl)-4-pyrimidinyl]pyrazolo[1,5-α]pyridin-7-amine (43.0 mg, 82%) as an off-white foam. $^1$H NMR (DMSO-d$_6$): δ 8.09 (d, 1H), 7.56 (dd, 2H), 7.44 (d, 1H), 7.35 (t, 1H), 7.26 (t, 2H), 7.06 (t, 1H), 6.30 (d, 1H), 6.14 (d, 1H), 3.59 (m, 8H), 3.28 (m, 2H), 1.59 (m, 2H), 1.33 (m, 2H), 0.87 (t, 3H); $^{19}$F NMR (DMSO-d$_6$): δ −113.70; MS m/z 447 (M+1).

EXAMPLE 41

2-(4-{4-[7-(Butylamino)-2-(4-fluorophenyl)pyrazolo[1,5-α]pyridin-3-yl]-2-pyrimidinyl}-1-piperazinyl)ethanol

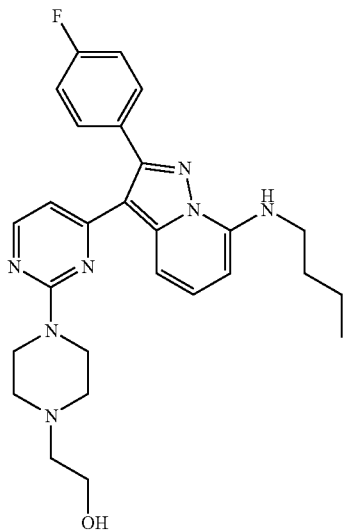

In a similar manner as described in Example 38, from N-butyl-2-(4-fluorophenyl)-3-[2-(methylsulfinyl)-4-pyrimidinyl]pyrazolo[1,5-α]pyridin-7-amine (50 mg, 0.12 mmol) and 1-(2-hydroxyethyl)piperazine was prepared 2-(4-{4-[7-(butylamino)-2-(4-fluorophenyl)pyrazolo[1,5-α]pyridin-3-yl]-2-pyrimidinyl}-1-piperazinyl)ethanol (47.8 mg, 83%) as a pale yellow solid. $^1$H NMR (DMSO-d$_6$): δ 8.12 (d, 1H), 7.61 (m, 2H), 7.48 (d, 1H), 7.39 (t, 1H), 7.30 (t, 2H), 7.09 (t, 1H), 6.31 (d, 1H), 6.18 (d, 1H), 4.43 (broad, 1H), 3.64 (broad, 4H), 3.53 (q, 2H), 3.38–3.27 (m, 4H), 2.44 (broad, 4H), 1.63 (m, 2H), 1.37 (m, 2H), 0.91 (t, 3H); $^{19}$F NMR (CDCl$_3$): δ −113.30; MS m/z 490 (M+1).

EXAMPLE 42

N-Butyl-2-(4-fluorophenyl)-3-{2-[4-(2-methoxyethyl)-1-piperazinyl]-4-pyrimidinyl}pyrazolo[1,5-α]pyridin-7-amine

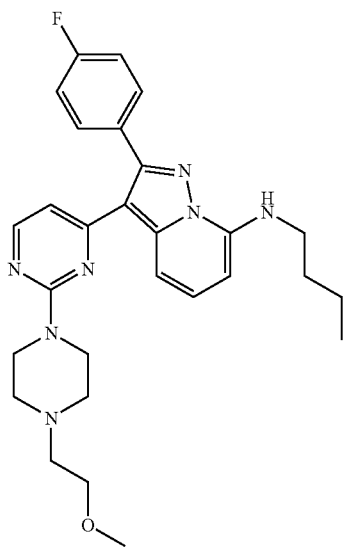

In a similar manner as described in Example 38, from N-butyl-2-(4-fluorophenyl)-3-[2-(methylsulfinyl)-4-pyrimidinyl]pyrazolo[1,5-α]pyridin-7-amine (50 mg, 0.12 mmol) and 1-(2-methoxyethyl)piperazine was prepared N-butyl-2-(4-fluorophenyl)-3-{2-[4-(2-methoxyethyl)-1-piperazinyl]-4-pyrimidinyl}pyrazolo[1,5-α]pyridin-7-amine (59.9 mg, 100%) as a pale yellow oil. $^1$H NMR (DMSO-d$_6$): δ 8.11 (d, 1H), 7.61 (dd, 2H), 7.48 (d, 1H), 7.40 (t, 1H), 7.30 (t, 2H), 7.09 (t, 1H), 6.31 (d, 1H), 6.18 (d, 1H), 3.64 (broad, 4H), 3.46 (t, 2H), 3.38–3.22 (m, 7H), 2.44 (broad, 4H), 1.63 (m, 2H), 1.38 (m, 2H), 0.92 (t, 3H); $^{19}$F NMR (CDCl$_3$): δ −113.59 MS m/z 504 (M+1). This material was treated with anhydrous hydrochloride in ether to provide a hydrochloride salt as an orange solid.

EXAMPLE 43

N-Butyl-2-(4-fluorophenyl)-3-{2-[(2-pyridinylmethyl)amino]-4-pyrimidinyl}pyrazolo[1,5-α]pyridin-7-amine

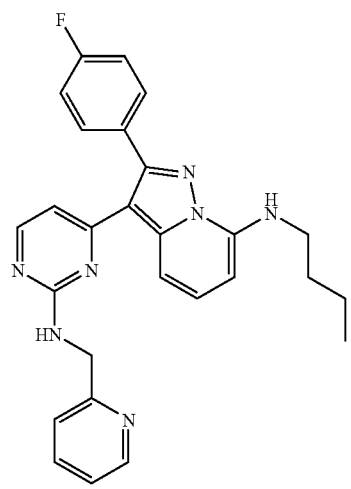

In a similar manner as described in Example 38, from N-butyl-2-(4-fluorophenyl)-3-[2-(methylsulfinyl)-4-pyrimidinyl]pyrazolo[1,5-α]pyridin-7-amine (89 mg, 0.21 mmol), 2-picolylamine (0.6 mL, 5.8 mmol) and potassium carbonate (64 mg, 0.46 mmol) in xylenes at 140° C. for 24 h was prepared N-butyl-2-(4-fluorophenyl)-3-{2-[(2-pyridinylmethyl)amino]-4-pyrimidinyl}pyrazolo[1,5-α]pyridin-7-amine (39.2 mg, 40%) as a solid. $^1$H NMR (CDCl$_3$): δ 8.62 (d, 1H), 8.05 (d, 1H), 7.65 (m, 3H), 7.38 (d, 1H), 7.27–7.12 (m, 4H), 6.37 (d, 1H), 6.13 (broad, 1H), 6.02–6.00 (m, 2H), 4.83 (d, 2H), 3.38 (q, 2H), 1.75 (m, 2H), 1.49 (m, 2H), 0.99 (t, 3H); $^{19}$F NMR (CDCl$_3$): δ −113.22 MS m/z 468 (M+1). This material was treated with anhydrous hydrochloride in ether to provide a hydrochloride salt as a brown solid.

EXAMPLE 44

N-Butyl-2-(4-fluorophenyl)-3-(2-{[3-(1H-imidazol-1-yl)propyl]amino}-4-pyrimidinyl)pyrazolo[1,5-α]pyridin-7-amine

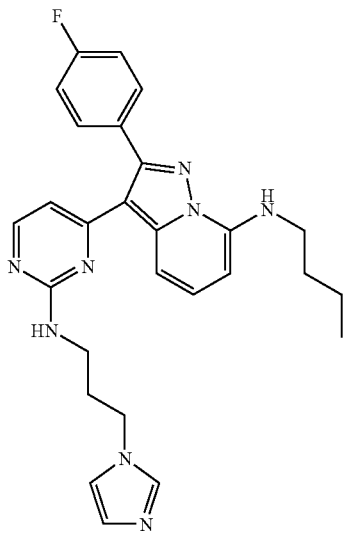

In a similar manner as described in Example 38, from N-butyl-2-(4-fluorophenyl)-3-[2-(methylsulfinyl)-4-pyrimidinyl]pyrazolo[1,5-α]pyridin-7-amine (50 mg, 0.12 mmol) and 1-(3-aminopropyl)imidazole in ethanol in a sealed tube at 90° C. was prepared N-butyl-2-(4-fluorophenyl)-3-(2-{[3-(1H-imidazol-1-yl)propyl]amino}-4-pyrimidinyl)pyrazolo[1,5-α]pyridin-7-amine (43.8 mg, 77%) as a yellow oil. $^1$H NMR (CDCl$_3$): δ 8.01 (d, 1H), 7.65–7.61 (m, 3H), 7.54 (s, 1H), 7.34 (t, 1H), 7.15 (t, 2H), 7.08 (s, 1H), 6.97 (s, 1H), 6.37 (d, 1H), 6.07–6.03 (m, 2H), 5.32 (broad, 1H), 4.08 (t, 2H), 3.48 (q, 2H), 3.39 (q, 2H), 2.14 (m, 2H), 1.77 (m, 2H), 1.51 (m, 2H), 1.00 (t, 3H); MS m/z 485 (M+1). This material was treated with anhydrous hydrochloride in ether to provide a hydrochloride salt as a gold solid.

EXAMPLE 45

N-Butyl-2-(4-fluorophenyl)-3-(2-{[2-(4-morpholinyl)ethyl]amino}-4-pyrimidinyl)pyrazolo[1,5-α]pyridin-7-amine

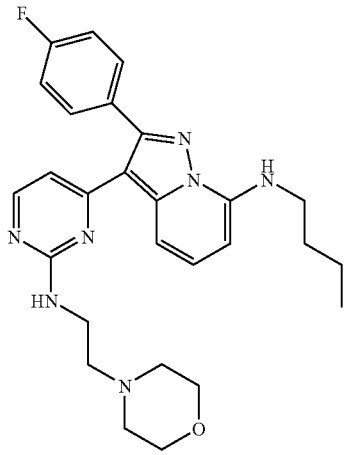

In a similar manner as described in Example 38, from N-butyl-2-(4-fluorophenyl)-3-[2-(methylsulfinyl)-4-pyrimidinyl]pyrazolo[1,5-α]pyridin-7-amine (50 mg, 0.12 mmol) and 4-(2-aminoethyl)morpholine in ethanol in a sealed tube at 90° C. was prepared N-butyl-2-(4-fluorophenyl)-3-(2-{[2-(4-morpholinyl)ethyl]amino}-4-pyrimidinyl)-pyrazolo[1,5-α]pyridin-7-amine (47.0 mg, 81%) as a yellow solid. $^1$H NMR (CDCl$_3$): δ 8.02 (d, 1H), 7.72 (d, 1H), 7.63 (dd, 2H), 7.33 (t, 1H), 7.14 (t, 2H), 6.31 (d, 1H), 6.03–6.01 (m, 2H), 5.65 (broad, 1H), 3.75 (broad, 4H), 3.57 (q, 2H), 3.39 (q, 2H), 2.65 (t, 2H), 2.53 (broad, 4H), 1.81–1.46 (m, 4H), 0.99 (t, 3H); $^{19}$F NMR (CDCl$_3$): δ −113.31 MS m/z 490 (M+1).

EXAMPLE 46

N-Butyl-2-(4-fluorophenyl)-3-{2-[2-(4-morpholinyl)ethoxy]-4-pyrimidinyl}pyrazolo[1,5-α]pyridin-7-amine

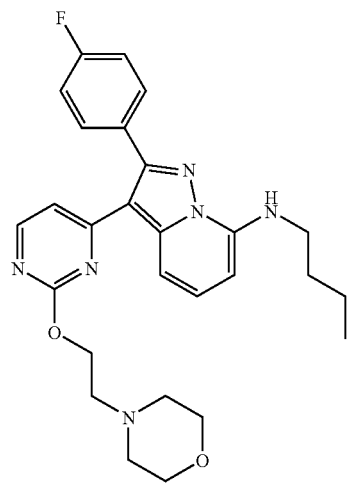

In a similar manner as described in Example 38, from N-butyl-2-(4-fluorophenyl)-3-[2-(methylsulfinyl)-4-pyrimidinyl]pyrazolo[1,5-α]pyridin-7-amine (50 mg, 0.12 mmol), 4-(2-hydroxyethyl)morpholine (71 μL, 0.59 mmol) and potassium t-butoxide (0.24 mL, 1.0 M in t-butanol, 0.24 mmol) in tetrahydrofuran at room temperature was prepared N-butyl-2-(4-fluorophenyl)-3-{2-[2-(4-morpholinyl)ethoxy]-4-pyrimidinyl}pyrazolo[1,5-α]pyridin-7-amine (37.0 mg, 64%) as a yellow oil. $^1$H NMR (CDCl$_3$): δ 8.19 (d, 1H), 7.77 (d, 1H), 7.60 (m, 2H), 7.37 (t, 1H), 7.17 (t, 2H), 6.65 (d, 1H), 6.08–6.03 (m, 2H), 4.55 (broad, 2H), 3.76 (broad, 4H), 3.39 (q, 2H), 2.88 (broad, 2H), 2.63 (broad, 4H), 1.81–1.46 (m, 4H), 1.00 (t, 3H); $^{19}$F NMR (CDCl$_3$): δ −112.88 MS m/z 491 (M+1). This material was treated with anhydrous hydrochloride in ether to provide a hydrochloride salt as an orange solid.

EXAMPLE 47

3-[2-(Butylamino)-4-pyrimidinyl]-2-(4-fluorophenyl)-N-[2-(4-morpholinyl)ethyl]pyrazolo[1,5-α]pyridin-7-amine

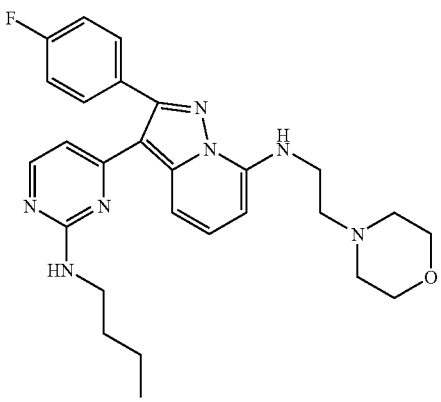

In a similar manner as described in Example 1, from N-butyl-4-[7-chloro-2-(4-fluorophenyl)pyrazolo[1,5-α]pyridin-3-yl]-2-pyrimidinamine (52.5 mg, 0.13 mmol) and 4-(2-aminoethyl)morpholine was prepared 3-[2-(butylamino)-4-pyrimidinyl]-2-(4-fluorophenyl)-N-[2-(4-morpholinyl)ethyl]pyrazolo[1,5-α]pyridin-7-amine (30.0 mg, 46%) as a yellow solid. $^1$H NMR (CDCl$_3$): δ 7.97 (broad, 1H), 7.76 (d, 1H), 7.65 (m, 2H), 7.34 (t, 1H), 7.16 (t, 2H), 6.54 (t, 1H), 6.32 (d, 1H), 6.04 (d, 1H), 3.76 (t, 4H), 3.48 (m, 4H), 2.78 (t, 2H), 2.55 (broad, 4H), 1.68–1.44 (m, 4H), 0.98 (t, 3H); MS m/z 490 (M+1).

EXAMPLE 48

3-[2-(Butylamino)-4-pyrimidinyl]-2-(4-fluorophenyl)-N-(2-methoxyethyl)pyrazolo[1,5-α]pyridin-7-amine

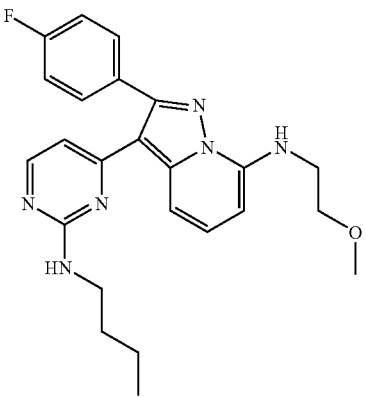

A mixture of N-butyl-4-[7-chloro-2-(4-fluorophenyl)pyrazolo[1,5-α]pyridin-3-yl]-2-pyrimidinamine (56 mg, 0.14 mmol) and 2-methoxyethylamine (5 mL) was heated to reflux for 24 hours, then cooled and concentrated. Flash column chromatography eluting with 3:1 hexanes:ethyl acetate afforded 3-[2-(butylamino)-4-pyrimidinyl]-2-(4- fluorophenyl)-N-(2-methoxyethyl)pyrazolo[1,5-α]pyridin-7-amine (57.1 mg, 93%) as a yellow foam. ¹H NMR (CDCl₃): δ 8.02 (d, 1H), 7.76 (d, 1H), 7.65 (m, 2H), 7.32 (t, 1H), 7.15 (t, 2H), 6.29 (m, 2H), 6.05 (d, 1H), 5.10 (broad, 1H), 3.72 (t, 2H), 3.57 (q, 2H), 3.47 (q, 2H), 3.43 (s, 3H), 1.69–1.44 (m, 4H), 0.98 (t, 3H); MS m/z 435 (M+1).

EXAMPLE 49

3-[2-(Butylamino)-4-pyrimidinyl]-2-(4-fluorophenyl)-N-methylpyrazolo[1,5-α]pyridin-7-amine

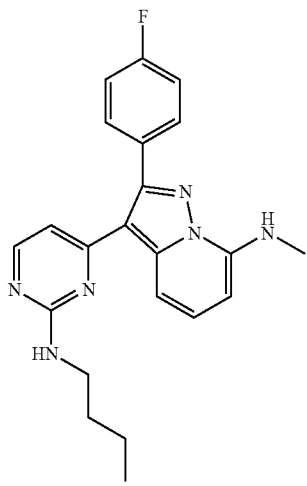

In a similar manner as described in Example 14, from N-butyl-4-[7-chloro-2-(4-fluorophenyl)pyrazolo[1,5-α]pyridin-3-yl]-2-pyrimidinamine (53 mg, 0.13 mmol) and methylamine (5 mL, 40% aqueous) in a sealed tube was obtained 3-[2-(butylamino)-4-pyrimidinyl]-2-(4-fluorophenyl)-N-methylpyrazolo[1,5-α]pyridin-7-amine (40.5 mg, 77%) as a pale yellow solid. ¹H NMR (CDCl₃): δ 8.01 (d, 1H), 7.75 (d, 1H), 7.62 (m, 2H), 7.34 (t, 1H), 7.13 (t, 2H), 6.30 (d, 1H), 6.03–5.99 (m, 2H), 5.11 (broad, 1H), 3.46 (q, 2H), 3.10 (d, 3H), 1.69–1.42 (m, 4H), 0.97 (t, 3H); ¹⁹F NMR (CDCl₃) δ −113.39; MS m/z 391 (M+1).

EXAMPLE 50

4-[7-Chloro-2-(4-fluorophenyl)pyrazolo[1,5-α]pyridin-3-yl]-N-cyclopentyl-6-[(dimethylamino)methyl]-2-pyrimidinamine

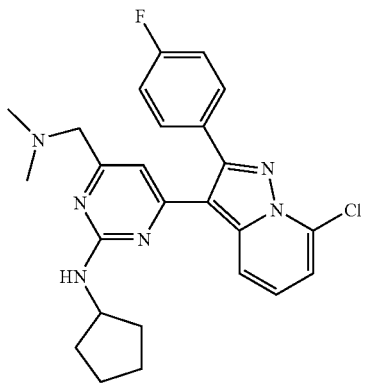

a) 4-[7-Chloro-2-(4-fluorophenyl)pyrazolo[1,5-α]pyridin-3-yl]-N-cyclopentyl-6-(iodomethyl)-2-pyrimidinamine

[6-[7-Chloro-2-(4-fluorophenyl)pyrazolo[1,5-α]pyridin-3-yl]-2-(cyclopentylamino)-4-pyrimidinyl]methanol (215 mg, 0.49 mmol) was dissolved in a mixture of benzene (4 mL) and ether (8 mL). Imidazole (134 mg, 2.0 mmol) and triphenylphosphine (191 mg, 0.73 mmol) were added sequentially. A solution of iodine (179 mg, 0.71 mmol) in ether (5 mL) was added dropwise to the reaction mixture over 10 minutes. The resultant solution was stirred for an additional 20 minutes then diluted with 10 mL of ether. The mixture was filtered to remove solids. Concentration followed by flash chromatography (4:1 hexanes:ethyl acetate) provided 4-[7-chloro-2-(4-fluorophenyl)pyrazolo[1,5-α]pyridin-3-yl]-N-cyclopentyl-6-(iodomethyl)-2-pyrimidinamine (160 mg, 60%) as a solid. Rƒ 0.47 (4:1 hexanes:ethyl acetate); ¹H NMR (CDCl₃) δ 8.38 (d, 1H), 7.67 (m, 2H), 7.28 (m, 1H), 7.18 (t, 2H), 7.03 (d, 1H), 6.38 (s, 1H), 5.19 (d, 1H), 4.35 (m, 1H), 4.02 (s, 2H), 2.10 (m, 2H), 2.67 (m, 6H).

b) 4-[7-chloro-2-(4-fluorophenyl)pyrazolo[1,5-α]pyridin-3-yl]-N-cyclopentyl-6-[(dimethylamino)methyl]-2-pyrimidinamine To a solution of 4-[7-chloro-2-(4-fluorophenyl)pyrazolo[1,5-α]pyridin-3-yl]-N-cyclopentyl-6-(iodomethyl)-2-pyrimidinamine (160 mg, 0.29 mmol) in tetrahydrofuran (2 mL) was added dimethylamine (730 μL, 2 M in THF, 1.5 mmol) and the reaction mixture was allowed to stir at room temperature for 16 hours. The reaction mixture was diluted with ethyl acetate and washed with saturated aqueous sodium bicarbonate solution, water, and brine. The organic layer was dried over magnesium sulfate. Filtration and concentration provided the crude amine (120 mg, 88%). A portion of the crude amine (26 mg) was purified by flash chromatography (38:2 dichloromethane:methanol to 37:3 dichloromethane:methanol) to provide 4-[7-chloro-2-(4-fluorophenyl)pyrazolo[1,5-α]pyridin-3-yl]-N-cyclopentyl-6-[(dimethylamino)methyl]-2-pyrimidinamine (15 mg). Rƒ 0.32 (37:3 dichloromethane:methanol); ¹H NMR (CDCl₃) δ 8.37 (d, 1H), 7.66 (m, 2H), 7.26 (m, 1H), 7.11 (t, 2H), 7.03 (d, 1H), 6.39 (s, 1H), 5.18 (d, 1H), 4.35 (m, 1H), 3.23 (s, 2H), 2.22 (s, 6H), 2.07 (m, 2H), 1.80–1.45 (m, 6H); MS m/z 465 (M+1); mp 68–75° C.

EXAMPLE 51

N-Cyclopentyl-3-{2-(cyclopentylamino)-6-[(dimethylamino)methyl]-4-pyrimidinyl}-2-(4-fluorophenyl)pyrazolo[1,5-α]pyridin-7-amine

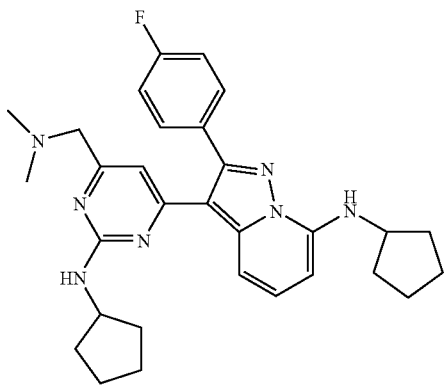

A solution of 4-[7-chloro-2-(4-fluorophenyl)pyrazolo[1,5-α]pyridin-3-yl]-N-cyclopentyl-6-[(dimethylamino)methyl]-2-pyrimidinamine (60 mg, 0.13 mmol) in cyclopentylamine (2 mL) was heated in a sealed tube at 95° C. for 16 hours followed by heating at 100° C. for 72 hours. After cooling to room temperature, the reaction mixture was diluted with ethyl acetate and washed with a saturated aqueous sodium bicarbonate solution. The organic layer was concentrated and chromatographed (37:3 dichloromethane:methanol) to provide N-cyclopentyl-3-{2-(cyclopentylamino)-6-[(dimethylamino)methyl]-4-pyrimidinyl}-2-(4-fluorophenyl)pyrazolo[1,5-α]pyridin-7-amine (10 mg, 15%). $^1$H NMR (CDCl$_3$) δ 7.70 (d, 1H), 7.65 (m, 2H), 7.31 (t, 1H), 7.12 (t, 2H), 6.37 (s, 1H), 6.05–5.95 (m, 2H), 5.13 (d, 1H), 4.35 (m, 1H), 4.01 (m, 1H), 3.20 (s, 2H), 2.20 (s, 6H), 2.15 (m, 2H), 2.05 (m, 2H), 1.90–1.50 (m, 12H); MS m/z 514 (M+1).

EXAMPLE 52

4-[7-Chloro-2-(4-fluorophenyl)pyrazolo[1,5-α]pyridin-3-yl]-N-cyclopentyl-5-methyl-2-pyrimidinamine

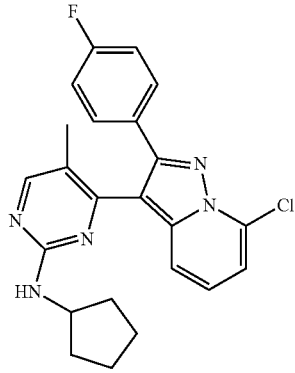

a) 1-[7-Chloro-2-(4-fluorophenyl)pyrazolo[1,5-α]pyridin-3-yl]-2-methyl-2-propen-1-ol In a similar manner as described in Example 7, from 7-chloro-2-(4-fluorophenyl)pyrazolo[1,5-α]pyridine-3-carbaldehyde (510 mg, 1.9 mmol) and isopropenyl magnesium bromide was obtained 1-[7-chloro-2-(4-fluorophenyl)-pyrazolo[1,5-α]pyridin-3-yl]-2-methyl-2-propen-1-ol (530 mg, 90%) as an off-white solid. R$_f$ 0.26 (4:1 hexanes:ethyl acetate); $^1$H NMR (CDCl$_3$) δ 7.81–7.70 (m, 3H), 7.21–7.08 (m, 3H), 6.95 (d, 1H), 5.41 (s, 1H), 5.30 (s, 1H), 5.08 (s, 1H), 1.62 (s, 3H); MS m/z 317 (M+1).

b) 1-[7Chloro-2-(4-fluorophenyl)pyrazolo[1,5-α]pyridin-3-yl]-2-methyl-2-propen-1-one In a similar manner as described in Example 7, from 1-[7-chloro-2-(4-fluorophenyl)pyrazolo[1,5-α]pyridin-3-yl]-2-methyl-2-propen-1-ol (530 mg, 1.7 mmol) was formed 1-[7-chloro-2-(4-fluorophenyl)pyrazolo[1,5-α]pyridin-3-yl]-2-methyl-2-propen-1-one (390 mg, 74%) as a white solid. R$_f$ 0.29 (4:1 hexanes:ethyl acetate); $^1$H NMR (CDCl$_3$) δ 7.96 (d, 1H), 7.59 (m, 2H), 7.34 (t, 1H), 7.18–7.07 (m, 3H), 5.48 (s, 1H), 5.40 (s, 1H), 1.98 (s, 3H).

c) 4-[7-Chloro-2-(4-fluorophenyl)pyrazolo[1,5-α]pyridin-3-yl]-N-cyclopentyl-5-methyl-2-pyrimidinamine To a suspension of N-cyclopentylguanidine hydrochloride (68 mg, 0.42 mmol) in ethanol (1 mL) was added sodium ethoxide (138 μL, 3 M in ethanol, 0.41 mmol). A solution of 1-[7-chloro-2-(4-fluorophenyl)pyrazolo[1,5-α]pyridin-3-yl]-2-methyl-2-propen-1-one in ethanol (1 mL) was added and the reaction mixture was allowed to stir at room temperature for 16 hours. An additional aliquot of N-cyclopentylguanidine hydrochloride (68 mg, 0.42 mmol) and sodium ethoxide (138 μL, 3 M in ethanol, 0.41 mmol) in ethanol (1 ml) was added to reaction mixture and allowed to stir an additional 24 hours. Palladium on carbon (10%, 30 mg) was added to reaction mixture and allowed to stir at room temperature for 30 minutes under an atmosphere of air, at which point additional palladium on carbon (10%, 100 mg) was added. The reaction mixture was allowed to stir at room temperature 16 hours. The suspension was diluted with ethyl acetate and filtered through Celite. Concentration followed by flash chromatography (4:1 hexanes:ethyl acetate) provided 4-[7-chloro-2-(4-fluorophenyl)pyrazolo[1,5-α]pyridin-3-yl]-N-cyclopentyl-5-methyl-2-pyrimidinamine (57 mg, 43%) as a clear oil. R$_f$ 0.24 (4:1 hexanes:ethyl acetate); $^1$H NMR (CDCl$_3$) δ 8.14 (s, 1H), 7.64 (m, 2H), 7.57 (d, 1H), 7.17 (m, 1H), 7.08 (t, 2H), 7.00 (d, 1H), 5.09 (d, 1H), 4.26 (m, 1H), 2.03 (m, 2H), 1.82–1.45 (m, 9H); MS m/z 422 (M+1). To a solution of the product in ether was added 1 M hydrochloride in ether. The precipitated solid was isolated to give the corresponding hydrochloride salt.

EXAMPLE 53

N-Cyclopentyl-3-[2-(cyclopentylamino)-5-methyl-4-pyrimidinyl]-2-(4-fluorophenyl)pyrazolo[1,5-α]pyridin-7-amine

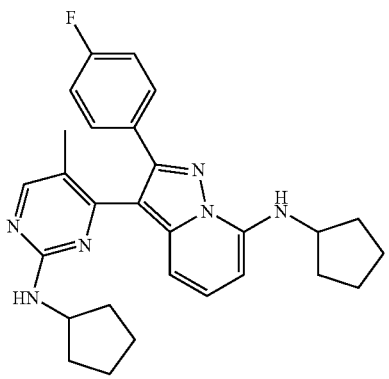

In a similar manner as described in Example 7, from 4-[7-chloro-2-(4-fluorophenyl)pyrazolo[1,5-α]pyridin-3-yl]-N-cyclopentyl-5-methyl-2-pyrimidinamine (52 mg, 0.12 mmol) and cyclopentylamine was formed N-cyclopentyl-3-[2-(cyclopentylamino)-5-methyl-4-pyrimidinyl]-2-(4-fluorophenyl)pyrazolo[1,5-α]pyridin-7-amine (47 mg, 90%) as a yellow oil. $R_f$ 0.15 (4:1 hexanes:ethyl acetate); $^1$H NMR (DMSO-$d_6$) δ 8.51 (broad, 1H), 8.27 (s, 1H), 7.65 (m, 2H), 7.41 (t, 1H), 7.28 (t, 2H), 6.97 (d, 1H), 6.74 (br, 1H), 6.25 (d, 1H), 4.14 (br, 1H), 4.05 (br, 1H), 2.09 (m, 2H), 1.96–1.42 (m, 17H); MS m/z 471 (M+1). To a solution of the product in ether was added 1 M hydrochloride in ether. The precipitated solid was isolated to give the corresponding hydrochloride salt.

EXAMPLE 54

N-Allyl-3-[2-(butylamino)-4-pyrimidinyl]-2-(4-fluorophenyl)pyrazolo[1,5-α]pyridin-7-amine

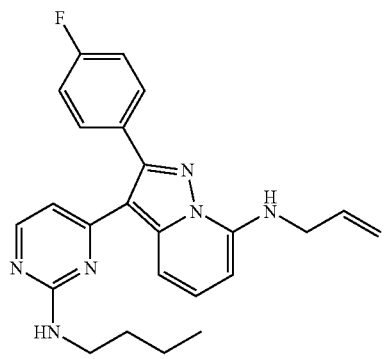

A solution of N-butyl-4-[7-chloro-2-(4-fluorophenyl)pyrazolo[1,5-α]pyridin-3-yl]-2-pyrimidinamine (0.15 g, 0.38 mmol) in allylamine (5 mL, 67 mmol) was heated at 85° C. in a sealed tube for 88 hours. After cooling and concentrating the reaction mixture, flash chromatography (4:1 hexanes-ethyl acetate) afforded N-allyl-3-[2-(butylamino)-4-pyrimidinyl]-2-(4-fluorophenyl)pyrazolo[1,5-α]pyridin-7-amine (0.14 g, 88%) as a pale yellow foam. $^1$H NMR (CDCl$_3$): δ 7.89 (broad, 1H), 7.78 (d, 1H), 7.62 (m, 2H), 7.36 (t, 1H), 7.16 (t, 2H), 6.31–6.26 (m, 2H), 6.09–5.92 (m, 2H), 5.39–5.24 (m, 2H), 4.06 (t, 2H), 3.50 (q, 2H), 1.72–1.41 (m, 4H), 0.98 (t, 3H); $^{19}$F NMR (CDCl$_3$) δ −113.16; MS m/z 417 (M+1); Anal. Calcd for C$_{24}$H$_{25}$FN$_6$: C, 69.21; H, 6.05; N, 20.18. Found: C, 69.27; H, 6.07; N, 20.03.

EXAMPLE 55

3-[2-(Butylamino)-4-pyrimidinyl]-2-(4-fluorophenyl)-N-propylpyrazolo[1,5-α]pyridin-7-amine

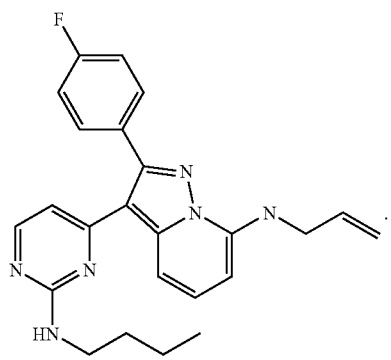

To a solution of N-allyl-3-[2-(butylamino)-4-pyrimidinyl]-2-(4-fluorophenyl)pyrazolo[1,5-α]pyridin-7-amine (80 mg, 0.19 mmol) in ethanol (5 mL) was added palladium on carbon (10%, 8 mg). The mixture was stirred overnight at room temperature under a balloon filled with hydrogen. The reaction was filtered through a pad of Celite and concentrated to give 3-[2-(butylamino)-4-pyrimidinyl]-2-(4-fluorophenyl)-N-propylpyrazolo[1,5-α]pyridin-7-amine (79 mg, 99%) as a gold foam. $^1$H NMR (CDCl$_3$): δ 8.03 (d, 1H), 7.74 (d, 1H), 7.69 (m, 2H), 7.33 (t, 1H), 7.15 (t, 2H), 6.30 (d, 1H), 6.08–6.01 (m, 2H), 5.08 (broad, 1H), 3.47 (q, 2H), 3.37 (q, 2H), 1.87–1.41 (m, 6H), 1.08 (t, 3H), 0.99 (t, 3H); $^{19}$F NMR (CDCl$_3$) δ −113.44; MS m/z 419 (M+1).

EXAMPLE 56

7-Chloro-2-(4-fluorophenyl)-3-pyridin-4-ylpyrazolo[1,5-α]pyridine

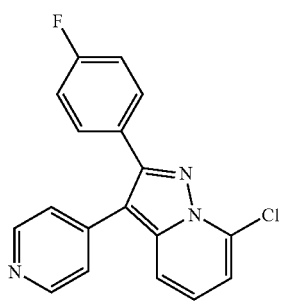

a) 1-(4-Fluorophenyl)-2-trimethylsilylacetylene

4-Fluoroiodobenzene (112 mL, 0.97 mol) and triethylamine (176 mL, 1.26 mol) are dissolved in dry tetrahydrofuran (1.2 L) and nitrogen gas was bubbled through the solution for about 20 min. Copper (I) iodide (1.08 g, 5.7 mmol) and bis(triphenyphosphine)palladium dichloride (2.15 g, 3 mmol) are added and then trimethylsilylacetylene (178 mL, 1.3 mol) was added dropwise over about 40 min with the temperature being maintained at about 23° C. A large amount of precipitate forms which necessitates mechanical stirring. Following complete addition of the trimethylsilylacetylene the mixture was allowed to stir at room temperature for about 18 hours. The mixture was filtered and the solid washed with cyclohexane. The combined filtrates are concentrated under reduce pressure to give a brown oil. Application of this oil to a pad of silica gel followed by elution with cyclohexane gave a yellow solution. Removal of the solvent gave the title compound as a yellow oil; 182.8 g (95%).

b) Methyl 3-(4-fluorophenyl)propiolate

A solution of 1-(4-fluorophenyl)-2-trimethylsilylacetylene (64 g, 0.33 mol) in dry diethyl ether (400 mL) was cooled to 0° C. under a nitrogen atmosphere. To this solution was added, dropwise over 45 minutes, a solution of tetrabutylammonium fluoride (1 M in tetrahydrofuran, 330 mL, 0.33 mol) via a dropping funnel maintaining the internal temperature below 2° C. The mixture was allowed to warm to room temperature over about 1 hour. Diethyl ether (300 mL) was added to the mixture and the organic solution was washed with water, saturated brine and then dried over anhydrous magnesium sulfate. The magnesium sulfate was removed by filtration and the filtrate was cooled to about −78° C. n-Butyl lithium (1.6M in hexanes, 450 mL, 0.72 mol) was added dropwise via a dropping funnel over about 1 h while the temperature was maintained below −66° C. After complete addition the mixture was stirred at −78° C. for about 1 h and then a precooled solution of methyl chloroformate (110 mL, 1.4 mol) in dry diethyl ether (200 mL) was added in a continuous stream as fast as possible. The mixture was allowed to cool to −78° C. and then allowed to warm to room temperature over 1.5 h. The organic reaction mixture was washed with water and saturated brine and then dried over anhydrous magnesium sulfate. The solvents are remove under reduced pressure and the residue dried under reduced pressure to give the title compound as a brown solid, 36.5 g (61%). $^1$H NMR (CDCl$_3$) δ 7.58 (dd, 2H, J=9, 5.4 Hz), 7.07 (t, 2H, J=8.5 Hz), 3.84 (s, 3H). MS (+ve ion electrospray) 178 (30), (M$^+$).

c) Methyl 2-(4-fluorophenyl)-pyrazolo[1,5-α]pyridine-3-carboxylate

A stirred solution of methyl 3-(4-fluorophenyl)propiolate (8.02 g, 45 mmol) and 1-aminopyridinium iodide (10 g, 45 mmol) in dry acetonitrile (150 mL) was cooled to about 0° C. A solution of 1,8-diazabicycloundec-7-ene (13.7 g, 90 mmol) in dry acetonitrile (50 mL) was added dropwise over 1 hour. The mixture was allowed to stir at room temperature for about 18 h. The reaction mixture was cooled in an ice bath for about 30 min and the precipitate was collected by filtration and washed with cold acetonitrile (10 mL). The solid was dried under reduced pressure to give the title compound as a white solid, 8.48 g (70%). $^1$H NMR (CDCl$_3$) δ 8.50 (d, 1H, J=8.4 Hz), 8.18 (d, 1H, J=8.8 Hz), 7.78 (m, 2H), 7.42 (t, 1H, J=8.4 Hz), 7.13 (t, 2H, J=8.8 Hz), 6.97 (td, 1H, J=6.8, 1 Hz). ). MS (+ve ion electrospray) 271 (100), (MH$^+$).

d) 2-(-Fluorophenyl)-pyrazolo[1,5-α]pyridine-3-carboxylic acid

A solution of methyl 2-(4-fluorophenyl)-pyrazol[1,5-α]pyridine-3-carboxylate (5.0 g, 18.5 mmol) in 2N aqueous sodium hydroxide (50 ml) and methanol (30 mL) was heated at reflux for about 3 h. The mixture was filtered and the filtrate was washed with diethyl ether (20 mL) and then concentrated under reduced pressure to about half the original volume. Concentrated hydrochloric acid was added to adjust the pH to about 2 and the resulting solid was collected by filtration and washed with water and dried under vacuum to give the title compound as a white solid, 4.8 g (ca. 100%). $^1$H NMR (d$_6$ DMSO) δ 12.43 (br s, 1h), 8.84 (d, 1H, J=6.9 Hz), 8.14 (d, 1H, J=9 Hz), 7.82 (m, 2H), 7.57 (t, 1H, J=8.1 Hz), 7.28 (t, 2H, J=9 Hz), 7.15 (td, 1H, J=6.9, 1.2 Hz). MS (+ve ion electrospray) 257 (100), (MH$^+$).

e) 2-(4-Fluorophenyl)-3-bromopyrazolo[1,5-α]pyridine

To a solution of 2-(4-fluorophenyl)-pyrazolo[1,5-α]pyridine-3-carboxylic acid (0.96 g, 3.75 mmol) in dry N,N-dimethylformamide (10 mL) was added sodium bicarbonate (0.95 g, 11.3 mmol) followed by N-bromosuccinimide (0.667 g, 3.75 mmol) and the mixture was stirred at room temperature under a nitrogen atmosphere for about 90 min. The mixture was poured into water (300 mL) and the resulting solid was collected by filtration and washed with water. The solid was dissolved in 10:1 chloroform-methanol (10 mL) and filtered through a pad (0.5 cm) of silica gel using 10:1 chloroform:methanol as eluent. The filtrate was evaporated to leave the title compound as a tan solid, 0.87 g (80%). $^1$H NMR (d$_6$ DMSO) δ 8.7 (d, 1H, J=6.9 Hz), 8.02 (dd, 2H, J=8.7, 5.7 Hz), 7.61 (d, 1H, J=8.4 Hz), 7.40 (t, 1H, J=6 Hz), 7.38 (t, 2H, J=9 Hz), 7.04 (t, 1H, J=6.9 Hz). MS (+ve ion electrospray) 293 (100), (MH$^+$).

f) 2-(4-Fluorophenyl)-3-(4-pyridyl)-pyrazolo[1,5-α]pyridine

To a solution of 2-(4-fluorophenyl)-3-bromopyrazolo[1,5-α]pyridine (0.2 g, 0.68 mmol) and 4-(tributylstannyl)pyridine (0.38 g, 1 mmol) in dry toluene (10 mL) was added tetrakis(triphenylphosphine)palladium (0) (0.03 g, 0.03 mmol) and the mixture was heated at reflux temperature under a nitrogen atmosphere for about 48 hours. The mixture was cooled to room temperature and diluted with diethyl ether (40 mL). The mixture was poured into a 10% aqueous solution of potassium fluoride (20 mL) and the mixture was stirred for 1 hour. The biphasic mixture was filtered through a pad of diatomaceous earth and the organic phase was separated. The aqueous phase was extracted with diethyl ether (10 mL) and the combined organic phases are washed with brine, dried over anhydrous magnesium sulfate, filtered and the solvent evaporated under reduced pressure. The residue was purified using silica gel chromatography with 20% ethyl acetate in hexanes, followed by 50% ethyl acetate in hexanes, as eluent to give the title compound as an off white solid, 0.16 g (80%). $^1$H NMR (CDCl$_3$) δ 8.58 (br s, 2H), 8.50 (d, 1H, J=7.2 Hz), 7.63 (d, 1H, 9 Hz), 7.52 (m, 2H), 7.27–7.20 (m, 3H), 7.06 (t, 2H, 8.7 Hz), 6.86 dt, 1H, J=7, 1 Hz). MS (+ve ion electrospray) 290 (100), (MH$^+$).

g) 7-Chloro-2-(4-fluorophenyl)-3-(4-pyridinyl)pyrazolo[1,5-α]pyridine

To a stirred solution of 2-(4-fluorophenyl)-3-(4-pyridinyl)pyrazolo[1,5-α]pyridine (100 mg, 0.346 mmol) in 4 ml of tetrahydrofuran at −78° C. under N$_2$ was added 2.5 M n-butyllithium in hexanes (22 μl, 2 eq). The mixture was stirred at −78° C. for 30 min and N-chlorosuccinimide (2.2 eqv) was then added. The mixture was allowed to warm to room temperature after 30 min and was stirred at room temperature for 1 hr. The mixture was diluted with ether and washed with 1N hydrochloric acid solution. The aqueous layer was basified with 1N sodium hydroxide solution and extracted thoroughly with ether. The combined organic layers were dried on anhydrous magnesium sulfate, filtered and evaporated. Purification by chromatography yielded 7-chloro-2-(4-fluorophenyl)-3-(4-pyridinyl)pyrazolo[1,5-α] pyridine (71%).

When the electrophile is N-chlorosuccinimide in 1 ml of tetrahydrofuran, 7-chloro-2-(4-fluorophenyl)-3-(4-pyridinyl)pyrazolo[1,5-α]pyridine was isolated as yellow solid in 72% yield. When the electrophile is p-toluenesulfonyl chloride in 1 ml of tetrahydrofuran, 7-chloro-2-(4-fluorophenyl)-3-(4-pyridinyl)pyrazolo[1,5-α]pyridine was isolated as yellow solid in 79% yield. $^1$H NMR (CDCl$_3$): δ 8.65 (d, 2H, J=5.8 Hz), 7.55–7.69 (m, 3H), 7.30 (d, 2H, J=5.8 Hz), 7.11–7.21 (m, 1H), 7.04–7.13 (m, 3H); MS (ES+ve): 326 (25, M+3), 323 (50, M$^+$), 290 (100).

EXAMPLE 57

N-[2-(4-Fluorophenyl)-3-(4-pyridinyl)pyrazolo[1,5-α]pyridin-7-yl]-N-[2-(1-methyl-2-pyrrolidinyl)ethyl]amine

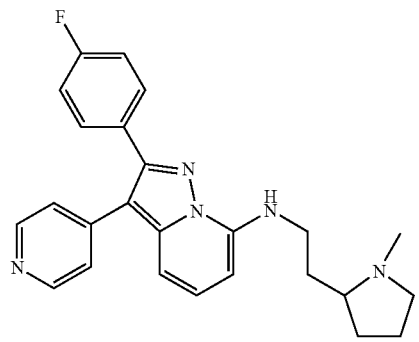

To a stirred solution of 7-chloro-2-(4-fluorophenyl)-3-(4-pyridinyl)pyrazolo[1,5-α]pyridine (50 mg, 0.154 mmol) in 1 mL of isopropanol was added excess of 2-(1-methylpyrrolidin-2-yl)ethanamine (1 mL). The mixture was heated to reflux at 85° C. overnight. The mixture was evaporated to dryness and purified by preparative thin layer chromatography to give N-[2-(4-fluorophenyl)-3-(4-pyridinyl)pyrazolo[1,5-α]pyridin-7-yl]-N-[2-(1-methyl-2-pyrrolidinyl)ethyl]amine as peach solid in 17% yield (28.3% yield based on recovered starting material). $^1$H NMR (CDCl$_3$): δ 8.58 (dd, 2H, J=1.4, 4.6 Hz), 7.59–7.62 (m, 2H), 7.25–7.32 (m, 3H), 7.04–7.14 (m, 3H), 6.83 (t, 1H, J=5.3 Hz), 5.98 (d, 1H, J=7.4 Hz), 3.40–3.55 (m, 2H), 3.13–3.19 (m, 1H), 2.43 (s, 3H), 2.36–2.43 (m, 1H), 2.20–2.29 (m, 1H), 1.66–2.20 (m, 6H); MS (ES+ve): 418 (10, M+3), 417 (20, M+2), 416 (60, M+1), 112 (100).

EXAMPLE 58

2-(4-Fluorophenyl)-N-methyl-3-(4-pyridinyl)pyrazolo[1,5-α]pyridin-7-amine

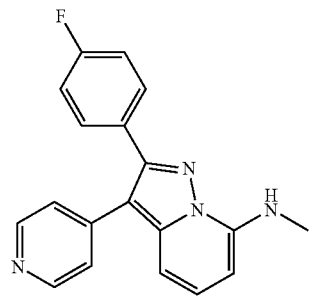

7-Chloro-2-(4-fluorophenyl)-3-(4-pyridinyl)pyrazolo[1,5-α]pyridine (25 mg, 0.077 mmol) and excess of methylamine in alcohol (1 mL) in sealed tube was heated at 120° C. for overnight. The mixture was evaporated to dryness and purified by preparative thin layer chromatography to give 2-(4-fluorophenyl)-N-methyl-3-(4-pyridinyl)pyrazolo[1,5-α]pyridin-7-amine a peach solid in 77.3% yield. $^1$H NMR (CDCl$_3$): δ 8.59 (d, 2H, J=5.4 Hz), 7.58–7.62 (m, 2H), 7.28–7.30 (m, 3H), 7.07–7.14 (m, 3H), 6.11 (bs, 1H), 6.00 (d, 1H, J=7.4 Hz), 3.16 (d, 3H, J=5.0 Hz); MS (ES+ve): 320 (18, M+2), 319 (20, M+1), 318 (100, M$^+$).

EXAMPLE 59

N,N-Diethyl-2-(4-fluorophenyl)-3-(4-pyridinyl)pyrazolo[1,5-α]pyridin-7-amine

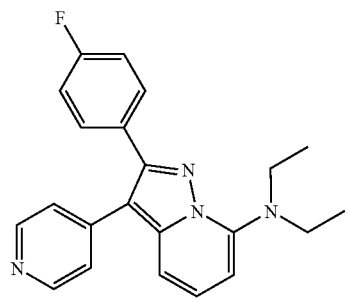

7-Chloro-2-(4-fluorophenyl)-3-(4-pyridinyl)pyrazolo[1,5-α]pyridine and excess of diethylamine in alcohol (1 mL) in sealed tube was heated at 120° C. for overnight. The mixture was evaporated to dryness and purified by preparative thin layer chromatography to give N,N-diethyl-2-(4-fluorophenyl)-3-(4-pyridinyl)pyrazolo[1,5-α]pyridin-7-amine. $^1$H NMR (CDCl$_3$): δ 8.61 (d, 2H, J=6.0 Hz), 7.61–7.66 (m, 2H), 7.22–7.34 (m, 4H), 7.09 (t, 2H, J=8.7 Hz), 6.32 (d, 1H, J=6.1 Hz), 3.64 (q, 4H, J=7.0 Hz), 1.26 (t, 6H, J=7 Hz). MS (ES+ve): 362 (25, M+2), 361 (100, M+1).

EXAMPLE 60

2-(4-Fluorophenyl)-7-iodo-3-pyridin-4-ylpyrazolo[1,5-α]pyridine

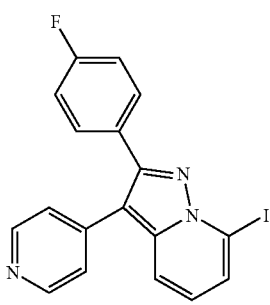

To a stirred solution of 2-(4-fluorophenyl)-3-(4-pyridyl)-pyrazolo[1,5-α]pyridine (100 mg, 0.346 mmol) in 4 mL of tetrahydrofuran at −78° C. under $N_2$ was added 2.5 M n-butyllithium in hexanes (2 eq.). The mixture was stirred at −78° C. for 30 min and N-iodosuccinimide (2.2 eq.) was then added. The mixture was allowed to warm to room temperature after 30 min and was stirred at room temperature for 1 hour. The mixture was diluted with ether and washed with 1N hydrochloric acid solution. The aqueous layer was basified with 1 N sodium hydroxide solution and extracted thoroughly with ether. The combined organic layers were dried on anhydrous magnesium sulfate, filtered and evaporated. Purification by chromatography yielded 2-(4-fluorophenyl)-7-iodo-3-pyridin-4-ylpyrazolo[1,5-α]pyridine as a yellow solid. $^1$H NMR (CDCl$_3$): δ 8.54 (d, 2H, J=5.8 Hz), 7.50–7.57 (m, 3H), 7.37 (d, 1H, J=7.1 Hz), 7.20 (d, 2H, J=5.8 Hz), 7.00 (t, 2H, J=8.6 Hz), 6.90 (t, 1H, J=7.8 Hz); MS m/z 416 (M+1).

EXAMPLE 61

7-Bromo-2-(4-fluorophenyl)-3-pyridin-4-ylpyrazolo[1,5-α]pyridine

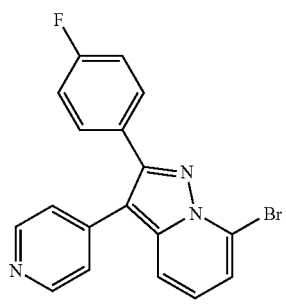

To a stirred solution of of 2-(4-fluorophenyl)-3-(4-pyridyl)-pyrazolo[1,5-α]pyridine (100 mg, 0.346 mmol) in 4 ml of tetrahydrofuran at −78° C. under $N_2$ was added 2.5 M n-butyllithium in hexanes (2 eq.). The mixture was stirred at −78° C. for 30 min and N-bromosuccinimide (2.2 eq.) was then added. The mixture was allowed to warm to room temperature after 30 min and was stirred at room temperature for 1 hr. The mixture was diluted with ether and washed with 1N hydrochloric acid solution. The aqueous layer was basified with 1N sodium hydroxide solution and extracted thoroughly with ether. The combined organic layers were dried on anhydrous magnesium sulfate, filtered and evaporated. Purification by chromatography yielded 7-bromo-2-(4-fluorophenyl)-3-pyridin-4-ylpyrazolo[1,5-α]pyridine as a yellow solid. $^1$H NMR (CDCl$_3$): δ 8.65 (d, 2H, J=5.0 Hz), 7.56–7.68 (m, 3H), 7.31 (d, 2H, J=5.0 Hz), 7.11–7.30 (m, 4H; MS m/z 368 (M+1).

EXAMPLE 62

N-Butyl-2-(4-fluorophenyl)-3-pyridin-4-ylpyrazolo[1,5-α]pyridin-7-amine

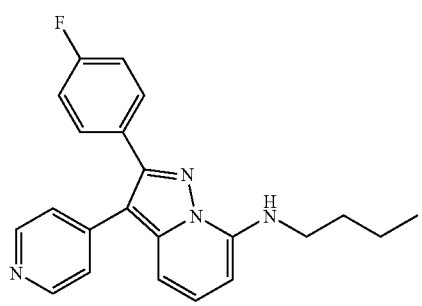

A mixture of of 7-chloro-2-(4-fluorophenyl)-3-(4-pyridinyl)pyrazolo[1,5-α]pyridine in toluene (2 mL) and excess of butylamine (1 mL) in sealed tube was heated at 110° C. for overnight. The mixture was evaporated to dryness and purified by preparative thin layer chromatography to give N-butyl-2-(4-fluorophenyl)-3-pyridin-4-ylpyrazolo[1,5-α]pyridin-7-amine. $^1$H NMR (CDCl$_3$): δ 8.53 (d, 2H, J=5.1 Hz), 7.54–7.57 (m, 2H), 7.20–7.24 (m, 3H), 7.06 (t, 2H, J=8.6 Hz), 7.02–7.00 (m, 1H), 6.04 (bs, 1H), 5.95 (d, 1H, J=7.7 Hz), 3.39 (q, 2H, J=6.4 Hz), 1.74–1.78 (m, 2H), 1.47–1.56 (m, 2H), 0.99 (t, 3H, J=7.4 Hz); MS m/z 361 (M+1).

EXAMPLE 63

2-(4-Fluorophenyl)-7-(1H-imidazol-1-yl)-3-pyridin-4-ylpyrazolo[1,5-α]pyridine

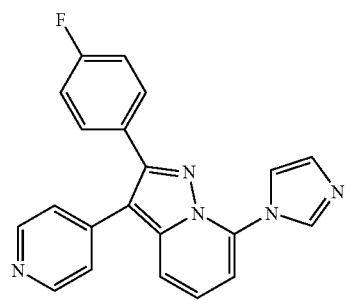

A mixture of 7-chloro-2-(4-fluorophenyl)-3-(4-pyridinyl) pyrazolo[1,5-α]pyridine (100 mg) and imidazole (5 eq.) in dimethylsulfoxide (2 mL) in sealed tube was heated at 120° C. overnight. The mixture was evaporated to dryness and purified by preparative thin layer chromatography to give 2-(4-fluorophenyl)-7-(1H-imidazol-1-yl)-3-pyridin-4- ylpyrazolo[1,5-α]pyridine. ¹H NMR (CDCl₃): δ 8.65 (d, 2H, J=5,6 Hz), 7.96 (s, 1H), 7.60 (d, 1H, J=9.5 Hz), 7.44–7.47 (m, 2H), 7.34–7.38 (m, 4H), 7.28 (d, 2H, J=5.7 Hz), 7.02 (m, 2H); MS m/z 356 (M+1).

EXAMPLE 64

2-(4-Fluorophenyl)-3,7-bis(2-fluoropyridin-4-yl)pyrazolo[1,5-α]pyridine

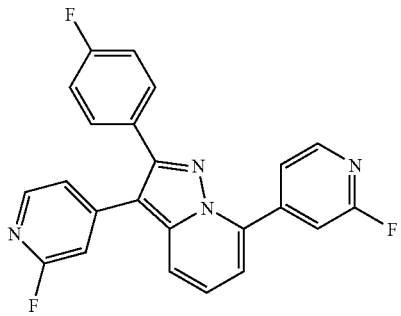

In a similar manner to that in Example 28, from 3-bromo-7-chloro-2-(4-fluorophenyl)pyrazolo[1,5-α]pyridine (305 mg, 0.94 mmol) and 2-fluoropyridin-4-ylboronic acid (182 mg, 1.30 mmol) after heating to 100° C. for 1.5 hours was formed 2-(4-fluorophenyl)-3,7-bis(2-fluoropyridin-4-yl)pyrazolo[1,5-α]pyridine (90 mg, 24%). ¹H NMR (CDCl₃): δ 8.47 (d, 1H), 8.29 (d 1H), 7.89 (br d, 1H), 7.78 (d, 1H), 7.72 (s, 1H), 7.58 (dd, 2H), 7.44 (dd, 1H), 7.20 (br d, 1H), 7.15 (d, 1H), 7.13 (t, 2H), 7.05 (s, 1H); MS m/z 403 (M+1).

EXAMPLE 65

N-{4-[3-{2-[(3-Aminopropyl)amino]pyridin-4-yl}-2-(4-fluorophenyl)pyrazolo[1,5-α]pyridin-7-yl]pyridin-2-yl}propane-1,3-diamine

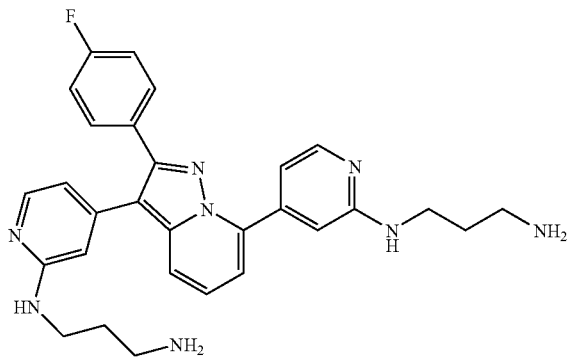

A solution of 2-(4-fluorophenyl)-3,7-bis(2-fluoropyridin-4-yl)pyrazolo[1,5-α]pyridine (34 mg, 0.08 mmol) in 1,3-diaminopropane (1 mL) was heated at 150° C. for 0.25 hours. Upon cooling to room temperature, the mixture was concentrated in vacuo and the residue was triturated with hot ethyl acetate. The resulting solids were collected on filter, washed with ethyl ether and dried to provide N-{4-[3-{2-[(3-aminopropyl)amino]pyridin-4-yl}-2-(4-fluorophenyl)pyrazolo[1,5-α]pyridin-7-yl]pyridin-2-yl}propane-1,3-diamine as a light yellow powder (19 mg, 46%). ¹H NMR (CD₃OD): δ 8.18 (d, 1H), 8.03 (d, 1H), 7.78 (d, 1H), 7.65 (dd, 2H), 7.45 (dd, 1H), 7.30 (s, 1H), 7.1–7.2 (m, 4H), 6.60 (s, 1H), 6.59 (d, 1H), 3.55 (t, 2H), 3.47 (t, 2H), 3.0 (q, 4H), 1.88–2.04 (m, 4H); MS m/z 511 (M+1).

EXAMPLE 66

4-[7-Chloro-2-(4-fluorophenyl)pyrazolo[1,5-α]pyridin-3-yl]-N-propylpyridin-2-amine

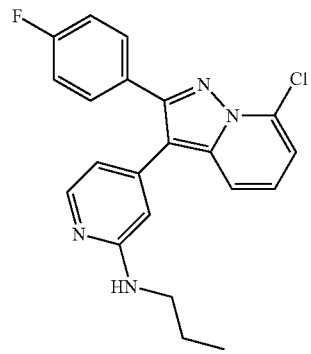

Prepared in a similar manner as Example 56. ¹H NMR (d₆-acetone): δ 8.04 (d, 1H), 7.68–7.76 (m, 3H), 7.35 (dd, 1H), 7.16–7.24 (m, 3H), 6.46–6.50(m, 2H), 3.28 (t, 2H), 1.60 (sextet, 2H), 0.85 (t, 3H); MS m/z 381 (M+1).

EXAMPLE 67

N-Butyl-4-[7-chloro-2-(4-fluorophenyl)pyrazolo[1,5-α]pyridin-3-yl]pyridin-2-amine

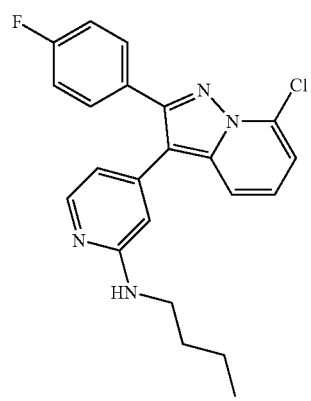

Prepared in a similar manner as Example 56. ¹H NMR (d⁶-acetone): δ 8.04 (d, 1H), 7.68–7.76 (m, 3H), 7.35 (dd, 1H), 7.17–7.25 (m, 3H), 6.46–6.50(m, 2H), 3.32 (t, 2H), 1.57 (m, 2H), 1.40 (m, 2H), 0.82 (t, 3H); MS m/z 395 (M+1).

EXAMPLE 68

N-Butyl-2-(4-fluorophenyl)-3-[2-(2,2,2-trifluoroethoxy)pyrimidin-4-yl]pyrazolo[1,5-α]pyridin-7-amine

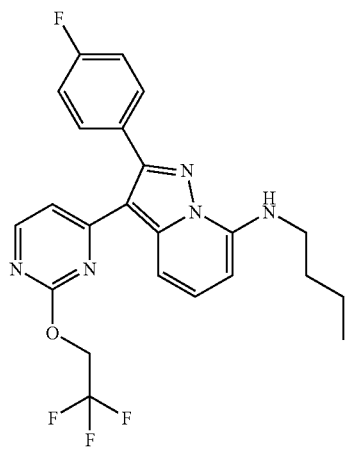

In a similar manner as described in Example 38, from N-butyl-2-(4-fluorophenyl)-3-[2-(methylsulfinyl)-4-pyrimidinyl]pyrazolo[1,5-α]pyridin-7-amine (50 mg, 0.12 mmol), 2,2,2-trifluoroethanol (0.43 mL, 5.9 mmol) and potassium t-butoxide (0.24 mL, 1.0 M in t-butanol, 0.24 mmol) at room temperature for 1 h was prepared N-butyl-2-(4-fluorophenyl)-3-[2-(2,2,2-trifluoroethoxy)pyrimidin-4-yl]pyrazolo[1,5-α]pyridin-7-amine (52.4 mg, 97%) as an off-white solid. $^1$H NMR (CDCl$_3$): δ 8.22 (d, 1H), 7.73 (d, 1H), 7.59 (m, 2H), 7.43 (t, 1H), 7.19 (t, 2H), 6.75 (d, 1H), 6.11–6.07 (m, 2H), 4.79 (q, 2H), 3.40 (q, 2H), 1.77 (m, 2H), 1.51 (m, 2H), 1.00 (t, 3H); $^{19}$F NMR (CDCl$_3$): δ −74.03, −112.61; MS m/z 460 (M+1).

EXAMPLE 69

2-(4-Fluorophenyl)-7-pyrrolidin-1-yl-3-(2-pyrrolidin-1-ylpyrimidin-4-yl)pyrazolo[1,5-α]pyridine

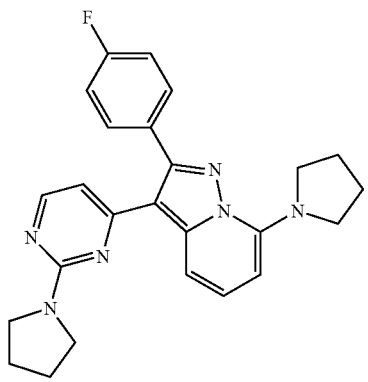

The title compound can be synthesized in a similar manner to the methods described in previous examples. $^1$H NMR (acetone-d$_6$): δ 8.11 (d, 1H), 7.98 (d, 1H), 7.76 (dd, 2H), 7.35 (t, 1H), 7.28 (t, 2H), 6.33 (d, 1H), 6.21 (d, 1H), 3.84 (m, 4H), 3.64 (br. s, 4H), 2.06 (m, 8H); MS m/z 429 (M+1).

EXAMPLE 70

3-[(4-{2-(4-Fluorophenyl)-7-[(3-hydroxypropyl)amino]pyrazolo[1,5-α]pyridin-3-yl}pyrimidin-2-yl)amino]propan-1-ol

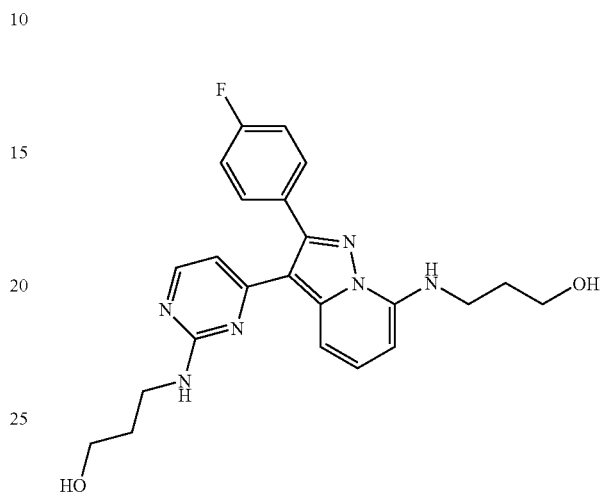

The title compound can be synthesized in a similar manner to the methods described in previous examples. $^1$H NMR (acetone-d$_6$): δ 8.04 (d, 1H), 7.83 (d, 1H), 7.76 (m, 2H), 7.40 (t, 1H), 7.30 (t, 2H), 6.86 (t, 1H), 6.4 (br. s, 1H), 6.33 (d, 1H), 6.24 (d, 1H), 3.89 (br. s, 1H), 3.81 (br.s, 2H), 3.62 (m, 5H), 2.03 (m, 2H), 1.84 (m, 2H); MS m/z 437 (M+1).

EXAMPLE 71

N-Cyclohexyl-3-[2-(cyclohexylamino)pyrimidin-4-yl]-2-(4-fluorophenyl)pyrazolo[1,5-α]pyridin-7-amine

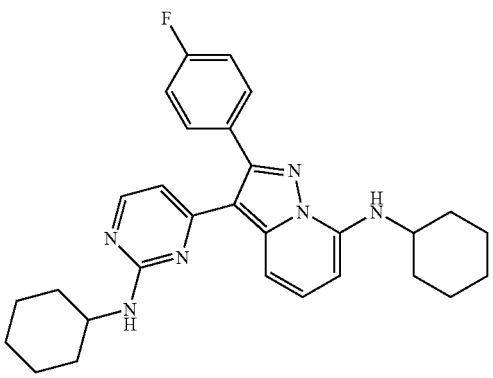

The title compound can be synthesized in a similar manner to the methods described in previous examples. $^1$H NMR (acetone-d$_6$): δ 7.98 (d, 1H), 7.75 (d, 1H), 7.65 (m, 2H), 7.33 (t, 1H), 7.24 (t, 2H), 6.28 (m, 2H), 6.19 (d, 1H), 3.81 (br.s, 1H), 3.61 (br. s, 1H), 2.13 (s, 2H), 2.04 (m, 4H), 1.79 (m, 4H), 1.65 (m, 2H), 1.47 (m, 4H), 1.32 (m, 8H); MS m/z 485 (M+1).

EXAMPLE 72

3-[2-(Cyclopentylamino)-6-methylpyrimidin-4-yl]-2-(4-fluorophenyl)pyrazolo[1,5-α]pyridin-7-amine

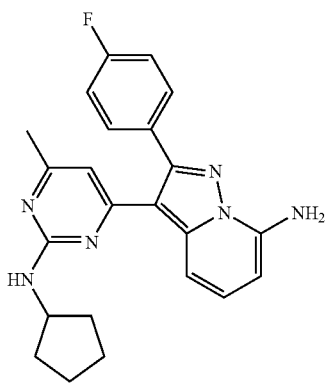

In a similar manner as described in Example 21 from 4-[7-chloro-2-(4-fluorophenyl)pyrazolo[1,5-α]pyridin-3-yl]-N-cyclopentyl-6-methyl-2-pyrimidinamine (100 mg, 0.237 mmol) and sodium azide (19 mg, 0.29 mmol) was formed 3-[2-(cyclopentylamino)-6-methylpyrimidin-4-yl]-2-(4-fluorophenyl)pyrazolo[1,5-α]pyridin-7-amine (9 mg, 9%). $^1$H NMR (CDCl$_3$) δ 7.79 (d, 1H), 7.67 (m, 2H), 7.26 (t, 1H), 7.14 (t, 2H), 6.23 (s, 1H), 6.19 (d, 1H), 5.28 (s, 2H), 5.19 (br, 1H), 4.35 (m, 1H), 2.17 (s, 3H), 2.03 (m, 2H), 1.76–1.50 (m, 6H); $^{19}$F NMR (CDCl$_3$) δ –113.52; MS m/z 403 (M+1). This material was treated with anhydrous hydrochloric acid in ether to provide a hydrochloride salt as a yellow solid.

EXAMPLE 73

7-Chloro-2-(4-fluorophenyl)-3-(2-phenylpyrimidin-4-yl)pyrazolo[1,5-α]pyridine

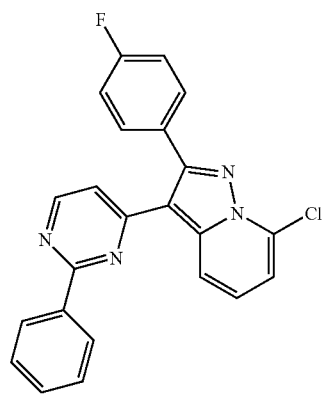

To a suspension of 1-[7-chloro-2-(4-fluorophenyl)pyrazolo[1,5-α]pyridin-3-yl]-2-propyn-1-one (36 mg, 0.12 mmol) and benzamidine hydrochloride (25 mg, 0.16 mmol) in ethanol (500 μL) was added sodium ethoxide (52 μL, 3 M in ethanol, 0.16 mmol). The reaction mixture was stirred at room temperature 16 hours. The reaction mixture was diluted with water and extracted with ethyl acetate. The organic layer was washed with water and brine, then dried over magnesium sulfate. Filtration and concentration, followed by flash chromatography (3:1 hexanes-ethyl acetate) provided 7-chloro-2-(4-fluorophenyl)-3-(2-phenylpyrimidin-4-yl)pyrazolo[1,5-α]pyridine (34 mg, 71%). R$_f$ 0.36 (3:1 hexanes-ethyl acetate); $^1$H NMR (CDCl$_3$) δ 8.60–8.56 (m, 2H), 8.52–8.48 (m, 2H), 7.67 (m, 2H), 7.56–7.52 (m, 3H), 7.39 (m, 1H), 7.22–7.11 (m, 3H), 6.93 (d, 1H); $^{19}$F NMR (CDCl$_3$) δ –112.30; MS m/z 401 (M+1).

EXAMPLE 74

6-[7-Chloro-2-(4-fluorophenyl)pyrazolo[1,5-α]pyridin-3-yl]-N-cyclopentyl-2-(cyclopentylamino)pyrimidine-4-carboxamide

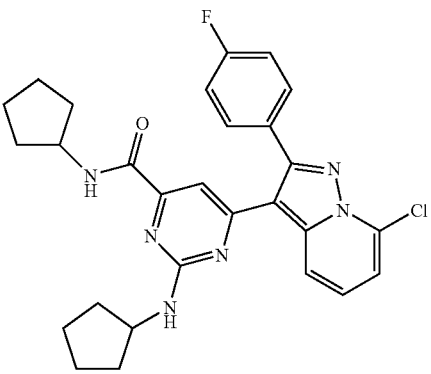

a) Methyl 6-[7-chloro-2-(4-fluorophenyl)pyrazolo[1,5-α]pyridin-3-yl]-2-(cyclopentylamino)pyrimidine-4-carboxylate To a solution of 6-[7-chloro-2-(4-fluorophenyl)pyrazolo[1,5-α]pyridin-3-yl]-2-(cyclopentylamino)-4-pyrimidinecarboxylic acid (340 mg, 0.752 mmol) in methanol (20 mL) was added (trimethylsilyl)diazomethane (376 μL, 2.0 M in hexanes, 0.752 mmol). The reaction mixture was stirred at room temperature for 16 hours. Excess (trimethylsilyl)diazomethane was added and the reaction mixture was stirred 3 days. The reaction mixture was quenched with saturated aqueous sodium bicarbonate solution and extracted with ethyl acetate. The organic layer was washed with water and brine, then dried over magnesium sulfate. Filtration and concentration followed by flash chromatography (49-1 to 29-1 dichloromethane-methanol) provided methyl 6-[7-chloro-2-(4-fluorophenyl)pyrazolo[1,5-α]pyridin-3-yl]-2-(cyclopentylamino)pyrimidine-4-carboxylate (45 mg, 13%). $^1$H NMR (CDCl$_3$) δ 8.44 (d, 1H), 7.65 (m, 2H), 7.34 (t, 1H), 7.17 (t, 2H), 7.11 (d, 1H), 7.03 (s, 1H), 5.43 (br, 1H), 4.36 (m, 1H), 3.89 (s, 3H), 2.05 (m, 2H), 1.76–1.55 (m, 6H); MS m/z 466 (M+1).

b) 6-[7-Chloro-2-(4-fluorophenyl)pyrazolo[1,5-α]pyridin-3-yl]-N-cyclopentyl-2-(cyclopentylamino)pyrimidine-4-carboxamide A solution of methyl 6-[7-chloro-2-(4-fluorophenyl)pyrazolo[1,5-α]pyridin-3-yl]-2-(cyclopentylamino)pyrimidine-4-carboxylate (45 mg, 0.097 mmol) in cyclopentylamine (1 mL) was heated at 85° C. in a sealed tube for 24 hours. The reaction mixture was cooled and the excess cyclopentylamine was removed in vacuo. The resulting residue was partitioned between ethyl acetate and saturated aqueous sodium bicarbonate solution. The organic layer was washed with water and brine, then dried over magnesium sulfate. Filtration and concentration followed by flash chromatography (4:1 hexanes:ethyl acetate) provided 6-[7-chloro-2-(4-fluorophenyl)pyrazolo[1,5-α]pyridin-3-yl]-N-cyclopentyl-2-(cyclopentylamino)pyrimidine-4-carboxamide (35 mg, 70%). $^1$H NMR (CDCl$_3$) δ 8.34 (d, 1H), 7.78 (br, 1H), 7.65 (m, 2H), 7.31–7.26 (m, 2H), 7.14 (t, 2H), 7.07 (d, 1H), 5.16 (br, 1H), 4.34–4.24 (m, 2H), 2.07–2.00 (m, 4H), 1.80–1.48 (m, 12H); MS m/z 519 (M+1). A portion of this material was treated with anhydrous hydrochloric acid in ether to provide a hydrochloride salt as a yellow solid.

EXAMPLE 75

N-Cyclopentyl-2-(cyclopentylamino)-6-[7-(cyclopentylamino)-2-(4-fluorophenyl)pyrazolo[1,5-α]pyridin-3-yl]pyrimidine-4-carboxamide

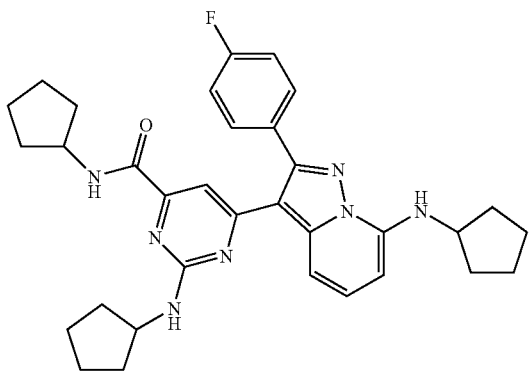

In a similar manner as described Example 1 from 6-[7-chloro-2-(4-fluorophenyl)pyrazolo[1,5-α]pyridin-3-yl]-N-cyclopentyl-2-(cyclopentylamino)pyrimidine-4-carboxamide (31 mg, 0.060 mmol) and cyclopentylamine (1 mL) was formed N-cyclopentyl-2-(cyclopentylamino)-6-[7-(cyclopentylamino)-2-(4-fluorophenyl)pyrazolo[1,5-α]pyridin-3-yl]pyrimidine-4-carboxamide (24 mg, 71%). $^1$H NMR (CDCl$_3$) δ 7.79 (br, 1H), 7.70 (d, 1H), 7.63 (m, 2H), 7.32 (t, 1H), 7.24 (s, 1H), 7.14 (t, 2H), 6.06–6.03 (m, 2H), 5.05 (d, 1H), 4.35–4.20 (m, 2H), 4.00 (m, 1H), 2.18–1.96 (m, 6H), 1.83–1.47 (m, 18H); MS m/z 568 (M+1).

EXAMPLE 76

7-Chloro-3-(2-cyclopropylpyrimidin-4-yl)-2-(4-fluorophenyl)pyrazolo[1,5-α]pyridine

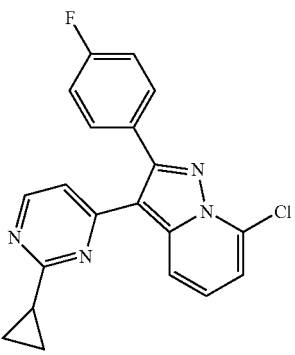

In a similar manner as described in Example 73, from 1-[7-chloro-2-(4-fluorophenyl)pyrazolo[1,5-α]pyridin-3-yl]-2-propyn-1-one (100 mg, 0.335 mmol), cyclopropylcarbamidine hydrochloride (53 mg, 0.436 mmol), and sodium ethoxide (145 μL, 3 M in ethanol, 0.436 mmol) was formed 7-chloro-3-(2-cyclopropylpyrimidin-4-yl)-2-(4-fluorophenyl)pyrazolo[1,5-α]pyridine (75 mg, 61%). $^1$H NMR (CDCl$_3$) δ 8.45 (d, 1H), 8.31 (d, 1H), 7.62 (m, 2H), 7.33 (m, 1H), 7.18–7.07 (m, 3H), 6.78 (d, 1H), 2.32 (m, 1H), 1.25–1.09 (m, 4H); MS m/z 365 (M+1).

EXAMPLE 77

7-Chloro-2-(4-fluorophenyl)-3-(2-isopropylpyrimidin-4-yl)pyrazolo[1,5-α]pyridine

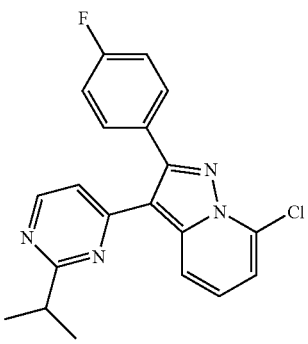

In a similar manner as described in Example 73, from 1-[7-chloro-2-(4-fluorophenyl)pyrazolo[1,5-α]pyridin-3-yl]-2-propyn-1-one (100 mg, 0.335 mmol), isopropylcabamidine hydrochloride (53 mg, 0.436 mmol), and sodium ethoxide (145 μL, 3 M in ethanol, 0.436 mmol) was formed 7-chloro-2-(4-fluorophenyl)-3-(2-isopropylpyrimidin-4-yl)pyrazolo[1,5-α]pyridine (83 mg, 67%). $^1$H NMR (CDCl$_3$) δ 8.55 (d, 1H), 8.41 (d, 1H), 7.63 (m, 2H), 7.33 (m, 1H), 7.19–7.07 (m, 3H), 6.84 (d, 1H), 3.28 (m, 1H), 1.44 (d, 6H); MS m/z 367 (M+1).

EXAMPLE 78

N-Butyl-4-[2-(4-fluorophenyl)-7-(2-furyl)pyrazolo[1,5-α]pyridin-3-yl]pyrimidin-2-amine

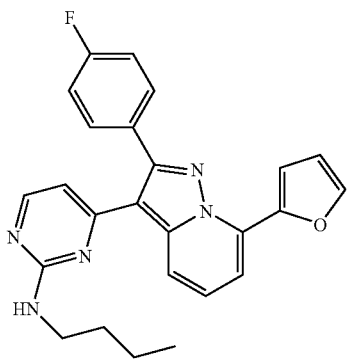

A solution of N-butyl-4-[7-chloro-2-(4-fluorophenyl)pyrazolo[1,5-α]pyridin-3-yl]pyrimidin-2-amine (35 mg, 0.089 mmol), 2-furylboronic acid (30 mg, 0.27 mmol), sodium carbonate (155 μL, 2.0 M aqueous, 0.31 mmol), and dichlorobis(triphenylphosphine)palladium(II) (3 mg, 0.004 mmol) was heated at 90° C. for 4 hours. The reaction mixture was cooled to room temperature, diluted with water, and extracted with ethyl acetate. The organic layer was washed with water and brine, then dried over magnesium sulfate. Filtration and concentration, followed by flash chromatography (4:1 hexanes:ethyl acetate) provided N-butyl-4-[2-(4-fluorophenyl)-7-(2-furyl)pyrazolo[1,5-α]pyridin-3-yl]pyrimidin-2-amine (15 mg, 39%) as a yellow solid. $R_f$ 0.19 (4:1 hexanes:ethyl acetate); $^1$H NMR (400 MHz, CDCl$_3$) δ 8.35 (d, 1H), 8.11–8.07 (m, 2H), 7.73 (m, 2H), 7.63 (s, 1H), 7.57 (d, 1H), 7.43 (t, 1H), 7.16 (t, 2H), 6.66 (m, 1H), 6.41 (d, 1H), 5.17 (m, 1H), 3.50 (q, 2H), 1.67 (m, 2H), 1.49 (m, 2H), 0.99 (t, 3H); MS m/z 428 (M+1).

EXAMPLE 79

4-[7-Chloro-2-(4-fluorophenyl)pyrazolo[1,5-α]pyridin-3-yl]-N-cyclopropylpyrimidin-2-amine

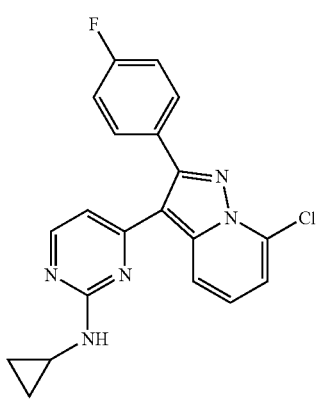

In a similar manner as described in Example 7, from 1-[7-chloro-2-(4-fluorophenyl)pyrazolo[1,5-α]pyridin-3-yl]-2-propyn-1-one (2.65 g, 8.9 mmol) and N-cyclopropylguanidine sulfate (2.27 g, 11.5 mmol) was prepared 4-[7-chloro-2-(4-fluorophenyl)pyrazolo[1,5-α]pyridin-3-yl]-N-cyclopropyl-2-pyrimidinamine (1.59 g, 47%) as a yellow solid. $^1$H NMR (CDCl$_3$): δ 8.66 (m, 1H), 8.03 (m, 1H), 7.66 (m, 2H), 7.35 (t, 1H), 7.18 (m, 3H), 6.40 (d, 1H), 6.06 (broad, 1H), 2.90 (m, 1H), 0.91 (m, 2H), 0.70 (m, 2H); $^{19}$F NMR (CDCl$_3$) δ −112.22; MS m/z 380 (M+1).

EXAMPLE 80

2-(4-Chlorophenyl)-N-cyclopentyl-3-[2-(cyclopentylamino)-4-pyrimidinyl]pyrazolo[1,5-α]pyridin-7-amine

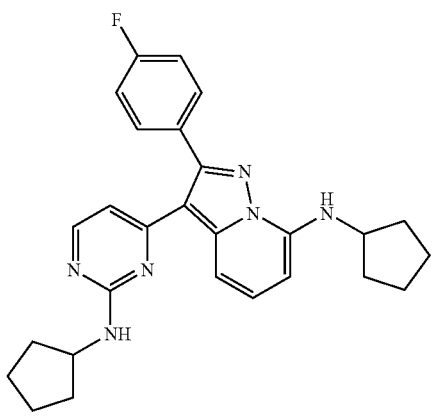

a) 1-(3-Bromo-4-chlorophenyl)-2-(6-chloro-2-pyridinyl)ethanone

In a similar manner as described in Example 1 from ethyl 3-bromo-4-chlorobenzoate (42.6 g, 171 mmol) and 6-chloro-2-picoline (18.7 mL, 171 mmol), 1-(3-bromo-4-chlorophenyl)-2-(-6-chloro-2-pyridinyl)ethanone was obtained as a pale yellow solid existing as a mixture of ketone and enol tautomers. $^1$H NMR (CDCl$_3$) of ketone: δ 8.30 (d, 1H), 7.92 (dd, 1H), 7.69–7.54 (m, 2H), 7.24 (m, 2H), 4.42 (s, 2H); MS m/z 344 (M+1).

b) 1-(3-Bromo-4-chlorophenyl)-2-(6-chloro-2-pyridinyl)ethanone oxime

In a similar manner as described in Example 1 from 1-(3-bromo-4-chlorophenyl)-2-(6-chloro-2-pyridinyl)ethanone was obtained 1-(3-bromo-4-chlorophenyl)-2-(6-chloro-2-pyridinyl)ethanone oxime (22.0 g, yield 36% for the two steps) as a white solid. $^1$H NMR (CDCl$_3$): δ 8.20 (b, 1H), 8.06 (d, 1H), 7.62–7.53 (m, 2H), 7.42 (d, 1H), 7.18–7.14 (m, 2H), 4.32 (s, 2H); MS m/z 359 (M+1).

c) 2-(3-Bromo-4-chlorophenyl)-7-chloropyrazolo[1,5-α]pyridine

In a similar manner as described in Example 1 from 1-(3-bromo-4-chlorophenyl)-2-(6-chloro-2-pyridinyl)ethanone oxime (17.57 g, 48.8 mmol) was obtained 2-(3-bromo-4-chlorophenyl)-7-chloropyrazolo[1,5-α]pyridine (13.7 g, 82%). $^1$H NMR (CDCl$_3$): δ 8.28 (d, 1H), 7.99 (dd, 1H), 7.52 (m, 2H), 7.10 (t, 1H), 6.94–6.90 (m, 2H); MS m/z 341 (M+1).

d) 1-[2-(3-Bromo-4-chlorophenyl)-7-chloropyrazolo[1,5-α]pyridin-3-yl]ethanone

In a similar manner as described in Example 1 from 2-(3-bromo-4-chlorophenyl)-7-chloropyrazolo[1,5-α]pyridine (13.9 g, 40.8 mmol), 1-[2-(3-bromo-4-chlorophenyl)-7-chloropyrazolo[1,5-α]pyridin-3-yl]ethanone (12.5 g, 80%) was obtained as a tan solid. $^1$H NMR (CDCl$_3$): δ 8.40 (d, 1H), 7.92 (d, 1H), 7.61–7.44 (m, 3H), 7.19 (d, 1H), 2.21(s, 3H); MS m/z 383 (M+1).

e) 1-[2-(3-Bromo-4-chlorophenyl)-7-(cyclopentylamino)pyrazolo[1,5-α]pyridin-3-yl]ethanone In a similar manner as described in Example 1 1-[2-(3-bromo-4-chlorophenyl)-7-chloropyrazolo[1,5-α]pyridin-3-yl]ethanone (12.5 g, 32.5 mmol), 1-[2-(3-bromo-4-chlorophenyl)-7-(cyclopentylamino)pyrazolo[1,5-α]pyridin-3-yl]ethanone was obtained as a yellow foam. $^1$H NMR (CDCl$_3$): δ 7.91 (d, 1H), 7.62–7.41 (m, 4H), 6.16 (d, 1H), 6.02 (d, 1H), 4.00 (m, 1H), 2.22 (s, 3H), 2.13 (m, 2H), 1.82–1.65 (m, 6H); MS m/z 432 (M+1).

f) (2E)-1-[2-(3-Bromo-4-chlorophenyl)-7-(cyclopentylamino)pyrazolo[1,5-α]pyridin-3-yl]-3-(dimethylamino)-2-propen-1-one In a similar manner as described in Example 1 from 1-[2-(3-bromo-4-chlorophenyl)-7-(cyclopentylamino)pyrazolo[1,5-α]pyridin-3-yl]ethanone, (2E)-1-[2-(3-bromo-4-chlorophenyl)-7-(cyclopentylamino)pyrazolo[1,5-α]pyridin-3-yl]-3-(dimethylamino)-2-propen-1-one (6.45 g, combined yield for steps e and f 41%) was obtained as a brown syrup. $^1$H NMR (CDCl$_3$): δ 8.08 (d, 1H), 7.69–7.57 (m, 3H), 7.51 (d, 1H), 7.32 (t, 1H), 6.04 (d, 1H), 5.96 (d, 1H), 5.13 (d, 1H), 4.00 (m, 1H), 3.0 (b, 3H), 2.62 (b, 3H), 2.13 (m, 2H), 1.84–1.68 (m, 6H); MS m/z 487 (M+1).

g) 2-(3-Bromo-4-chlorophenyl)-N-cyclopentyl-3-[2-(cyclopentylamino)-4-pyrimidinyl]pyrazolo[1,5-α]pyridin-7-amine In a similar manner as described in Example 1 from (2E)-1-[2-(3-bromo-4-chlorophenyl)-7-(cyclopentylamino)pyrazolo[1,5-α]pyridin-3-yl]-3-(dimethylamino)-2-propen-1-one (3.00 g, 6.15 mmol), 2-(3-bromo-4-chlorophenyl)-N-cyclopentyl-3-[2-(cyclopentylamino)-4-pyrimidinyl]pyrazolo[1,5-α]pyridin-7-amine (2.71 g, 80%) was obtained as a yellow solid. $^1$H NMR (CDCl$_3$): δ 8.08 (d, 1H), 8.02 (s, 1H), 7.64 (d, 1H), 7.50 (m, 2H), 7.53 (t, 1H), 6.38 (d, 1H), 6.05 (d, 1H), 6.00 (d, 1H), 5.13 (d, 1H), 4.28 (m, 1H), 4.01 (m, 1H), 2.15 (m, 2H), 2.04 (m, 2H), 1.83–1.49 (m, 12H); MS m/z 551 (M+1).

h) 2-(4-Chlorophenyl)-N-cyclopentyl-3-[2-(cyclopentylamino)-4-pyrimidinyl]-pyrazolo[1,5-α]pyridin-7-amine To a solution of 2-(3-bromo-4-chlorophenyl)-N-cyclopentyl-3-[2-(cyclopentylamino)-4-pyrimidinyl]pyrazolo[1,5-α]pyridin-7-amine (200 mg, 0.36 mmol) in toluene (15 mL) was added 2,2'-azobisisobutyronitril (30 mg, 0.18 mmol) and tributyltin hydride (282 mg, 97 mmol). After heated at reflux for 24 hours, the reaction mixture was cooled to room temperature. Concentration followed by purification with flash chromatograph (30:70 ethyl acetate/hexanes) gave 2-(4-chlorophenyl)-N-cyclopentyl-3-[2-(cyclopentylamino)-4-pyrimidinyl]pyrazolo[1,5-α]pyridin-7-amine as a white foam. $^1$H NMR (CDCl$_3$): δ 8.02 (d, 1H), 7.72 (m, 1H), 7.60 (d, 2H), 7.41 (d, 2H), 7.35 (m, 1H), 6.31 (d, 1H), 6.03 (m, 2H), 5.17 (br, 1H), 4.32 (m, 1H), 4.00 (m, 1H), 2.18–2.05 (m, 4H), 1.82–1.50 (m, 12H). MS m/z 474 (M+1).

EXAMPLE 81

N-Cyclopentyl-3-[2-(dimethylamino)-6-methylpyrimidin-4-yl]-2-(4-fluorophenyl)pyrazolo[1,5-α]pyridin-7-amine

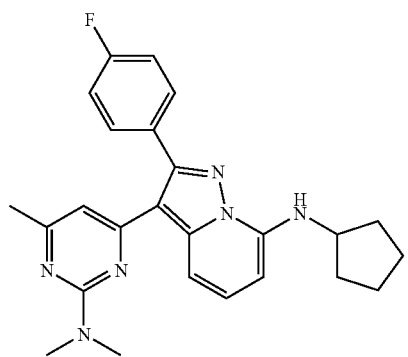

The title compound was synthesized in an similar manner to that described in Example 8 to give a clear oil. $^1$H NMR (CDCl$_3$): δ 7.63–7.60 (m, 3H), 7.24 (m, 1H), 7.07 (t, 2H), 6.14 (s, 1H), 5.98–5.96 (m, 2H), 3.96 (m, 1H), 3.17 (s, 6H), 2.16 (s, 3H), 2.14–2.06 (m, 2H), 1.78–1.59 (m, 6H). MS m/z 431 (M+1). This material was treated with anhydrous hydrogen chloride in ether to give the corresponding HCl salt as a yellow solid.

EXAMPLE 82

N-Cyclopentyl-3-[2-(cyclopentylamino)-6-phenylpyrimidin-4-yl]-2-(4-fluorophenyl)pyrazolo[1,5-α]pyridin-7-amine

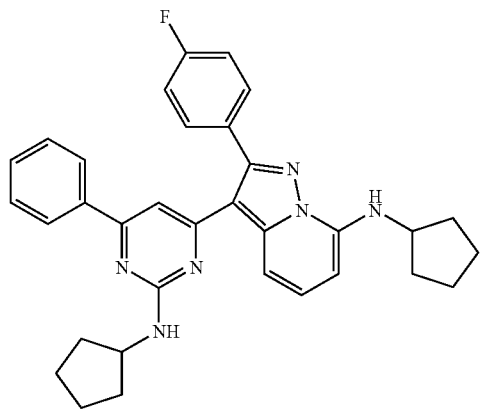

In a similar manner as described in Example 1 from 4-[7-chloro-2-(4-fluorophenyl)pyrazolo[1,5-α]pyridin-3-yl]-N-cyclopentyl-6-phenylpyrimidin-2-amine (60 mg, 0.12 mmol) and cyclopentylamine (1 mL) was formed N-cyclopentyl-3-[2-(cyclopentylamino)-6-phenylpyrimidin-4-yl]-2-(4-fluorophenyl)pyrazolo[1,5-α]pyridin-7-amine (64.1 mg, 97%) as a clear oil. $^1$H NMR (CDCl$_3$): δ 7.84–7.46 (m, 5H), 7.44–7.33 (m, 4H), 7.22 (t, 2H), 6.81 (s, 1H), 6.10–6.07 (m, 2H), 5.24 (d, 1 h), 4.49 (m, 1H), 4.05 (m, 1H), 2.17 (m, 4H), 1.87–1.59 (m, 12H). $^{19}$F NMR (CDCl$_3$): δ −113.49; MS m/z 533 (M+1). This material was treated with anhydrous hydrogen chloride in ether to give the corresponding HCl salt as a orange solid.

EXAMPLE 83

N-Cyclopentyl-6-[2-(4-fluorophenyl)-7-(methylthio)pyrazolo[1,5-α]pyridin-3-yl]pyrimidin-4-amine

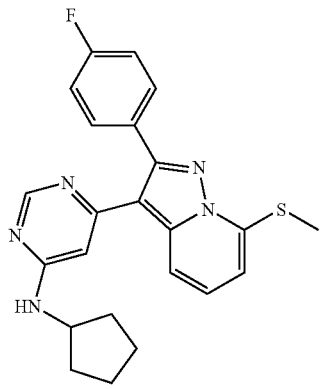

The title compound could be synthesized in a similar manner to that described in Example 56 to give a peach solid. $^1$H NMR (CDCl$_3$) δ 8.60 (s, 1H), 8.26 (d, 1H), 7.86 (m, 2H), 7.32 (t, 1H), 7.15 (t, 2H), 6.70 (d, 1H), 6.08 (s, 1H), 4.95 (br, 1H), 3.58 (br, 1H), 2.65 (s, 3H), 1.85–1.50 (m, 6H), 1.38–1.22 (m, 2H); MS m/z 420 (M+1).

EXAMPLE 84

N-cyclopentyl-3-[6-(cyclopentylamino)pyrimidin-4-yl]-2-(4-fluorophenyl)pyrazolo[1,5-α]pyridin-7-amine

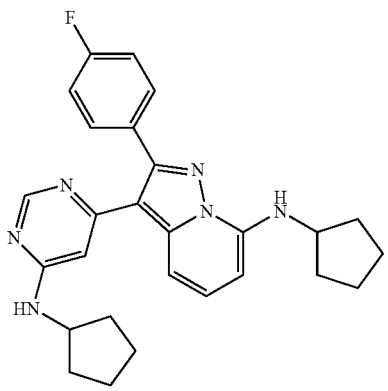

The title compound could be synthesized in a similar manner to that described in previous examples to give a light brown solid. R$_f$ 0.18 (3:1 hexanes-ethyl acetate); $^1$H NMR (CDCl$_3$) δ 8.58 (s, 1H), 7.74–7.64 (m, 3H), 7.32 (d, 1H), 7.16 (t, 2H), 6.05–5.98 (m, 3H), 4.98 (br, 1H), 4.02 (m, 1H), 3.53 (br, 1H), 2.18–2.13 (m, 2H), 1.84–1.55 (m, 12H), 1.38–1.33 (m, 2H); MS m/z 457 (M+1).

EXAMPLE 85

Biological Activity

In the following example, "MEM" means Minimal Essential Media; "FBS" means Fetal Bovine Serum; "NP40" and "Igepal" are detergents; "MOI" means Multiplicity of Infection; "NaOH" means sodium hydroxide; "MgCl$_2$" means magnesium chloride; "dATP" means deoxyadenosine 5' triphosphate; "dUTP" means deoxyuridine 5' triphosphate; "dCTP" means dexoxycytidine 5' triphosphate; "dGTP" means deoxyguanosine 5' triphosphate; "GuSCN" means Guanidinium thiocyanate; "EDTA" means ethylenediamine tetraacetic acid; "TE" means Tris-EDTA; "SCC" means sodium chloride/sodium citrate; "APE" means a solution of ammonia acetate, ammonia phosphate, EDTA; "PBS" means phosphate buffered saline; and "HRP" means horseradish peroxidase.

a) Tissue Culture and HSV Infection.

Vero 76 cells were maintained in MEM with Earle's salts, L-glutamine, 8% FBS (Hyclone, A-1111-L) and 100 units/mL Penicillin-100 μg/mL Streptomycin. For assay conditions, FBS was reduced to 2%. Cells are seeded into 96-well tissue culture plates at a density of 5×10$^4$ cells/well after being incubated for 45 min at 37° C. in the presence of HSV-1 or HSV-2 (MOI=0.001). Test compounds are added to the wells and the plates are incubated at 37° C. for 40–48 hours. Cell lysates are prepared as follows: media was removed and replaced with 150 μL/well 0.2 N NaOH with 1% Igepal CA 630 or NP-40. Plates were incubated up to 14 days at room temperature in a humidified chamber to prevent evaporation.

(b) Preparation of Detection DNA.

For the detection probe, a gel-purified, digoxigenin-labeled, 710-bp PCR fragment of the HSV UL-15 sequence was utilized. PCR conditions included 0.5 μM primers, 180 μM dTP, 20 μM dUTP-digoxigenin (Boehringer Mannheim 1558706), 200 μM each of dATP, dCTP, and dGTP, 1×PCR Buffer II (Perkin Elmer), 2.5 mM MgCl$_2$, 0.025 units/μL of AmpliTaq Gold polymerase (Perkin Elmer), and 5 ng of gel-purified HSV DNA per 100 μL. Extension conditions were 10 min at 95° C., followed by 30 cycles of 95° C. for 1 min, 55° C. for 30 sec, and 72° C. for 2 min. The amplification was completed with a 10-min incubation at 72° C. Primers were selected to amplify a 728 bp probe spanning a section of the HSV1 UL15 open reading frame (nucleotides 249–977). Single-stranded transcripts were purified with Promega M13 Wizard kits. The final product was mixed 1:1 with a mixture of 6 M GuSCN, 100 mM EDTA and 200 μg/mL herring sperm DNA and stored at 4° C.

(c) Preparation of Capture Plates.

The capture DNA plasmid (HSV UL13 region in pUC) was linearized by cutting with Xba I, denatured for 15 min at 95° C. and diluted immediately into Reacti-Bind DNA Coating Solution (Pierce, 17250, diluted 1:1 with TE buffer, pH 8) at 1 ng/μL 75 μL/well were added to Corning (#3922 or 9690) white 96-well plates and incubated at room temperature for at least 4 hrs before washing twice with 300 μL/well 0.2×SSC/0.05% Tween-20 (SSC/T buffer). The plates were then incubated overnight at room temperature with 150 μL/well 0.2 N NaOH, 1% IGEPAL and 10 μg/mL herring sperm DNA.

(d) Hybridization.

Twenty-seven (27) μL of cell lysate was combined with 45 μL of hybridization solution (final concentration: 3M GuSCN, 50 mM EDTA, 100 μg/ml salmon sperm DNA, 5× Denhardt's solution, 0.25×APE, and 5 ng of the digoxigenin-labeled detection probe). APE is 1.5 M $NH_4$-acetate, 0.15 M ammonium phosphate, and 5 mM EDTA adjusted to pH 6.0. Mineral oil (50 μL) was added to prevent evaporation. The hybridization plates were incubated at 95° C. for 10 minutes to denature the DNA, then incubated at 42° C. overnight. The wells were washed 6× with 300 μL/well SSC/T buffer then incubated with 75 μL/well anti-digoxigenin-HRP-conjugated antibody (Boehringer Mannheim 1207733, 1:5000 in TE) for 30 min at room temperature. The wells were washed 6× with 300 μL/well with PBS/0.05% Tween-20 before 75 μL/well SuperSignal LBA substrate (Pierce) was added. The plates were incubated at room temperature for 30 minutes and chemiluminescence was measured in a Wallac Victor reader.

e) Results.

The following results were obtained for HSV-1.

| Example No. | $IC_{50}$ (μM) |
|---|---|
| 1 | 0.3 |
| 2 | 0.7 |
| 3 | 0.5 |
| 4 | 0.6 |
| 5 | 5.0 |
| 6 | 0.2 |
| 7 | 3.9 |
| 8 | 0.8 |
| 9 | 8.0 |
| 10 | 5.0 |
| 11 | 1.0 |
| 12 | 0.5 |
| 13 | 6.0 |
| 14 | 5.0 |
| 15 | 5.0 |
| 16 | 40.0 |
| 17 | 3.0 |
| 18 | 20.0 |
| 19 | 2.5 |
| 20 | 3.0 |
| 21 | 1.0 |
| 22 | 5.0 |
| 23 | 1.0 |
| 24 | 10.0 |
| 25 | 15.0 |
| 26 | 1.5 |
| 27 | 1.3 |
| 28 | 2.0 |
| 29 | 0.3 |
| 30 | 5.0 |
| 31 | 1.0 |
| 32 | 5.0 |
| 33 | 0.2 |
| 34 | 0.3 |
| 35 | 0.9 |
| 36 | 0.8 |
| 37 | 15.0 |
| 38 | 5.0 |
| 39 | 1.0 |
| 40 | 15.0 |
| 41 | 6.0 |
| 42 | 10.0 |
| 43 | 3.0 |
| 44 | 4.0 |
| 45 | 5.0 |
| 46 | 7.0 |
| 47 | 0.4 |
| 48 | 0.3 |
| 49 | 1.2 |
| 50 | 5.0 |
| 51 | 5.0 |
| 53 | 1.0 |
| 54 | 0.5 |
| 55 | 1.2 |
| 57 | 0.7 |
| 58 | 10.5 |
| 59 | 4.0 |
| 61 | >20 |
| 68 | >20 |
| 69 | 4.2 |
| 72 | 4.4 |
| 73 | >20 |
| 74 | >20 |
| 75 | >20 |
| 76 | >20 |
| 77 | >20 |
| 78 | 0.95 |
| 79 | >20 |
| 80 | 0.54 |
| 81 | >20 |
| 82 | >20 |
| 83 | 1.3 |
| 84 | 1.3 |

The results demonstrate that the compounds of the present invention are useful for the treatment and prophylaxis of herpes viral infections.

The invention claimed is:

1. A compound of formula (I):

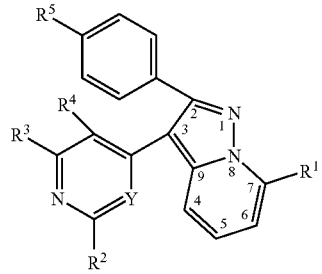

wherein:

$R^1$ is selected from the group consisting of halo, —$NR^7R^8$, Ay, —$NR^7$Ay, Het, —$NH(CH_2)_m$Het, and —$NH(CH_2)_l$Ay;

each $R^7$ and $R^8$ are the same or different and are independently selected from the group consisting of H, alkyl, cycloalkyl, alkenyl, cycloalkenyl, alkylhydroxy, amine, alkylamine, alkylcarboky, alkylcarboxamide, alkyl alkoxycarbonyl, alkylthioamide, alkylsulfonyl, alkylsulfonamide, alkylether, —$(CH_2)_l$-cycloalkyl, —$(CH_2)_l$NHCOR$^9$ and —$(CH_2)_m$ $SO_2NHCOR^9$;

l is 1–6;

m is 0–6;

$R^9$ is H, alkyl, cycloalkyl, alkylhydroxy, amine, alkylamine, alkylcarboxy and alkylether;

Ay is aryl;

Het is a 5- or 6-membered heterocyclic or heteroaryl group;

R² is selected from the group consisting of H, halo, alkyl, cycloalkyl, alkenyl, cycloalkenyl, —NR⁷R⁵, —OR⁷, —OAy, —S(O)ₙR⁷, —S(O)ₙAy, —R¹⁰NR⁷R⁸, —R¹⁰NR⁷Ay, Ay, Het, —NH(CH₂)ₘHet and —O(CH₂)ₘHet;

n is 0, or 2;

R¹⁰ is alkyl or alkenyl;

Y is N;

R³ and R⁴ are each independently selected from the group consisting of H, halo, hydroxy, alkyl, alkylhydroxy, alkylamine, alkylether, —OR⁷, —OAy, —NR⁷R⁸, —NR⁷Ay, carboxy, carboxamide, —SO₂NHR⁹, Het and Ay; and R⁵ is halo;

or a pharmaceutically acceptable salt thereof.

2. The compound according to claim 1 wherein R¹ is selected from the group consisting of —NR⁷R⁸, —NR⁷Ay, Ay, Het, —NH(CH₂)ₘHet, and —NH(CH₂)ₜAy.

3. The Compound according to claim 1 wherein R¹ is —NR⁷R⁸.

4. The compound according to claim 1 wherein R² is selected from the group consisting of —NR⁷R⁸, —OR⁷, —OAy, —S(O)ₙR⁷, —S(O)ₙAy, —R¹⁰NR⁷R⁸, —R¹⁰NR⁷Ay, Ay, Het, —NH(CH₂)ₘHet and —O(CH₂)ₘHet.

5. The compound according to claim 4 wherein R² is selected from the group consisting of —NR⁷R⁸ and Het.

6. The compound according to claim 1 wherein R³ and R⁴ are each independently selected from the group consisting of H, hydroxy, alkyl, alkylhydroxy, alkylamine, alkylether, —NR⁷R⁸, —NR⁷Ay, carboxy and Ay.

7. The compound according to claim 6 wherein R³ is selected from the group consisting of H, alkyl, alkylhydroxy, alkylamine, alkylether, and Ay.

8. The compound according to claim 6 wherein R⁴ is H.

9. The compound according to claim 1 wherein R⁵ is fluoro.

10. A compound selected from the group consisting of:
N-cyclopentyl-3-[2-(cyclopentylamino)-4-pyrimidinyl]-2-(4-fluorophenyl)pyrazolo[1,5-α]pyridin-7-amine;
2-(4-Bromophenyl)-N-butyl-3-[2-(butylamino)-4-pyrimidinyl]pyrazolo[1,5-α]pyridin-7-amine;
N-Butyl-3-[2-(butylamino)-4-pyrimidinyl]-2-(4-fluorophenyl)pyrazolo[1,5-α]pyridin-7-amine;
N-Butyl-3-[2-(cyclopropylamino)-4-pyrimidinyl]-2-(4-fluorophenyl)pyrazolo[1,5-α]pyridin-7-amine;
N-Butyl-2-(4-fluorophenyl)-3-[2-(1-pyrrolidinyl)-4-pyrimidinyl]pyrazolo[1,5-α]pyridin-7-amine;
N-Butyl-3-[2-(cyclopentylamino)-4-pyrimidinyl]-2-(4-fluorophenyl)pyrazolo[1,5-α]pyridin-7-amine;
4-[7-Chloro-2-(4-fluorophenyl)pyrazolo[1,5-α]pyridin-3-yl]-N-cyclopentyl-6-methyl-2-pyrimidinamine;
N-Cyclopentyl-3-[2-(cyclopentylamino)-6-methyl-4-pyrimidinyl]-2-(4-fluorophenyl)pyrazolo[1,5-a]pyridin-7-amine;
2-(4-Bromophenyl)-N-butyl-3-[2-(1-pyrrolidinyl)-4-pyrimidinyl]pyrazolo[1,5-α]pyridin-7-amine;
2-(4-Bromophenyl)-N-butyl-3-[2-(cyclopentylamino)-4-pyrimidinyl]pyrazolo[1,5-α]pyridin-7-amine;
N-cyclopentyl-3-[2-(dimethylamino)-4-pyrimidinyl]-2-(4-fluorophenyl)pyrazolo[1,5-α]pyridin-7-amine;
3-(2-Amino-4-pyrimidinyl)-N-cyclopentyl-2-(4-fluorophenyl)pyrazolo[1,5-α]pyridin-7-amine;
N-Cyclopentyl-2-(4-fluorophenyl)-3-(2-{[3-(4-morpholinyl)propyl]amino}-4-pyrimidinyl)pyrazolo[1,5-α]pyridin-7-amine;
N-Cyclopentyl-4-[2-(4-fluorophenyl)-7-hydrazinopyrazolo[1,5-α]pyridin-3-yl]-6-methyl-2-pyrimidinamine;
N-Cyclopentyl-4-[2-(4-fluorophenyl)-7-(4-methyl-1-piperazinyl)pyrazolo[1,5-α]pyridin-3-yl]-6-methyl-2-pyrimidinamine;
N-cyclopentyl-3-[2-cyclopentylamino)-6-[(tetrahydro-2H-pyran-2-yloxy)methyl]-4-pyrimidinyl]-2-(4-fluorophenyl)pyrazolo[1,5-α]pyridin-7-amine;
[6-[7-Chloro-2-(4-fluorophenyl)pyrazolo[1,5-α]pyridin-3-yl]-2-(cyclopentylamino)-4-pyrimidinyl]methanol;
[{4-[7-(Cyclopentylamino)-2-(4-fluorophenyl)pyrazolo[1,5-α]pyridin-3-yl]-2-pyrimidinyl}(methyl)amino]acetic acid;
N-Cyclopentyl-4-[2-(4-fluorophenyl)-7-(4-methyl-1-piperazinyl)pyrazolo[1,5-α]pyridin-3-yl]-6-phenyl-2-pyrimidinamine hydrochloride;
N¹-[3-[2-(Cyclopentylamino)-6-phenyl-4-pyrimidinyl]-2-(4-fluorophenyl)pyrazolo-[1,5-α]pyridin-7-yl]-1,2-ethanediamine;
3-[2-(Cyclopentylamino)-4-pyrimidinyl]-2-(4-fluorophenyl)pyrazolo[1,5-α]pyridin-7-amine;
{2-(Cyclopentylamino)-6-[7-(cyclopentylamino)-2-(4-fluorophenyl)pyrazolo[1,5-α]pyridin-3-yl]-4-pyrimidinyl}methanol;
3-[2-(Cyclopentylamino)-4-pyrimidinyl]-2-(4-fluorophenyl)-N-(4-methoxyphenyl)-pyrazolo[1,5-α]pyridin-7-amine;
Methyl {[3-[2-(cyclopentylamino)-6-methyl-4-pyrimidinyl]-2-(4-fluorophenyl)-pyrazolo[1,5-α]pyridin-7-yl]amino}acetate;
{[3-[2-(Cyclopentylamino)-6-methyl-4-pyrimidinyl]-2-(4-fluorophenyl)pyrazolo[1,5-α]pyridin-7-yl]amino}acetic acid;
4-[7-Chloro-2-(4-fluorophenyl)pyrazolo[1,5-α]pyridin-3-yl]-N-cyclopentyl-2-pyrimidinamine;
6-[7-Chloro-2-(4-fluorophenyl)pyrazolo[1,5-α]pyridin-3-yl]-2-(cyclopentylamino)-4-pyrimidinecarboxylic acid;
N-Cyclopentyl-4-[2-(4-fluorophenyl)-7-(1-pyrrolidinyl)pyrazolo[1,5-α]pyridin-3-yl]-2-pyrimidinamine;
4-[2-(4-Fluorophenyl)-7-(1-pyrrolidinyl)pyrazolo[1,5-α]pyridin-3-yl]-N,N-dimethyl-2-pyrimidinamine;
3-[2-(Butylamino)-4-pyrimidinyl]-N-cyclopropyl-2-(4-fluorophenyl)pyrazolo[1,5-a]pyridin-7-amine;
3-[2-(Butylamino)-4-pyrimidinyl]-2-(4-fluorophenyl)-N,N-dimethylpyrazolo[1,5-α]pyridin-7-amine;
N-Butyl-4-[2-(4-fluorophenyl)-7-(4-methyl-1-piperazinyl)pyrazolo[1,5-α]pyridin-3-yl]-2-pyrimidinamine;
N-Butyl-4-[2-(4-fluorophenyl)-7-(4-morpholinyl)pyrazolo[1,5-α]pyridin-3-yl]-2-pyrimidinamine;
N-Butyl-2-(4-fluorophenyl)-3-[2-(methylsulfinyl)-4-pyrimidinyl]pyrazolo[1,5-α]pyridin-7-amine;
3-({4-[7-(Butylamino)-2-(4-fluorophenyl)pyrazolo[1,5-α]pyridin-3-yl]-2-pyrimidinyl}amino)-1-propanol;
3-[2-(Allylamino)-4-pyrimidinyl]-N-butyl-2-(4-fluorophenyl)pyrazolo[1,5-α]pyridin-7-amine;
N-Butyl-2-(4-fluorophenyl)-3-[2-(4-morpholinyl)-4-pyrimidinyl]pyrazolo[1,5-α]pyridin-7-amine;
2-(4-(4-[7-(Butylamino)-2-(4-fluorophenyl)pyrazolo[1,5-α]pyridin-3-yl]-2-pyrimidinyl)-1-piperazinyl)ethanol;
N-Butyl-2-(4-fluorophenyl)-3-{2-[4-(2-methoxyethyl)-1-piperazinyl]-4-pyrimidinyl}pyrazolo[1,5-α]pyridin-7-amine;
N-Butyl-2-(4-fluorophenyl)-3-{2-[(2-pyridinylmethyl)amino]-4-pyrimidinyl}-pyrazolo[1,5-α]pyridin-7-amine;

N-Butyl-2-(4-fluorophenyl)-3-(2-{[3-(1H-imidazol-1-yl) propyl]amino}-4-pyrimidinyl)pyrazolo[1,5-α]pyridin-7-amine;

N-Butyl-2-(4-fluorophenyl)-3-(2-{[2-(4-morpholinyl) ethyl]amino}-4-pyrimidinyl)pyrazolo[1,5-α]pyridin-7-amine;

N-Butyl-2-(4-fluorophenyl)-3-{2-[2-(4-morpholinyl) ethoxy]-4-pyrimidinyl}pyrazolo-[1,5-α]pyridin-7-amine;

3-[2-(Butylamino)-4-pyrimidinyl]-2-(4-fluorophenyl)-N-[2-(4-morpholinyl)ethyl]-pyrazolo[1,5-α]pyridin-7-amine;

3-[2-(Butylamino)-4-pyrimidinyl]-2-(4-fluorophenyl)-N-(2-methoxyethyl)pyrazolo-[1,5-α]pyridin-7-amine;

3-[2-(Butylamino)-4-pyrimidinyl]-2-(4-fluorophenyl)-N-methylpyrazolo[1,5-α]-pyridin-7-amine;

4-[7-Chloro-2-(4-fluorophenyl)pyrazolo[1,5-α]pyridin-3-yl-N-cyclopentyl-6-[(dimethylamino)methyl]-2-pyrimidinamine;

N-Cyclopentyl-3-{2-(cyclopentylamino)-6-[(dimethylamino)methyl]-4-pyrimidinyl}-2-(4-fluorophenyl) pyrazolo[1,5-α]pyridin-7-amine;

4-(7-Chloro-2-(4-fluorophenyl)pyrazolo[1,5-α]pyridin-3-yl]-cyclopentyl-5-methyl-2-pyrimidinamine; and N-Cyclopentyl-3-[2-(cyclopentylamino)-5-methyl-4-pyrimidinyl]-2-(4-fluorophenyl)-pyrazolo[1,5-α]pyridin-7-amine;

N-Allyl-3-[2-(butylamino)-4-pyrimidinyl](4-fluorophenyl)-pyrazolo[1,5-α]pyridin-7-amine;

3-[2-(Butylamino)-4-pyrimidinyl]-2-(4-fluorophenyl)-N-propylpyrazolo[1,5-α]pyridin-7-amine;

N-Butyl-2-(4-fluorophenyl)-3-[2-(2,2,2-trifluoroethoxy) pyrimidin-4-yl]pyrazolo[1,5-α]pyridin-7-amine;

2-(4-Fluorophenyl)-7-pyrrolidin-1-yl-3-(2-pyrrolidin-1-ylpyrimidin-4-yl)pyrazolo[1,5-α]pyridine;

3-[(4-{2-(4-Fluorophenyl)-7-[(3-hydroxypropyl)amino] pyrazolo[1,5-α]pyridin-3-yl}pyrimidin-2-yl)amino] propan-1-ol;

N-Cyclohexyl-3-[2-(cyclohexylamino)pyrimidin-4-yl]-2-(4-fluorophenyl)pyrazolo[1,5-α]pyridin-7-amine;

3-[2-(Cyclopentylamino)-6-methylpyrimidin-4-yl]-2-(4-fluorophenyl)pyrazolo[1,5-α]pyridine-7-amine;

7-Chloro-2-(4-fluorophenyl)-3-(2-phenylpyrimidin-4-yl) pyrazolo[1,5-α]pyridine;

6-[7-Chloro-2-(4-fluorophenyl)pyrazolo[1,5-α]pyridin-3-yl]-N-cyclopentyl-2-(cyclopentylamino)pyrimidine-4-carboxamide;

N-Cyclopentyl-2-(cyclopentylamino)-6-[7-(cyclopentylamino)-2-(4-fluorophenyl)pyrazolo[1,5-α]pyridin-3-yl]pyrimidine-4-carboxamide;

7-Chloro-3-(2-cyclopropylpyrimidin-4-yl)-2-(4-fluorophenyl)pyrazolo[1,5-α]pyridine;

7-Chloro-2-(4-fluorophenyl)-3-(2-isopropylpyrimidin-4-yl)pyrazolo[1,5-α]pyridine;

N-Butyl-4-[2-(4-fluorophenyl)-7-(2-furyl)pyrazolo[1,5-α]pyridin-3-yl]pyrimidin-2-amine;

4-[7-Chloro-2-(4-fluorophenyl)pyrazolo[1,5-α]pyridin-3-yl]-N-cyclopropylpyrimidin-2-amine;

2-(4-Chlorophenyl)-N-cyclopentyl-3-[2-(cyclopentylamino)-4-pyrimidinyl]pyrazolo[1,5-α]pyridin-7-amine;

N-Cyclopentyl-3-[2-(dimethylamino)-6-methylpyrimidin-4-yl]-2-(4-fluorophenyl)pyrazolo[1,5-α]pyridin-7-amine;

N-Cyclopentyl-3-[2-(cyclopentylamino)-6-phenylpyrimidin-4-yl]-2-(4-fluorophenyl)pyrazolo[1,5-α]pyridin-7-amine;

N-cyclopentyl-3-[6-(cyclopentylamino)pyrimidin-4-yl]-2-(4-fluorophenyl)pyrazolo[1,5-α]pyridin-7-amine and pharmaceutically acceptable salts thereof.

11. N-cyclopentyl-3-[2-(cyclopentylamino)-4-pyrimidinyl]-2-(4-fluorophenyl)-pyrazolo[1,5-α]pyridin-7-amine, or a pharmaceutically acceptable salt thereof.

12. N-Butyl-3-[2-(cyclopentylamino)-4-pyrimidinyl]2-(4-fluorophenyl)-pyrazolo[1,5-α]pyridin-7-amine, or a pharmaceutically acceptable salts thereof.

13. 3-[2-(Butylamino)-4-pyrimidinyl]-N-cyclopropyl-2-(4-fluorophenyl)-pyrazolo[1,5-α]pyridin-7-amine, or a pharmaceutically acceptable salt thereof.

14. N-Butyl-4-[2-(4-fluorophenyl)-7-(4-morpholinyl) pyrazolo[1,5-α]pyridin-3-yl]-2-pyrimidinamine, or a pharmaceutically acceptable salt thereof.

15. N-Butyl-3-[2-(butylamino)-4-pyrimidinyl]-2-(4-fluorophenyl)pyrazolo[1,5-α]pyridin-7-amine, or a pharmaceutically acceptable salt thereof.

16. A pharmaceutical formulation comprising a compound according to claim 1.

17. The pharmaceutical formulation according to claim 14 further comprising a pharmaceutically acceptable carrier or diluent.

18. The pharmaceutical formulation according to claim 14 further comprising an antiviral agent selected from the group consisting of aciclovir and valaciclovir.

19. A method for the treatment of a herpes simplex virus 1 or herpes simplex virus 2 infection in an animal, said method comprising administering to the animal a therapeutically effective amount of a compound according to claim 1.

20. A method for the treatment of a condition or disease associated with a herpes viral infection selected from herpes simplex virus 1 and herpes simplex virus 2 in an animal, comprising administering to the animal, a therapeutically effective amount of the compound according to claim 1.

21. A process for preparing the compound according to claim 1 wherein $R^2$ is selected from the group consisting of H, alkyl, cycloalkyl, alkenyl, cycloalkenyl, —$NR^7R^8$, —$OR^7$, —OAy, —$S(O)_nR^7$, —$S(O)_nAy$, —$R^{10}NR^7R^8$, —$R^{10}NR^7Ay$, Ay, Het, —$NH(CH_2)_m$Het and —$O(CH_2)_m$Het; and $R^3$ and $R^4$ are both H, said process comprising reacting a compound of formula (IX):

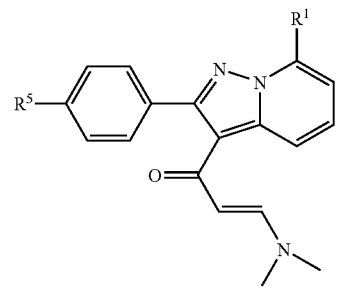

with an amine of formula (X):

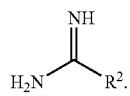

22. A process for preparing the compound according to claim 1 wherein R² is selected from the group consisting of H, alkyl, cycloalkyl, alkenyl, cycloalkenyl, —NR⁷R⁸, —OR⁷, —OAy, —S(O)ₙR⁷, —S(O)ₙAy, —R¹⁰NR⁷R⁸, —R¹⁰NR⁷Ay, Ay, Het, —NH(CH₂)ₘHet and —O(CH₂)ₘHet; R³ is selected from the group consisting of H, alkyl, alkylhydroxy, alkylamine, alkylether, —NR⁷R⁸ where R⁷ and R⁸ are not H, —NR⁷Ay where R⁷ is not H, carboxy, carboxamide, —SO₂NHR⁹, Het and Ay, and R⁴ is H, said process comprising reacting a compound of formula (XVI):

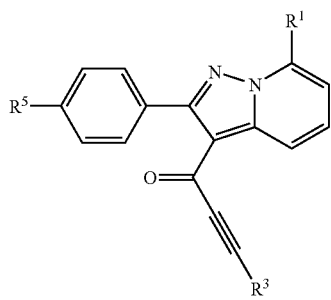

with an amine of formula (X):

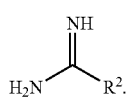

23. The process according to claim 21 further comprising the step of converting the compound of formula (I) or a pharmacutically acceptable saltthereof, to another compound of formula (I) or a pharmaceutically acceptable salt thereof.

24. A process for preparing the compound according to claim 1 wherein R² is selected from the group consisting of H, alkyl, cycloalkyl, alkenyl, cycloalkenyl, —NR⁷R⁸, —OR⁷, —OAy, —S(O)ₙR⁷, —S(O)ₙR⁷, —R¹⁰NR⁷R⁸, —R¹⁰NR⁷R⁸, Ay, Hat, —NH(CH₂)ₘHet and —O(CH₂)ₘHet, said process comprising the steps of a) reacting a compound of formula (XX):

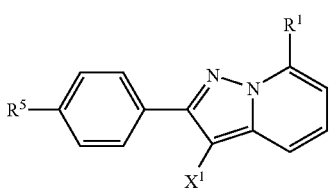

with an amine of formula (X):

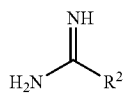

to prepare an intermediate compound; and
b) oxidizing the intermediate compound.

25. A process for preparing the compound according to claim 1, said process comprising reacting a compound of formula (XXII):

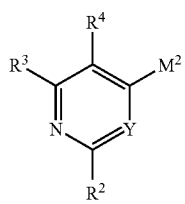

wherein X¹ is chloro, bromo or iodo;
with a compound of formula XXIV:

XXIV wherein M² is selected from the group consisting of —B(OH)₂, —B(ORa)₂, —B(Ra)₂, —Sn(Ra)₃, Zn-halide, ZnRa and Mg-halide, where Ra is alkyl cycycloalkyl and halide is halo.

* * * * *